US011118185B2

(12) United States Patent
Lewin et al.

(10) Patent No.: US 11,118,185 B2
(45) Date of Patent: Sep. 14, 2021

(54) AAV VECTORS FOR TREATMENT OF DOMINANT RETINITIS PIGMENTOSA

(71) Applicants: University of Florida Research Foundation, Incorporated, Gainesville, FL (US); The Trustees of the University of Pennsylvania, Philadelphia, PA (US)

(72) Inventors: Alfred S. Lewin, Gainesville, FL (US); William W. Hauswirth, Gainesville, FL (US); Michael T. Massengill, Gainesville, FL (US); William Beltran, Philadelphia, PA (US); Gustavo D. Aguirre, Media, PA (US); Artur Cideciyan, Lafayette Hill, PA (US); Samuel Jacobson, Penn Valley, PA (US)

(73) Assignees: University of Florida Research Foundation, Incorporated, Gainesville, FL (US); The Trustees of the University of Pennsylvania, Philadelphia, PA (US)

(*) Notice: Subject to any disclaimer, the term of this patent is extended or adjusted under 35 U.S.C. 154(b) by 458 days.

(21) Appl. No.: 16/081,307

(22) PCT Filed: Mar. 1, 2017

(86) PCT No.: PCT/US2017/020289
§ 371 (c)(1),
(2) Date: Aug. 30, 2018

(87) PCT Pub. No.: WO2017/151823
PCT Pub. Date: Sep. 8, 2017

(65) Prior Publication Data
US 2019/0093111 A1 Mar. 28, 2019

Related U.S. Application Data

(60) Provisional application No. 62/398,451, filed on Sep. 22, 2016, provisional application No. 62/302,122, filed on Mar. 1, 2016.

(51) Int. Cl.
*C12N 15/86* (2006.01)
*C12N 15/113* (2010.01)
*A61P 27/02* (2006.01)
*C12N 7/00* (2006.01)

(52) U.S. Cl.
CPC .......... *C12N 15/1138* (2013.01); *A61P 27/02* (2018.01); *C12N 7/00* (2013.01); *C12N 15/113* (2013.01); *C12N 15/86* (2013.01); *C12N 2310/122* (2013.01); *C12N 2310/14* (2013.01); *C12N 2310/141* (2013.01); *C12N 2310/531* (2013.01); *C12N 2330/51* (2013.01); *C12N 2750/14143* (2013.01)

(58) Field of Classification Search
CPC .................................................. C12N 15/1138
See application file for complete search history.

(56) References Cited

U.S. PATENT DOCUMENTS

| 7,138,378 | B1 | 11/2006 | Farrar et al. |
| 8,551,970 | B2 | 10/2013 | Farrar et al. |
| 2007/0009899 | A1 | 1/2007 | Mounts |
| 2013/0064815 | A1 | 3/2013 | Coller |
| 2015/0159171 | A1 | 6/2015 | Deglon |
| 2017/0348387 | A1 | 12/2017 | Aguirre et al. |

FOREIGN PATENT DOCUMENTS

| CN | 102061308 A | 5/2011 |
| JP | 2006-523464 A | 10/2006 |
| JP | 2007-530431 A | 11/2007 |
| JP | 2010-518821 A | 6/2010 |
| WO | WO 2004/020631 A2 | 3/2004 |
| WO | WO 2005/090572 A2 | 9/2005 |
| WO | WO 2008/100627 A2 | 8/2008 |
| WO | WO 2009/035792 A1 | 3/2009 |
| WO | WO 2010/127209 A2 | 11/2010 |
| WO | WO 2014/138792 A1 | 9/2014 |
| WO | WO 2015/143418 A2 | 9/2015 |
| WO | WO 2016/138353 A1 | 9/2016 |
| WO | WO 2016/176690 A2 | 11/2016 |
| WO | WO 2017/137493 A1 | 8/2017 |
| WO | WO 2017/151823 A1 | 9/2017 |

OTHER PUBLICATIONS

PCT/US2017/020289, Jul. 19, 2017, International Search Report and Written Opinion.
PCT/US2017/020289, Sep. 13, 2018, International Preliminary Report on Patentability.
EP 17760752.0, Jul. 5, 2019, Supplementary Partial European Search Report.
EP 17760752.0, Oct. 15, 2019, Extended European Search Report.
PCT/US2019/035159, Sep. 12, 2019, International Search Report and Written Opinion.
Extended European Search Report for Application No. EP 17760752.0 dated Oct. 15, 2019.

(Continued)

*Primary Examiner* — Scott Long
(74) *Attorney, Agent, or Firm* — Wolf, Greenfield & Sacks, P.C.

(57) ABSTRACT

Aspects of the disclosure relate to methods and compositions for treating retinitis pigmentosa. In some aspects, the disclosure provides compositions and methods for delivering an interfering nucleic acid (for example an interfering RNA) to a subject in order to reduce expression of one or both alleles of an endogenous rho gene (for example a mutant rho allele associated with retinitis pigmentosa) in the subject. In some embodiments, a replacement rho gene that is resistant to the interfering nucleic acid also is delivered to the subject.

34 Claims, 30 Drawing Sheets

Specification includes a Sequence Listing.

(56) References Cited

OTHER PUBLICATIONS

International Search Report and Written Opinion for Application No. PCT/US2019/035159 dated Sep. 12, 2019.
Supplementary Partial European Search Report for Application No. EP 17760752.0 ated Jul. 5, 2019.
Behrman et al., A CHOP-regulated microRNA controls rhodopsin expression. J Cell Biol. Mar. 21, 2011; 192(6):919-27. doi: 10.1083/jcb.201010055. Epub Mar. 14, 2011.
Froebel et al., Effects of Pathogenic Variations in the Human Rhodopsin Gene (hRHO) on the Predicted Accessibility for a Lead Candidate Ribozyme. Invest Ophthalmol Vis Sci. Jul. 1, 2017; 58(9):3576-3591. doi: 10.1167/iovs.16-20877.
Gorbatyuk et al., Suppression of mouse rhodopsin expression in vivo by AAV mediated siRNA delivery. Vision Res. Apr. 2007;47(9):1202-8. doi: 10.1016/j.visres.2006.11.026. Epub Feb. 12, 2007. PMID: 17292939; PMCID: PMC1892214.
Lewin et al., Gene augmentation for adRP mutations in RHO. Cold Spring Harb Perspect Med. Jul. 18, 2014;4(9):a017400. doi: 10.1101/cshperspect.a017400.
Mao et al., Long-term rescue of retinal structure and function by rhodopsin RNA replacement with a single adeno-associated viral vector in P23H RHO transgenic mice. Hum Gene Ther. Apr. 2012;23(4):356-66. doi: 10.1089/hum.2011.213. Epub Mar. 28, 2012.
Millington-Ward et al., Suppression and replacement gene therapy for autosomal dominant disease in a murine model of dominant retinitis pigmentosa. Mol Ther. Apr. 2011;19(4):642-9. doi: 10.1038/mt.2010.293. Epub Jan. 11, 2011.
Murray et al., Allele-Specific Inhibition of Rhodopsin With an Antisense Oligonucleotide Slows Photoreceptor Cell Degeneration. Invest Ophthalmol Vis Sci. Oct. 2015; 56(11):6362-75. doi: 10.1167/iovs.15-16400.
Rosas et al., Patterns of scAAV vector insertion associated with oncogenic events in a mouse model for genotoxicity. Mol Ther. Nov. 2012; 20(11):2098-110. doi: 10.1038/mt.2012.197. Epub Sep. 18, 2012.
International Search Report and Written Opinion for Application No. PCT/US2017/020289 dated Jul. 19, 2017.
International Preliminary Report on Patentability for Application No. PCT/US2017/020289 dated Sep. 13, 2018.

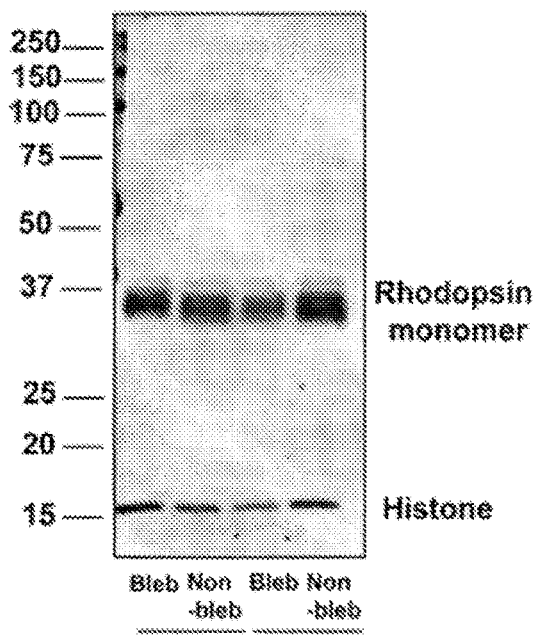
FIG. 5A
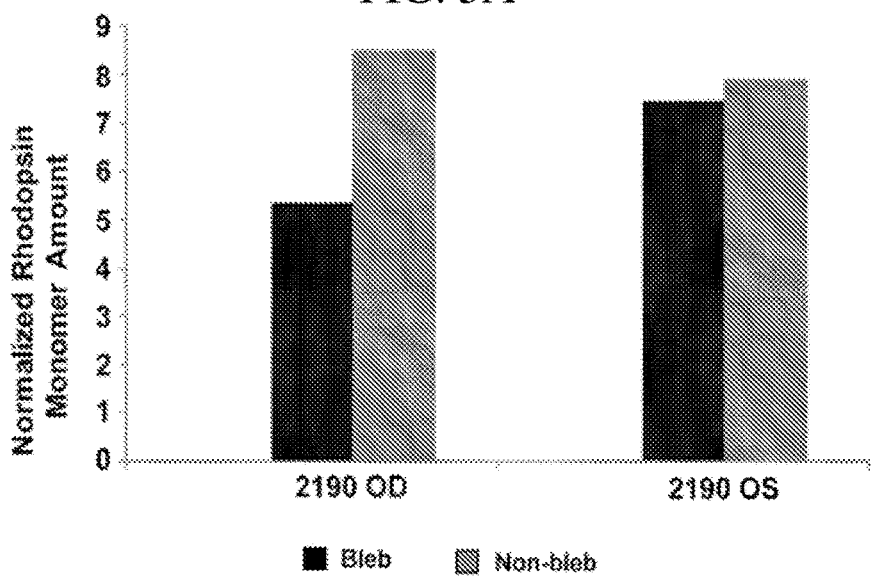
FIG. 5B
| | Viral vector | Titer (vg/ml, 150 ul) | Normalized RHO amounts | | Percent (Bleb/Non-bleb) | Percent KD |
|---|---|---|---|---|---|---|
| | | | Bleb | Non-Bleb | | |
| 2190 OD | AAV2/5-sc-MOP500-rGFP-shRNA-Rho131 | 5 x 10¹² | 5.36 | 8.51 | 62.98 | 37.02 |
| 2190 OS | AAV2/5-sc-MOP500-rGFP-shRNA-Rho131 | 1 x 10¹² | 7.45 | 7.91 | 94.18 | 5.82 |
FIG. 5C

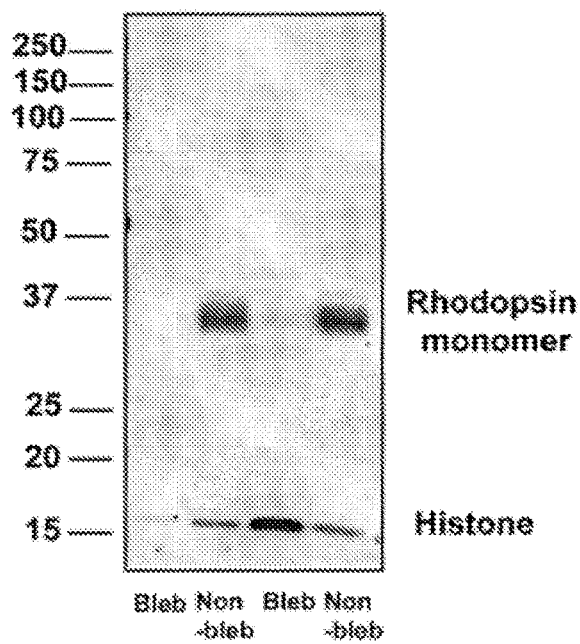
FIG. 7A
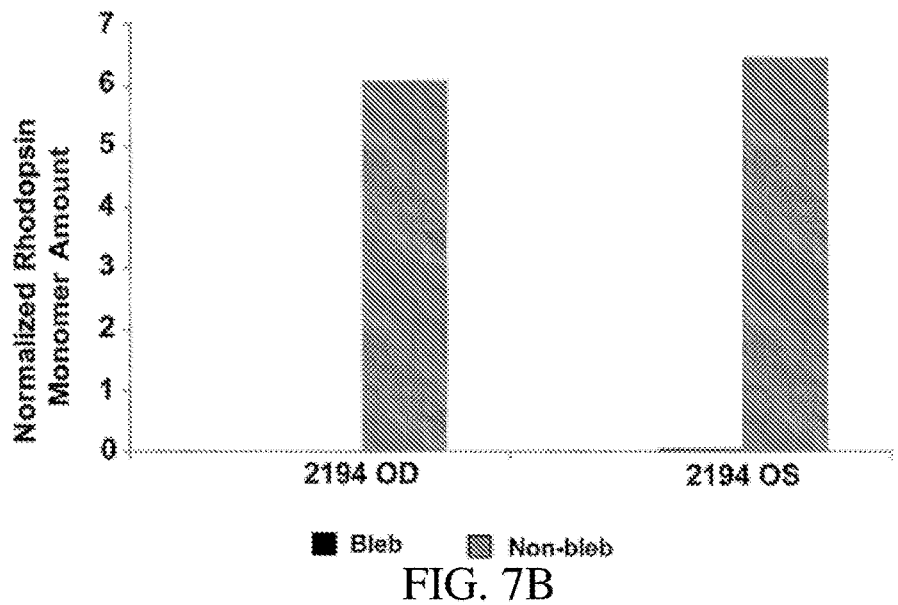
FIG. 7B
| | Viral vector | Titer (vg/ml) | Normalized RHO amounts | | (Bleb/Non-bleb) | Percent KD |
| --- | --- | --- | --- | --- | --- | --- |
| | | | Bleb | Non-Bleb | | |
| 2194 OD | AAV2/5-sc-MOP500-rGFP-shRNA-Rho131 | $5 \times 10^{12}$ | 0.00 | 6.09 | 0.00 | 100.00 |
| 2194 OS | AAV2/5-sc-MOP500-rGFP-shRNA-Rho131 | $1 \times 10^{12}$ | 0.05 | 6.46 | 0.77 | 99.23 |
FIG. 7C

| Dog ID | Viral Titer (volume) | Percent knockdown RNA | Replicate | Percent Knockdown Protein | Average Percent Knockdown Protein |
|---|---|---|---|---|---|
| 2194 OD | $5 \times 10^{12}$ (150 ul) | 100.0 | — | 100.0 | — |
| 2194 OS | $1 \times 10^{12}$ (150 ul) | 100.0 | — | 99.2 | — |
| BR442 OS | $1 \times 10^{12}$ (150 ul) | 100.0 | Rep1 ● Rep2 ● Rep3 ● | 100.0 100.0 100.0 | 100.0 |
| GSR2 OS | $5 \times 10^{11}$ (110 ul) | 97.4 | Rep1 ● Rep2 ● Rep3 ● | 80.8 84.3 89.5 | 84.8 |
| P1474 OD | $2.5 \times 10^{11}$ (150 ul) | 25.7 | Rep1 ● Rep2 ● Rep3 ● | 32.7 38.5 34.4 | 53.3 |
| N282 OS | $1 \times 10^{11}$ (160 ul) | 78.1 | Rep1 ● Rep2 ● Rep3 ● | 24.8 -5.4 -4.6 | 4.9 |

FIG. 13E

| Dog ID-eye | Viral titer (volume) | Percentage of remaining RHO RNA | Replicate | Percentage of remaining RHO protein | Mean percentage of remaining RHO protein |
|---|---|---|---|---|---|
| EM409-OD | $1 \times 10^{12}$ (150 ul) | 0.0 | Rep1 ●<br>Rep2 ●<br>Rep3 ○ | 0.0<br>0.0<br>0.0 | 0.0 |
| EM411-OD | $5 \times 10^{11}$ (150 ul) | 0.1 | Rep1 ●<br>Rep2 ●<br>Rep3 ○ | 0.0<br>0.0<br>0.0 | 0.0 |
| EM413-OD | $2.5 \times 10^{11}$ (150 ul) | 40.9 | Rep1 ●<br>Rep2 ●<br>Rep3 ○ | 10.1<br>8.4<br>23.5 | 14.0 |
| EM412-OD | $1 \times 10^{11}$ (150 ul) | 25.1 | Rep1 ●<br>Rep2 ●<br>Rep3 ○ | 87.5<br>89.0<br>82.8 | 86.4 |

| Dog ID | Viral Titer (volume) | Percent knockdown RNA | Replicate | Percent Knockdown Protein | Average Percent Knockdown Protein |
|---|---|---|---|---|---|
| EM409 OD | $1 \times 10^{12}$ (150 ul) | 100.0 | Rep1<br>Rep2<br>Rep3 | 100.0<br>100.0<br>100.0 | 100.0 |
| EM411 OD | $5 \times 10^{11}$ (150 ul) | 99.9 | Rep1<br>Rep2<br>Rep3 | 100.0<br>100.0<br>100.0 | 100.0 |
| EM413 OD | $2.5 \times 10^{11}$ (150 ul) | 59.1 | Rep1<br>Rep2<br>Rep3 | 89.9<br>91.6<br>76.5 | 86.0 |
| EM412 OD | $1 \times 10^{11}$ (150 ul) | 74.9 | Rep1<br>Rep2<br>Rep3 | 12.5<br>11.0<br>17.2 | 13.6 |

FIG. 15E

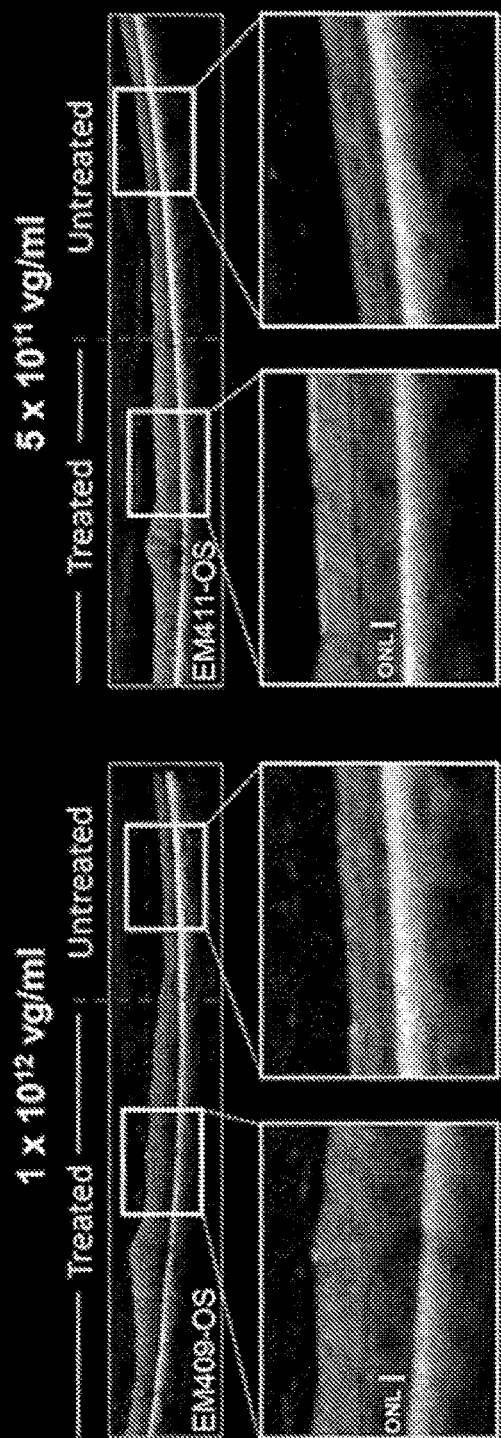
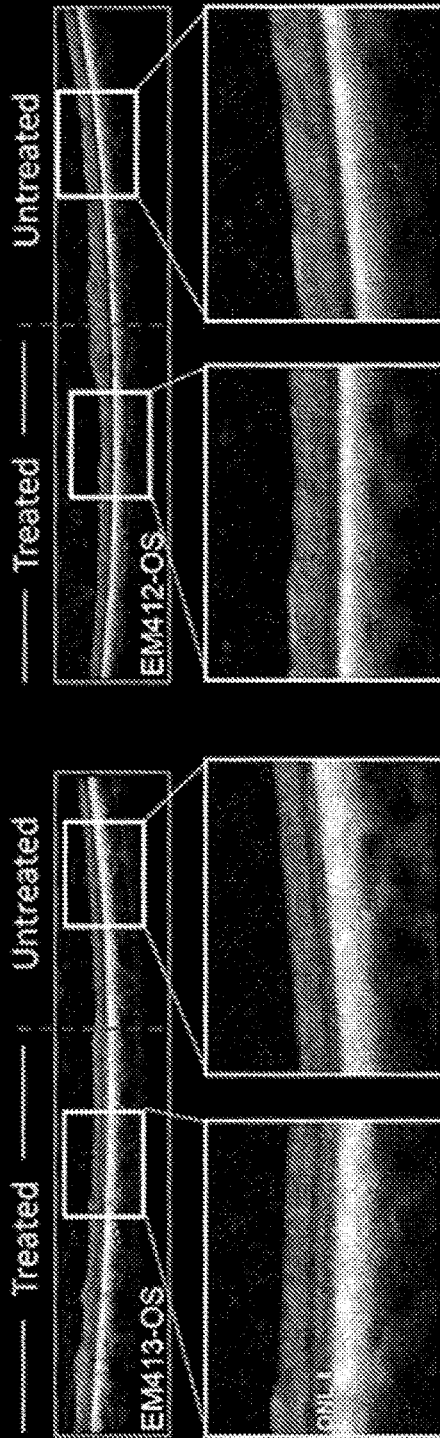
FIG. 16A  FIG. 16B
FIG. 16C  FIG. 16D

AAV2/5-sc-HOP-$RHO_{820}$-H1-$shRNA_{820}$

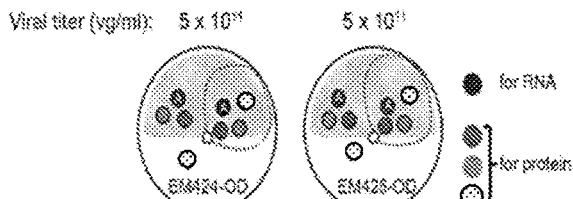

FIG. 19A

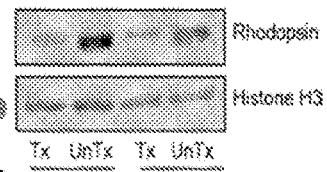

FIG. 19B

Protein

| Dog ID | Viral titer (vol) | Replicate | Percentage of remaining RHO protein | Percentage (mean ± SD) of remaining RHO protein |
|---|---|---|---|---|
| EM424-OD | $5 \times 10^{11}$ (150 µl) | Rep1 | 18.0 | 30.7 ± 16.2 |
| | | Rep2 | 25.2 | |
| | | Rep3 | 49.0 | |
| EM425-OD | $5 \times 10^{11}$ (150 µl) | Rep1 | 19.1 | 33.0 ± 12.3 |
| | | Rep2 | 42.3 | |
| | | Rep3 | 37.6 | |

FIG. 19C

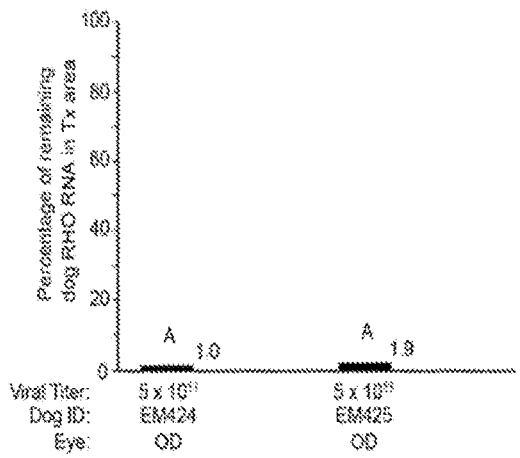

FIG. 19D

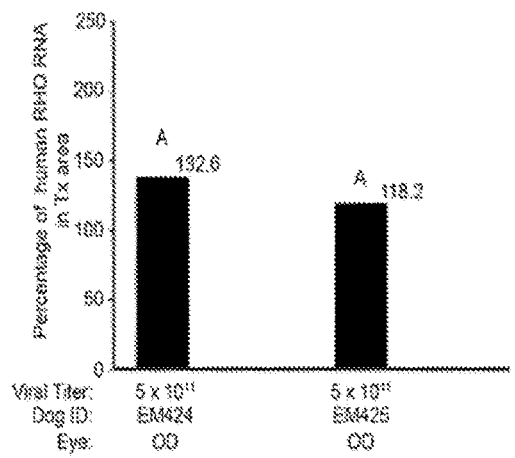

FIG. 19E

RNA

| Dog ID | Viral titer (vol) | Dog RHO RNA | Human RHO RNA | Percentage of remaining dog RHO RNA (Tx/UnTX) | Percentage of human RHO RNA (Human RNA Tx / Dog RNA UnTX) |
|---|---|---|---|---|---|
| EM424 Tx-A | $5 \times 10^{11}$ (150 µl) | 332 | 44361 | 1.0 | 132.6 |
| EM424 UnTx-A | | 33457 | 877 | | |
| EM425 Tx-A | $5 \times 10^{11}$ (150 µl) | 662 | 42298 | 1.9 | 118.2 |
| EM425 UnTx-A | | 35781 | 10 | | |

FIG. 19F

AAV2/5-sc-HOP-$RHO_{820}$-H1-$shRNA_{820}$
FIG. 20A
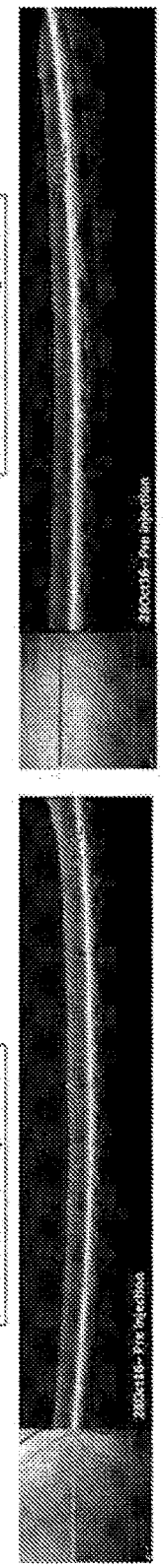
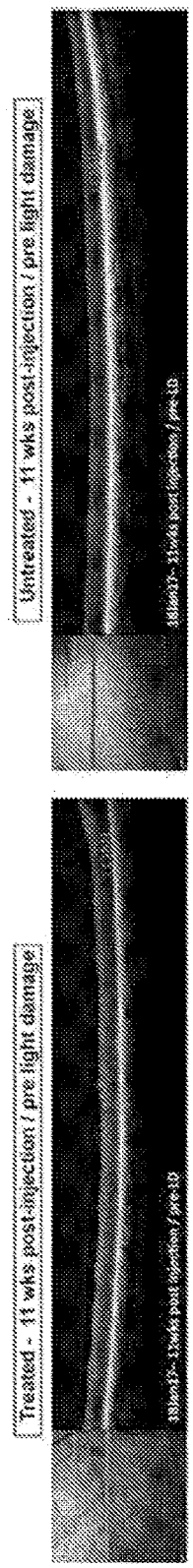
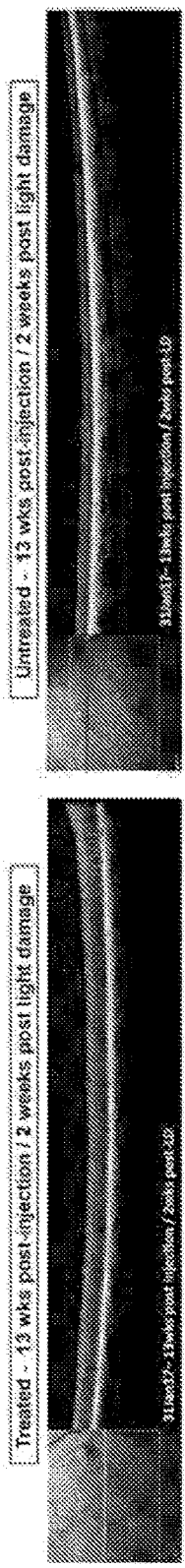
FIG. 20B
FIG. 20C

AAV VECTORS FOR TREATMENT OF DOMINANT RETINITIS PIGMENTOSA

CROSS-REFERENCE TO RELATED APPLICATIONS

This application is a national stage filing under 35 U.S.C. 371 of International Patent Application Serial No. PCT/US2017/020289, filed Mar. 1, 2017, entitled "AAV VECTORS FOR TREATMENT OF DOMINANT RETINITIS PIGMENTOSA", which claims the benefit of U.S. Provisional Patent Application No. 62/302,122, filed Mar. 1, 2016, and U.S. Provisional Patent Application No. 62/398,451, filed Sep. 22, 2016, the contents of each of which are incorporated herein by reference in their entireties.

GOVERNMENT SUPPORT

This invention was made with government support under grant number R24-EY022012 awarded by the National Institutes of Health. The government has certain rights in the invention.

BACKGROUND

Autosomal dominant retinitis pigmentosa (adRP) is a blinding disease affecting 1 in 12,000 people. A sizeable fraction of these individuals carry a mutation in the gene (rho) for rhodopsin, the light harvesting pigment protein of the photoreceptor cells in the retina. The disease is dominant because inheritance of the mutated gene from either parent leads to retinal degeneration and eventual blindness. Over 100 different mutations identified in rho lead to blindness. There is currently no approved drug or gene therapy treatment for adRP. Thus, there is a need for effective treatment options pertaining to any and all causes of adRP and related conditions.

SUMMARY

Aspects of the application relate to compositions and methods for treating retinitis pigmentosa (e.g., dominant retinitis pigmentosa) in a subject (e.g., in a human). In some embodiments, one or both alleles of the rhodopsin gene (rho gene) of a subject are silenced by administering an interfering RNA molecule to a subject (e.g., to a subject having retinitis pigmentosa, for example to a human having dominant retinitis pigmentosa). In some embodiments, a replacement rho gene also is administered to the subject to provide a functional RHO protein to restore photoreceptor function to the subject. In some embodiments, the replacement rho gene has one or more nucleotide substitutions relative to the endogenous gene allele(s) that render the replacement gene resistant to the effects of the interfering RNA. In some embodiments, the replacement rho gene is a human rho gene (e.g., a wild-type human rho gene) that includes one or more (e.g., 1, 2, 3, 4, 5, or more) substitutions to render the gene resistant (also referred to as "hardened") to degradation mediated by the interfering RNA molecule. In some embodiments, the one or more nucleotide substitutions are in the coding sequence of the rho gene. In some embodiments, the one or more nucleotide substitutions are silent (e.g., they do not alter the amino acid sequence of the RHO protein). In some embodiments, the one or more substitutions introduce an amino acid change, but the resulting RHO protein is still sufficiently functional to be therapeutically effective (to restore or maintain at least partial sight, or normal sight).

In some embodiments, an interfering RNA and/or a replacement gene can be delivered to a subject using any suitable technique. In some embodiments, an interfering RNA is provided to a subject in the form of a gene that encodes the interfering RNA. In some embodiments, the gene that encodes the interfering RNA is provided to the subject in a recombinant adeno-associated virus (rAAV). In some embodiments, the replacement gene is provided to the subject in an rAAV. In some embodiments, the gene that encodes the interfering RNA and the replacement gene are provided in the same rAAV (for example they are both encoded on the same recombinant genome flanked by AAV inverted terminal repeats (ITRs)). In some embodiments, both genes are under control of the same promoter. In some embodiments, the genes are under the control of two different promoters. In some embodiments, the gene that encodes the interfering RNA and the replacement gene are provided in different rAAVs.

In some embodiments, the interfering RNA is a synthetic ribonucleic acid (RNA) molecule comprising:

a) a sense strand of sequence
(SEQ ID NO: 1)
CUGCCUACAUGUUUCUGCU
and an antisense strand of sequence
(SEQ ID NO: 2)
AGCAGAAACAUGUAGGCAG;

b) a sense strand of sequence
(SEQ ID NO: 3)
CCUACAUGUUUCUGCUGAU
and an antisense strand of sequence
(SEQ ID NO: 4)
AUCAGCAGAAACAUGUAGG;

c) a sense strand of sequence
(SEQ ID NO: 5)
GCAUGGUCAUCAUCAUGGU
and an antisense strand of sequence
(SEQ ID NO: 6)
ACCAUGAUGAUGACCAUGC;
or d) a sense strand of sequence
(SEQ ID NO: 7)
GUGGCAUUCUACAUCUUCA
and an antisense strand of sequence
(SEQ ID NO: 8)
UGAAGAUGUAGAAUGCCAC.

In some embodiments, the synthetic RNA molecule is a small interfering RNA (siRNA). In some embodiments, the interfering RNA is a small hairpin RNA (shRNA). In some embodiments, the shRNA comprises a loop having an RNA of sequence UCAAGAG (SEQ ID NO: 9) or RNA of sequence UGUGCUU (SEQ ID NO: 10).

In some embodiments, the synthetic RNA molecule is an artificial micro RNA (miRNA). In some embodiments, the artificial miRNA has an RNA sequence of:

(SEQ ID NO: 19)
UGCUGUUGACAGUGAGCGA(X)„UAGUGAAGCCACAGAUGUA(Y)„CUGC
CUACUGCCUCGGA, a) $(X)_n$ comprises SEQ ID NO: 1 and $(Y)_n$ comprises SEQ ID NO: 2;
b) $(X)_n$ comprises SEQ ID NO: 3 and $(Y)_n$ comprises SEQ ID NO: 4;
c) $(X)_n$ comprises SEQ ID NO: 5 and $(Y)_n$ comprises SEQ ID NO: 6; or
d) $(X)_n$ comprises SEQ ID NO: 7 and $(Y)_n$ comprises SEQ ID NO: 8.

In some embodiments, a synthetic RNA described above or elsewhere in this application further comprises an unpaired overhang sequence at the 5' and/or 3' end. In some embodiments, the unpaired overhang sequence comprises a sequence of repeating bases. In some embodiments, the sequence of repeating bases comprises repeating uracil (U) bases. In some embodiments, the unpaired overhang sequence is UU.

In some embodiments, a composition (e.g., a composition for administration to a subject) comprises one or more (e.g., 2, 3, or 4) of the interfering RNAs (e.g., synthetic RNA molecules) described above or elsewhere in this application. In some embodiments, a composition (e.g., a composition for administration to a subject) comprises a nucleic acid (e.g., a DNA) that encodes one or more (e.g., 2, 3, or 4) of the interfering RNAs (e.g., synthetic RNA molecules) described above or elsewhere in this application.

In some embodiments, a composition also includes one or more physiologically acceptable carriers and/or one or more physiologically acceptable adjuvants.

In some embodiments, a vector encodes one or more (1, 2, 3, or 4, or more) shRNAs and/or artificial miRNAs (e.g., described above or elsewhere herein). In some embodiments, the shRNAs have a sequence of one or more of SEQ ID NOs: 11-18.

In some embodiments, a vector encodes a replacement rho gene.

In some embodiments, a vector encodes a replacement rho gene and/or one or more shRNAs and/or artificial miRNAs (e.g., described above or elsewhere herein).

In some embodiments, the vector is an expression plasmid. In some embodiments, the vector is a recombinant viral genome (e.g., an rAAV genome). In some embodiments, the vector is a viral vector. In some embodiments, the viral vector comprises an rAAV genome.

In some embodiments, a method of decreasing RHO expression in a subject includes administering to the subject a composition including one or more interfering RNAs and/or one or more vectors each encoding (e.g., capable of expressing) one or more interfering RNAs described above or elsewhere herein.

In some embodiments, a method of treating retinitis pigmentosa (RP) in a subject includes administering to the subject both a composition comprising an interfering RNA or a vector expressing an interfering RNA and a composition comprising a recombinant rho gene (for example a vector encoding the recombinant rho gene), wherein the rho gene is resistant to targeting by the interfering RNA.

In some embodiments, the recombinant rho gene is delivered using an rAAV. In some embodiments, the interfering RNA and the recombinant rho gene are delivered using the same rAAV. In some embodiments, the interfering RNA and the recombinant rho gene are both under expression control of a single promoter sequence. In some embodiments, the interfering RNA and the recombinant rho gene are each under expression control of independent promoter sequences (e.g., either constitutive or inducible promoters). In some embodiments, the interfering RNA and/or modified rho gene are under expression control of (e.g., operatively connected to) a human promoter or a promoter of a different species (e.g., a viral promoter, a prokaryotic promoter, or a eukaryotic promoter, for example, a promoter from a non-human primate, a rodent, a dog, a cat, a pig, or other species). In some embodiments, a promoter is an RNA polymerase III promoter (e.g., H1 RNA polymerase III promoter) or an RNA polymerase II promoter, or an RNA polymerase I promoter. In some embodiments, the interfering RNA is shRNA, and the shRNA is under expression control of an RNA polymerase III promoter (e.g., H1 RNA polymerase III promoter). In some embodiments, the interfering RNA is an artificial miRNA, and the artificial miRNA is under expression control of an RNA polymerase II promoter. In some embodiments, the recombinant rho gene is under expression control of a constitutive or inducible promoter (e.g., a human promoter, an eye-specific promoter). In some embodiments, the constitutive or inducible promoter is a mouse promoter (e.g., a mouse opsin (MOPS) promoter).

In some embodiments, the subject is a mammal. In some embodiments, the mammal is a rodent or a dog. In some embodiments, the mammal is a human (e.g., a human having or known to have, for example diagnosed as having, retinitis pigmentosa, for example dominant retinitis pigmentosa). These and other aspects are described in the following drawings, examples, and claims.

BRIEF DESCRIPTION OF DRAWINGS

The drawings and following brief descriptions provide non-limiting examples of aspects of the compositions and methods described herein.

FIGS. 5A-5C show (FIG. 5A) a rhodopsin immunoblot in biopsy punches taken from bleb and non-bleb areas of canine retina. FIG. 5B shows quantitation of rhodopsin monomer amounts, normalized to histone. FIG. 5C is a table showing the normalized amounts.

FIG. 6A is a plot of the absolute numbers of canine RHO RNA. FIG. 6B is a table showing the absolute RNA numbers.

FIGS. 7A-7C show (FIG. 7A) a rhodopsin immunoblot in biopsy punches taken from bleb and non-bleb areas of canine retina. FIG. 7B shows quantitation of rhodopsin monomer amounts, normalized to histone. FIG. 7C is a table showing the normalized amounts.

FIG. 8A is a plot of the absolute numbers of canine RHO RNA. FIG. 8B is a table showing the absolute RNA numbers.

FIGS. 13A-13E show RNA and protein analysis of rhodopsin knockdown with different viral titers of AAV2/5-sc-H1-shRNA820 injected subretinally in WT $RHO^{+/+}$ dogs. FIG. 13A shows retinal maps showing position of biopsy punches used for western blot analysis and RNA quantitation. Paired dark gray, gray and dotted circles indicate the position of biopsy punches in the bleb/treated and non-bleb/untreated regions for each replication of western blot, whereas the black circles indicate the positions of biopsy punches for RNA quantitation. FIG. 13B shows a bar graph showing remaining canine Rhodopsin RNA in the treated area as a percentage of levels measured in the untreated area of the same retina. FIG. 13C shows immunoblot showing the amount of Rhodopsin in biopsy punches taken from treated (Tx) and untreated (UnTx) areas of canine retina. Histone H3 was used for normalization. Bar graphs show remaining canine Rhodopsin protein as a percentage of levels measured in the untreated area of the same retina. FIG. 13D is a table showing numerical values from each experiment reported as a percentage of RNA or protein remaining. FIG. 13E is another table showing the numerical values from each experiment reported as percent knockdown of RNA or protein.

FIG. 14A shows ONL thickness maps; FIG. 14B shows ELM/IS/OS maps of normalized intensity; FIG. 14C shows ONL thickness values; and FIG. 14D shows values of normalized intensity of the ELM/IS/OS layers.

FIGS. 15A-15E show RNA and protein analysis of rhodopsin knockdown with different viral titers of AAV2/5-sc-H1-shRNA820 injected subretinally in mutant $RHO^{T4R/+}$ dogs. FIG. 15A shows retinal maps showing position of biopsy punches used for western blot analysis and RNA quantitation. Paired dark gray, gray and dotted circles indicate the position of biopsy punches in the bleb and non-bleb region for each replication of western blot, whereas the black circles indicate the position of biopsy punches for RNA quantitation. FIG. 15B is a bar graph showing the amount of remaining canine Rhodopsin RNA as a percentage of levels measured in the untreated area of the same retina. FIG. 15C is an immunoblot showing the amount of canine Rhodopsin in biopsy punches taken from treated (Tx) and untreated (UnTx) areas of canine retina. Histone H3 was used for normalization. Bar graphs show the amount of remaining canine Rhodopsin protein as a percentage of levels measured in the untreated area of the same retina. FIG. 15D is a table showing numerical values from each experiment reported as a percentage of RNA or protein remaining. FIG. 15E is another table showing the numerical values from each experiment reported as percent knockdown of RNA or protein.

FIGS. 16A-16D show OCT B scans encompassing the treated (with different viral titers of AAV2/5-sc-H1-shRNA820) and untreated retinal areas of $RHO^{T4R/+}$ dogs 2 weeks following exposure to a brief dose of light that causes acute retinal degeneration in mutant $RHO^{T4R/+}$ dogs. (FIG. 16A) OCT scan of a dog treated with $1 \times 10^{12}$ vg/ml. (FIG. 16B) OCT scan of a dog treated with $5 \times 10^{11}$ vg/ml. (FIG. 16C) OCT scan of a dog treated with $2.5 \times 10^{11}$ vg/ml. (FIG. 16D) OCT scan of a dog treated with $1 \times 10^{11}$ vg/ml.

(FIG. 17A) ONL thickness map of an untreated WT control dog (left panel), and ONL thickness map of EM411-OS treated with AAV2/5-sc-H1-shRNA820 at 5E+11 vg/ml and showing preserved ONL thickness in the treated/bleb region weeks after light-induced damage. Black and white curve shows the limits of the bleb as seen immediately after the subretinal injection. Panels below show OCT B scans with ONL colored in darker gray (middle band) for visualization purposes. (FIG. 17B) Loci outside and inside the bleb were selected for ONL thickness measurements.

FIGS. 19A-19F show RNA and protein analysis of rhodopsin knockdown and replacement with AAV2/5-sc-HOP-RHO820-H1-shRNA820 injected subretinally in mutant $RHO^{T4R/+}$ dogs at $5 \times 10^{11}$ vg/ml titer. FIG. 19A shows retinal maps showing position of biopsy punches used for western blot analysis and RNA quantitation. Paired dark gray, gray and dotted circles indicate the position of biopsy punches in the treated (Tx) and untreated (UnTx) regions for each replication of western blot, whereas the black circles indicate the position of biopsy punches for RNA quantitation. FIG. 19B shows immunoblot showing the amount of total rhodopsin (canine+human RHO820) in biopsy punches taken from treated (Tx) and untreated (UnTx) areas of canine retina. Histone H3 was used for normalization. Bar graphs show the percentage of remaining rhodopsin protein in the Treated and untreated areas. Note the loss of the lower MW band (corresponding to mutant T4R RHO protein) in the treated areas of EM424-OD and EM425-OD. FIG. 19C is a table showing numerical values for each pair of punches used for protein quantification. FIG. 19D is a bar graph showing remaining canine Rhodopsin RNA in the treated areas as a percentage of canine RHO RNA levels measured in untreated areas. FIG. 19E is a bar graph showing levels of human RHO820 in the treated areas as a percentage of canine RHO RNA levels measured in untreated areas. FIG. 19F is a table showing numerical values for each pair of punches used for RNA quantification.

FIGS. 20A-20C show in vivo retinal imaging showing protection from light-induced retinal degeneration in the region of a mutant $RHO^{T4R/+}$ retina treated with AAV2/5-sc-HOP-RHO820-H1-shRNA820 at $5 \times 10^{11}$/vg/ml titer. FIG. 20A shows en face cSLO composite showing 2 weeks post light exposure the retinal region (border demarcated by white arrows) that was protected from degeneration. Light gray arrow indicates the location within the treated area of the OCT B scans shown in FIG. 20B, dark gray arrow indicates the location within the untreated area of the OCT B scans shown in FIG. 20C. FIG. 20B shows OCT B scans within the treated area before injection, 11 weeks post injection, and 13 weeks post injection/2 weeks post light exposure. ONL thickness is preserved throughout the treated area at both time-points following the injection of the viral vector. FIG. 20C shows OCT B scans within the untreated area before injection, 11 weeks post injection, and 13 weeks post injection/2 weeks post light exposure. ONL is preserved up to 11 weeks post injection but is completely lost 2 weeks after light exposure.

DETAILED DESCRIPTION

Figure 1A:
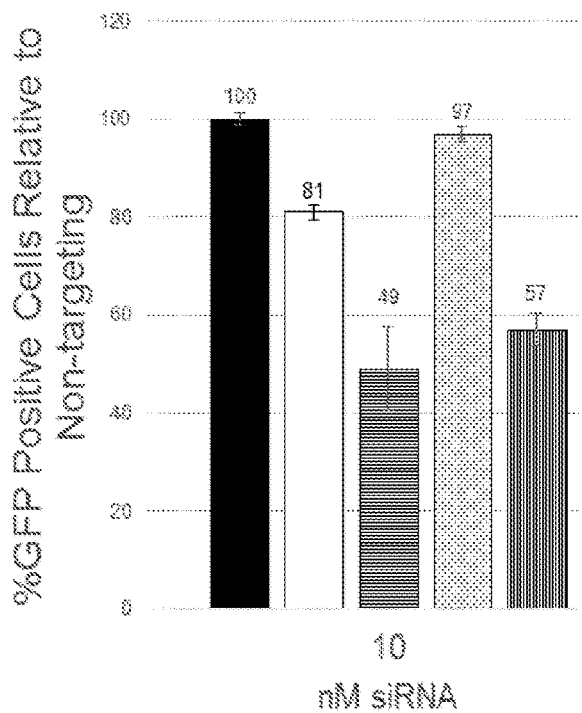
FIG. 1A-C shows knockdown of GFP tagged human rhodopsin measured by FACS (fluorescence-activated cell sorting). This experiment was performed in 293T cells with three biologic replicates. 500 ng of GFP-Tagged human RHO cDNA was co-transfected with different siRNAs. Transfections were performed utilizing LIPO-FECTAMINE® 2000 transfection reagent. The control was a non-targeting siRNA purchased from Dharmacon. Samples were incubated for 72 hours and then analyzed by flow cytometry, first gated for Forward and Side scatter to exclude non-viable particles then for GFP expression above autofluorescence. The number of GFP positive cells treated with the control siRNA was set to 100%.

Aspects of the application provide methods and compositions that are useful for treating retinitis pigmentosa in a subject (e.g., in a subject having dominant retinitis pigmentosa).

In some embodiments, the expression of endogenous rhodopsin (e.g., mutant and normal) is reduced or suppressed using RNA interference, and the missing protein is replaced by delivering a gene for the normal protein that is engineered to remove the target site for the RNA inhibitor.

In some embodiments, a single adeno-associated virus (AAV) vector is used to deliver both the RNA agent (e.g., small hairpin RNA or artificial microRNA) and the recombinant RHO gene.

In some embodiments, small hairpin RNAs, artificial microRNAs (a-miRs) and/or RNA enzymes (ribozymes) can be designed to degrade rhodopsin mRNA by targeting sequences that are common in mouse, human, and dog. Such molecules can be useful to test inhibition in cell culture, in mice, and/or in dogs, to develop inhibitors that can work in human patients.

In some embodiments, small interfering nucleic acids (e.g., RNAs) are provided that target both human and dog rhodopsin mRNA. In some embodiments, four small interfering RNAs that digest human and canine rhodopsin (RHO) mRNA are provided for the purpose of depleting endogenously made rhodopsin in humans and animals. In some embodiments, these interfering RNAs target rhodopsin expression in subjects having a dominant inherited form of retinitis pigmentosa caused by mutations in RHO. Some of these mutations lead to a toxic form of the protein, the synthesis of which must be silenced to prevent degeneration of the retina.

In some embodiments, an interfering nucleic acid (e.g., RNA) is designed to target a sequence that is specific for a mutant rho gene (e.g., it is complementary to a sequence that is present in the mutant rho gene and not present in a wild-type rho gene). However, in some embodiments an interfering nucleic acid is designed to target a wild-type sequence in a mutant endogenous rho gene (e.g., having one or more mutations at other positions not targeted by the interfering nucleic acid). In further embodiments, a functional (e.g., wild-type) rho gene that is resistant to the interfering nucleic acid is provided to restore RHO activity in the subject and thereby treat one or more symptoms of a disease or disorder associated with the mutant endogenous rho allele(s) that is/are targeted by the interfering nucleic acid.

In some embodiments, one or more of the interfering RNAs can be delivered using an adeno-associated virus (AAV) vector either as short hairpin RNAs (shRNAs) driven by a promoter (e.g., an RNA polymerase III promoter or other suitable constitutive or inducible promoter) or as artificial microRNAs (miRNAs) driven by a promoter (e.g., using an RNA polymerase II promoter or other suitable constitutive or inducible promoter).

In some embodiments, the same vector expresses a gene (cDNA) that encodes normal rhodopsin but is resistant to the action of the siRNA expressed by the virus.

Non-limiting examples of interfering RNAs are provided in Tables 1-4.

TABLE 1

Small interfering RNA (siRNA)

| SEQ ID NO: | Name | RNA sequence |
|---|---|---|
| 1 | RHO131-S | CUGCCUACAUGUUUCUGCU |
| 2 | RHO131-A | AGCAGAAACAUGUAGGCAG |
| 3 | RHO134-S | CCUACAUGUUUCUGCUGAU |
| 4 | RHO134-A | AUCAGCAGAAACAUGUAGG |
| 5 | RHO765-S | GCAUGGUCAUCAUCAUGGU |
| 6 | RHO765-A | ACCAUGAUGAUGACCAUGC |

TABLE 1-continued

Small interfering RNA (siRNA)

| SEQ ID NO: | Name | RNA sequence |
|---|---|---|
| 7 | RHO820-S | GUGGCAUUCUACAUCUUCA |
| 8 | RHO820-A | UGAAGAUGUAGAAUGCCAC |

TABLE 2

Hairpin loop RNA

| SEQ ID NO: | RNA sequence |
|---|---|
| 9 | UCAAGAG |
| 10 | UGUGCUU |

TABLE 3

Small hairpin RNA (shRNA)

| SEQ ID NO: | Name | RNA sequence |
|---|---|---|
| 11 | RHO131-9 | CUGCCUACAUGUUUCUGCUUCAAGAGAGCAGAAACAUGUAGGCAG |
| 12 | RHO131-10 | CUGCCUACAUGUUUCUGCUUGUGCUUAGCAGAAACAUGUAGGCAG |
| 13 | RHO134-9 | CCUACAUGUUUCUGCUGAUUCAAGAGAUCAGCAGAAACAUGUAGG |
| 14 | RHO134-10 | CCUACAUGUUUCUGCUGAUUGUGCUUAUCAGCAGAAACAUGUAGG |
| 15 | RHO765-9 | GCAUGGUCAUCAUCAUGGUUCAAGAGACCAUGAUGAUGACCAUGC |
| 16 | RHO765-10 | GCAUGGUCAUCAUCAUGGUUGUGCUUACCAUGAUGAUGACCAUGC |
| 17 | RHO820-9 | GUGGCAUUCUACAUCUUCAUCAAGAGUGAAGAUGUAGAAUGCCAC |
| 18 | RHO820-10 | GUGGCAUUCUACAUCUUCAUGUGCUUUGAAGAUGUAGAAUGCCAC |

TABLE 4

Micro RNA (miRNA)

| SEQ ID NO: | Name | RNA sequence |
|---|---|---|
| 19 | miR30 | UGCUGUUGACAGUGAGCGA(X)$_n$UAGUGAAGCCAC AGAUGUA(Y)$_n$CUGCCUACUGCCUCGGA* |

*X and Y are, independently, any base chosen from A, U, C, or G; (X)n corresponds to a sense strand sequence of n bases and (Y)n corresponds to an antisense strand sequence of n bases.

Figure 9:
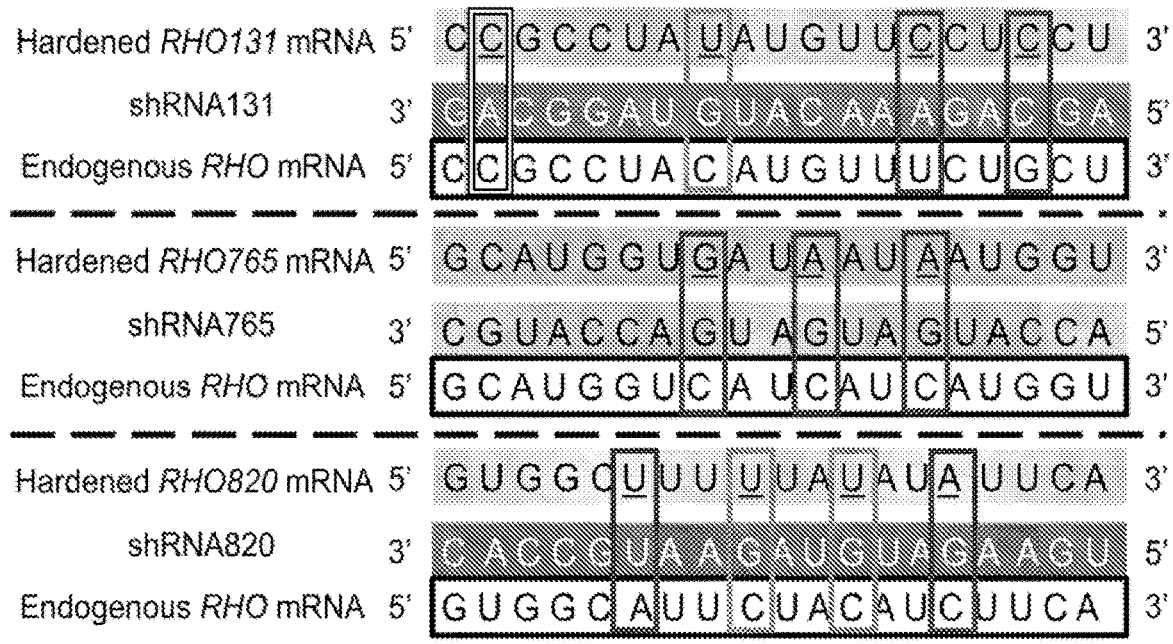
FIG. 9 depicts exemplary base pairing that occurs between shRNA and the target sequence of endogenous human or hardened RHO mRNA. All shRNAs base-pair perfectly with the target sequence of RHO mRNA of dog. White box: mismatch between shRNA and endogenous dog as well as hardened RHO mRNA. Dark gray box: a weak wobble base pairing that occurs in RNA between guanosine and uracil. Light gray box: mismatch between shRNA and hardened RHO mRNA only. Sequences correspond to SEQ ID NOs: 29-37 from top to bottom, respectively.

In some embodiments, a normal (e.g., wild-type) rhodopsin (rho) gene that is hardened can have a sequence based on the human rho gene (e.g., having a sequence shown in Accession No. NG_009115.1; also shown in SEQ ID NO: 41) or the mRNA or a protein coding portion thereof (e.g., an mRNA that is encoded by nucleotides 5001-5456 joined to 7238-7406 joined to 8613-8778 joined to 8895-9134 joined to 9970-11706 of SEQ ID NO: 41 or a protein coding portion thereof, for example the coding sequence that consists of nucleotides 5096-5456 joined to 7238-7406 joined to 8613-8778 joined to 8895-9134 joined to 9970-10080 of SEQ ID NO: 41). In some embodiments, the sequence of a normal rho gene is modified to include one or more (e.g., 2, 3, 4, 5, 6, 7, 8, 9, 10 or more) mutations that render the replacement rho gene resistant to one or more interfering RNAs that are being used as knockdown agent(s) to reduce expression of the mutant endogenous rho gene in a subject being treated. However, in some embodiments, a recombinant rho gene that has a normal (e.g., wild-type) sequence that is not modified can be used if it has a different sequence than the endogenous rho gene or allele(s) that is/are targeted in the subject being treated, and if the knockdown agents being used are designed to target the endogenous rho gene or allele(s) and not the recombinant rho gene being provided. In some embodiments, a rho gene from a different species than the subject being treated can be used. However, in some embodiments, a the rho gene (e.g., a modified rho gene) can be from the same species as the subject being treated. In some embodiments, the one or more modifications in the recombinant rho gene alter the nucleic acid sequence of the coding sequence, but do not alter the encoded protein (e.g., they are silent mutations, for example, at the third position of a codon that can include one of two or more different nucleotides without changing the encoded amino acid). In some embodiments, a recombinant rho gene does not include the intron sequences of a wild-type rho gene. In some embodiments, a recombinant rho gene encodes an mRNA (or a protein coding portion thereof) of a rho gene that has been modified to be resistant to an interfering RNA. In some embodiments, a recombinant rho gene includes a wild-type coding sequence that has been modified to be resistant to an interfering RNA. In some embodiments, the modified wild-type coding sequence is provided along with upstream and/or downstream mRNA sequences that are not derived from the wild-type rho mRNA. In some embodiments, the recombinant replacement rho gene comprises SEQ ID NO: 42. SEQ ID NO: 42 (shown below) encodes a portion of an mRNA sequence that is resistant to an example of an interfering RNA referred to as 820 (e.g., siRNA820 or shRNA820 as described herein). An 820 interfering RNA sequence described herein targets a corresponding sequence in endogenous human rho mRNA as illustrated in FIG. 9, but SEQ ID NO: 42 includes four substitutions (underlined and in bold below, that correspond to positions 9014, 9017, 9020 and 9023 of SEQ ID NO: 41) that render it resistant to targeting by an 820 interfering RNA. The coding sequence in SEQ ID NO: 42 starts at position 88 of SEQ ID NO: 42. In some embodiments, the recombinant rho gene being delivered can include the coding sequence of SEQ ID NO: 42 (e.g., starting at position 88 of SEQ ID NO: 42) but with a different upstream mRNA sequence. In some embodiments, a recombinant rho gene can have one or more other sequence modifications (either in addition to or as alternatives) to make it resistant to additional or alternative interfering RNAs (e.g., other interfering RNAs for which sequences are provided herein). In some embodiments, one or more interfering RNAs that target different regions of the endogenous rho coding sequence in a subject can be used.

```
SEQ ID NO: 42 (non-limiting example of a modified
"hardened" recombinant human rho gene):
CCAGCTGGAGCCCTGAGTGGCTGAGCTCAGGCCTTCGCAGCATTCTTGGG

TGGGAGCAGCCACGGGTCAGCCACAAGGGCCACAGCCATGAATGGCACAG

AAGGCCCTAACTTCTACGTGCCCTTCTCCAATGCGACGGGTGTGGTACGC

AGCCCCTTCGAGTACCCACAGTACTACCTGGCTGAGCCATGGCAGTTCTC

CATGCTGGCCGCCTACATGTTTCTGCTGATCGTGCTGGGCTTCCCCATCA

ACTTCCTCACGCTCTACGTCACCGTCCAGCACAAGAAGCTGCGCACGCCT

CTCAACTACATCCTGCTCAACCTAGCCGTGGCTGACCTCTTCATGGTCCT

AGGTGGCTTCACCAGCACCCTCTACACCTCTCTGCATGGATACTTCGTCT

TCGGGCCCACAGGATGCAATTTGGAGGGCTTCTTTGCCACCCTGGGCGGT

GAAATTGCCCTGTGGTCCTTGGTGGTCCTGGCCATCGAGCGGTACGTGGT

GGTGTGTAAGCCCATGAGCAACTTCCGCTTCGGGGAGAACCATGCCATCA

TGGGCGTTGCCTTCACCTGGGTCATGGCGCTGGCCTGCGCCGCACCCCCA

CTCGCCGGCTGGTCCAGGTACATCCCCGAGGGCCTGCAGTGCTCGTGTGG

AATCGACTACTACACGCTCAAGCCGGAGGTCAACAACGAGTCTTTTGTCA

TCTACATGTTCGTGGTCCACTTCACCATCCCCATGATTATCATCTTTTTC

TGCTATGGGCAGCTCGTCTTCACCGTCAAGGAGGCCGCTGCCCAGCAGCA

GGAGTCAGCCACCACACAGAAGGCAGAGAAGGAGGTCACCCGCATGGTCA

TCATCATGGTCATCGCTTTCCTGATCTGCTGGGTGCCCTACGCCAGCGTG

GCTTTTTATATATTCACCCACCAGGGCTCCAACTTCGGTCCCATCTTCAT

GACCATCCCAGCGTTCTTTGCCAAGAGCGCCGCCATCTACAACCCTGTCA

TCTATATCATGATGAACAAGCAGTTCCGGAACTGCATGCTCACCACCATC

TGCTGCGGCAAGAACCCACTGGGTGACGATGAGGCCTCTGCTACCGTGTC

CAAGACGGAGACGAGCCAGGTGGCCCCGGCCTAA
```

Accordingly, compositions herein can be administered to a subject in need of treatment. In some embodiments, the subject has or is suspected of having one or more conditions, diseases, or disorders of the brain and/or eye. In some embodiments, the subject has or is suspected of having one or more of the conditions, diseases, and disorders disclosed herein. In some embodiments, the subject has one or more endogenous mutant rho alleles (e.g., associated with or that cause a disease or disorder of the eye or retina). In some embodiments, the subject has at least one dominant mutant rho allele (e.g., that causes dominant retinitis pigmentosa). In some embodiments, the subject is a human. In some embodiments, the subject is a non-human primate. Non-limiting examples of non-human primate subjects include macaques (e.g., cynomolgus or rhesus macaques), marmosets, tamarins, spider monkeys, owl monkeys, vervet monkeys, squirrel monkeys, baboons, gorillas, chimpanzees, and orangutans. Other exemplary subjects include domesticated animals such as dogs and cats; livestock such as horses, cattle, pigs, sheep, goats, and chickens; and other animals such as mice, rats, guinea pigs, and hamsters.

In some embodiments, the dose of rAAV particles administered to a cell or a subject may be on the order ranging from $10^6$ to $10^{14}$ particles/mL or $10^3$ to $10^{15}$ particles/mL, or any values therebetween for either range, such as for example, about $10^6$, $10^7$, $10^8$, $10^9$, $10^{10}$, $10^{11}$, $10^{12}$, $10^{13}$, or $10^{14}$ particles/mL. In one embodiment, rAAV particles of higher than $10^{13}$ particles/mL are be administered. In some embodiments, the dose of rAAV particles administered to a subject may be on the order ranging from $10^6$ to $10^{14}$ vector genomes(vgs)/mL or $10^3$ to $10^{15}$ vgs/mL, or any values therebetween for either range, such as for example, about $10^6$, $10^7$, $10^8$, $10^9$, $10^{10}$, $10^{11}$, $10^{12}$, $10^{13}$, or $10^{14}$ vgs/mL. In one embodiment, rAAV particles of higher than $10^{13}$ vgs/mL are be administered. The rAAV particles can be administered as a single dose, or divided into two or more administrations as may be required to achieve therapy of the particular disease or disorder being treated. In some embodiments, 0.0001 mL to 10 mLs (e.g., 0.0001 mL, 0.001 mL, 0.01 mL, 0.1 mL, 1 mL, 10 mLs) are delivered to a subject in a dose.

In some embodiments, rAAV viral titers range from $1\times10^{10}$-$5\times10^{13}$ vg/ml. In some embodiments, rAAV viral titers can be $1\times10^{10}$, $2.5\times10^{10}$, $5\times10^{10}$, $1\times10^{11}$, $2.5\times10^{11}$, $5\times10^{11}$, $1\times10^{12}$, $2.5\times10^{12}$, $5\times10^{12}$, $1\times10^{13}$, $2.5\times10^{13}$, or $5\times10^{13}$ vg/mL. In some embodiments, viral titers are less than $1\times10^{10}$ vg/mL. In some embodiments, rAAV viral titers are greater than $1\times10^{15}$ vg/mL. In one embodiment, rAAV particles are greater than $5\times10^{13}$ vgs/mL. In some embodiments, rAAV viral titers are administered via methods further described herein (e.g., subretinally or intravitreally).

The rAAV particles can be administered as a single dose, or divided into two or more administrations as may be required to achieve therapy of the particular disease or disorder being treated. In some embodiments, from 1 to 500 microliters of a composition described in this application is administered to one or both eyes of a subject. For example, in some embodiments, about 1, about 10, about 50, about 100, about 200, about 300, about 400, or about 500 microliters can be administered to each eye. However, it should be appreciated that smaller or larger volumes could be administered in some embodiments.

In some embodiments, the disclosure provides formulations of one or more rAAV-based compositions disclosed herein in pharmaceutically acceptable solutions for administration to a cell or an animal, either alone or in combination with one or more other modalities of therapy, and in particular, for therapy of human cells, tissues, and diseases affecting man.

If desired, rAAV particle or nucleic acid vectors may be administered in combination with other agents as well, such as, e.g., proteins or polypeptides or various pharmaceutically-active agents, including one or more systemic or topical administrations of therapeutic polypeptides, biologically active fragments, or variants thereof. In fact, there is virtually no limit to other components that may also be included, given that the additional agents do not cause a significant adverse effect upon contact with the target cells or host tissues. The rAAV particles may thus be delivered along with various other agents as required in the particular instance. Such compositions may be purified from host cells or other biological sources, or alternatively may be chemically synthesized as described herein.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, intra-articular, and intramuscular administration and formulation.

Typically, these formulations may contain at least about 0.1% of the therapeutic agent (e.g., rAAV particle or host cell) or more, although the percentage of the active ingredient(s) may, of course, be varied and may conveniently be between about 1 or 2% and about 70% or 80% or more of the weight or volume of the total formulation. Naturally, the amount of therapeutic agent(s) (e.g., rAAV particle) in each therapeutically-useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver an rAAV particle or host cell in suitably formulated pharmaceutical compositions disclosed herein either subcutaneously, intraocularly, intravitreally, parenterally, subcutaneously, intravenously, intracerebro-ventricularly, intramuscularly, intrathecally, orally, intraperitoneally, by oral or nasal inhalation, or by direct injection to one or more cells, tissues, or organs by direct injection.

The pharmaceutical forms of the rAAV particle or host cell compositions suitable for injectable use include sterile aqueous solutions or dispersions. In some embodiments, the form is sterile and fluid to the extent that easy syringability exists. In some embodiments, the form is stable under the conditions of manufacture and storage and is preserved against the contaminating action of microorganisms, such as bacteria and fungi. The carrier can be a solvent or dispersion medium containing, for example, water, saline, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

The term "carrier" refers to a diluent, adjuvant, excipient, or vehicle with which the rAAV particle or host cell is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers.

The compositions of the present disclosure can be administered to the subject being treated by standard routes including, but not limited to, pulmonary, intranasal, oral, inhalation, parenteral such as intravenous, topical, transdermal, intradermal, transmucosal, intraperitoneal, intramuscular, intracapsular, intraorbital, intravitreal, intracardiac, transtracheal, subcutaneous, subcuticular, intraarticular, subcapsular, subarachnoid, intraspinal, epidural and intrasternal injection.

The compositions of the present disclosure can be delivered to the eye through a variety of routes. They may be delivered intraocularly, by topical application to the eye or by intraocular injection into, for example the vitreous (intravitreal injection) or subretinal (subretinal injection) interphotoreceptor space. In some embodiments, they are delivered to rod photoreceptor cells. Alternatively, they may be delivered locally by insertion or injection into the tissue surrounding the eye. They may be delivered systemically through an oral route or by subcutaneous, intravenous or intramuscular injection. Alternatively, they may be delivered by means of a catheter or by means of an implant, wherein such an implant is made of a porous, non-porous or gelatinous material, including membranes such as silastic membranes or fibers, biodegradable polymers, or proteinaceous material. They can be administered prior to the onset of the condition, to prevent its occurrence, for example, during surgery on the eye, or immediately after the onset of the pathological condition or during the occurrence of an acute or protracted condition.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, intravitreal, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by, e.g., FDA Office of Biologics standards.

Sterile injectable solutions are prepared by incorporating the rAAV particles or host cells in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The amount of rAAV particle, nucleic acid vector, or host cell compositions and time of administration of such compositions will be within the purview of the skilled artisan having benefit of the present teachings. It is likely, however, that the administration of therapeutically-effective amounts of the disclosed compositions may be achieved by a single administration, such as for example, a single injection of sufficient numbers of infectious particles to provide therapeutic benefit to the patient undergoing such treatment. Alternatively, in some circumstances, it may be desirable to provide multiple, or successive administrations of the rAAV particle or host cell compositions, either over a relatively short, or a relatively prolonged period of time, as may be determined by the medical practitioner overseeing the administration of such compositions.

In some embodiments, rod cells remain structurally intact and/or viable upon silencing of cellular rhodopsin gene expression. In some embodiments, rods cells in which cellular rhodopsin gene expression is silenced have shortened outer segments which would normally contain rhodopsin. In some embodiments, the length of the outer segments can be maintained or restored (e.g., partially or completely) using the exogenously added (hardened) rhodopsin gene, the expression of which is resistant to silencing using the compositions described in this application.

The composition may include rAAV particles or host cells, either alone, or in combination with one or more additional active ingredients, which may be obtained from natural or recombinant sources or chemically synthesized. In some embodiments, rAAV particles are administered in combination, either in the same composition or administered as part of the same treatment regimen, with a proteasome inhibitor, such as Bortezomib, or hydroxyurea.

To "treat" a disease as the term is used herein, means to reduce the frequency or severity of at least one sign or symptom of a disease or disorder experienced by a subject. The compositions described above are typically administered to a subject in an effective amount, that is, an amount capable of producing a desirable result. The desirable result will depend upon the active agent being administered. For example, an effective amount of a rAAV particle may be an amount of the particle that is capable of transferring a heterologous nucleic acid to a host organ, tissue, or cell.

Toxicity and efficacy of the compositions utilized in methods of the disclosure can be determined by standard pharmaceutical procedures, using either cells in culture or experimental animals to determine the LD50 (the dose lethal to 50% of the population). The dose ratio between toxicity and efficacy the therapeutic index and it can be expressed as the ratio LD50/ED50. Those compositions that exhibit large therapeutic indices are preferred. While those that exhibit toxic side effects may be used, care should be taken to design a delivery system that minimizes the potential damage of such side effects. The dosage of compositions as described herein lies generally within a range that includes an ED50 with little or no toxicity. The dosage may vary within this range depending upon the dosage form employed and the route of administration utilized.

Aspects of the disclosure relate to recombinant adeno-associated virus (rAAV) particles for delivery of one or more nucleic acid vectors comprising a gene of interest into various tissues, organs, and/or cells. In some embodiments, the rAAV particles comprise an rAAV capsid protein as described herein, e.g., comprising one or more amino acid substitutions. In some embodiments, the gene of interest encodes a polypeptide or protein of interest (e.g., a therapeutic polypeptide or protein). In some embodiments, the gene of interest encodes an RNA of interest (e.g., a therapeutic mRNA, siRNA, shRNA, microRNA, antisense RNA, tRNA, rRNA, or a ribozyme). In some embodiments, a gene of interest is a replacement gene (e.g., an eye-specific gene, a functional gene, a functional RHO gene). In some embodiments, a gene of interest comprises or encodes an RNA of interest (e.g., microRNA, siRNA, shRNA) and a replacement gene of interest (e.g., an eye-specific gene, a functional gene, a functional RHO gene). In some embodiments, a functional RHO gene comprises an RHO gene comprising silent nucleotide substitutions that render it incapable of being degraded by an RNA of interest (e.g., microRNA, siRNA, shRNA). In some embodiments, an RNA of interest and a replacement gene of interest are under the control of the same promoter. In some embodiments, an RNA of interest and a replacement gene of interest are under the control of separate promoters. Any suitable promoters can be used, for example, but not limited to a viral promoter (e.g., a CMV or other viral promoter), a microbial (e.g., a yeast or bacterial), or a eukaryotic (e.g., a mammalian) promoter.

Recombinant AAV (rAAV) particles may comprise at a minimum (a) one or more heterologous nucleic acid regions comprising a sequence encoding a gene of interest (e.g., an RNA of interest and/or a replacement gene of interest) and (b) one or more regions comprising inverted terminal repeat (ITR) sequences (e.g., wild-type ITR sequences or engineered ITR sequences) flanking the one or more heterologous nucleic acid regions. In some embodiments, the nucleic acid vector is between 4 kb and 5 kb in size (e.g., 4.2 to 4.7 kb in size). This nucleic acid vector may be encapsidated by a viral capsid, such as an AAV1, AAV2, AAV3, AAV4, or AAV5 capsid, which may comprise a modified capsid protein as described herein. In some embodiments, the nucleic acid vector is circular. In some embodiments, the nucleic acid vector is single-stranded. In some embodiments, the nucleic acid vector is double-stranded. In some embodiments, a double-stranded nucleic acid vector may be, for example, a self-complementary vector that contains a region of the nucleic acid vector that is complementary to another region of the nucleic acid vector, initiating the formation of the double-strandedness of the nucleic acid vector.

The rAAV particle may be of any AAV serotype, including any derivative or pseudotype (e.g., 1, 2, 3, 4, 5, 6, 7, 8, 9, 10, 2/1, 2/5, 2/8, or 2/9). As used herein, the serotype of an rAAV viral vector (e.g., an rAAV particle) refers to the serotype of the capsid proteins of the recombinant virus. In some embodiments, the rAAV particle is not AAV2. In some embodiments, the rAAV particle is AAV2. In some embodiments, the rAAV particle is AAV6. In some embodiments, the rAAV particle is an AAV6 serotype comprising an rAAV capsid protein as described herein. Non-limiting examples of derivatives and pseudotypes include rAAV2/1, rAAV2/5, rAAV2/8, rAAV2/9, AAV2-AAV3 hybrid, AAVrh.10, AAVhu.14, AAV3a/3b, AAVrh32.33, AAV-HSC15, AAV-HSC17, AAVhu.37, AAVrh.8, CHt-P6, AAV2.5, AAV6.2, AAV2i8, AAV-HSC15/17, AAVM41, AAV9.45, AAV6 (Y445F/Y731F), AAV2.5T, AAV-HAE1/2, AAV clone 32/83, AAVShH10, AAV2 (Y→F), AAV8 (Y733F), AAV2.15, AAV2.4, AAVM41, and AAVr3.45. Such AAV serotypes and derivatives/pseudotypes, and methods of producing such derivatives/pseudotypes are known in the art (see, e.g., Mol Ther. 2012 April; 20(4):699-708. doi: 10.1038/mt.2011.287. Epub 2012 Jan. 24. The AAV vector toolkit: poised at the clinical crossroads. Asokan A1, Schaffer D V, Samulski R J.). In some embodiments, the rAAV particle is a pseudotyped rAAV particle, which comprises (a) a nucleic acid vector comprising ITRs from one serotype (e.g., AAV2) and (b) a capsid comprised of capsid proteins derived from another serotype (e.g., AAV1, AAV3, AAV4, AAV5, AAV6, AAV7, AAV8, AAV9, or AAV10). Methods for producing and using pseudotyped rAAV vectors are known in the art (see, e.g., Duan et al., J. Virol., 75:7662-7671, 2001; Halbert et al., J. Virol., 74:1524-1532, 2000; Zolotukhin et al., Methods, 28:158-167, 2002; and Auricchio et al., Hum. Molec. Genet., 10:3075-3081, 2001).

Methods of producing rAAV particles and nucleic acid vectors are also known in the art and commercially available (see, e.g., Zolotukhin et al. Production and purification of serotype 1, 2, and 5 recombinant adeno-associated viral vectors. Methods 28 (2002) 158-167; and U.S. Patent Publication Numbers US20070015238 and US20120322861, which are incorporated herein by reference; and plasmids and kits available from ATCC and Cell Biolabs, Inc.). For example, a plasmid containing the nucleic acid vector may be combined with one or more helper plasmids, e.g., that contain a rep gene (e.g., encoding Rep78, Rep68, Rep52 and Rep40) and a cap gene (e.g., encoding VP1, VP2, and VP3, including a modified VP3 region as described herein), and transfected into a producer cell line such that the rAAV particle can be packaged and subsequently purified.

In some embodiments, the one or more helper plasmids include a first helper plasmid comprising a rep gene and a cap gene (e.g., encoding a rAAV capsid protein as described herein) and a second helper plasmid comprising a E1a gene, a E1b gene, a E4 gene, a E2a gene, and a VA gene. In some embodiments, the rep gene is a rep gene derived from AAV2 or AAV6 and the cap gene is derived from AAV2 or AAV6 and may include modifications to the gene in order to produce the modified capsid protein described herein. Helper plasmids, and methods of making such plasmids, are known in the art and commercially available (see, e.g., pDM, pDG, pDP1rs, pDP2rs, pDP3rs, pDP4rs, pDP5rs, pDP6rs, pDG(R484E/R585E), and pDP8.ape plasmids from PlasmidFactory, Bielefeld, Germany; other products and services available from Vector Biolabs, Philadelphia, Pa.; Cellbiolabs, San Diego, Calif.; Agilent Technologies, Santa Clara, Ca.; and Addgene, Cambridge, Mass.; pxx6; Grimm et al. (1998), Novel Tools for Production and Purification of Recombinant Adenoassociated Virus Vectors, Human Gene Therapy, Vol. 9, 2745-2760; Kern, A. et al. (2003), Identification of a Heparin-Binding Motif on Adeno-Associated Virus Type 2 Capsids, Journal of Virology, Vol. 77, 11072-11081; Grimm et al. (2003), Helper Virus-Free, Optically Controllable, and Two-Plasmid-Based Production of Adeno-associated Virus Vectors of Serotypes 1 to 6, Molecular Therapy, Vol. 7, 839-850; Kronenberg et al. (2005), A Conformational Change in the Adeno-Associated Virus Type 2 Capsid Leads to the Exposure of Hidden VP1 N Termini, Journal of Virology, Vol. 79, 5296-5303; and Moullier, P. and Snyder, R. O. (2008), International efforts for recombinant adeno-associated viral vector reference standards, Molecular Therapy, Vol. 16, 1185-1188).

An exemplary, non-limiting, rAAV particle production method is described next. One or more helper plasmids are produced or obtained, which comprise rep and cap ORFs for the desired AAV serotype and the adenoviral VA, E2A (DBP), and E4 genes under the transcriptional control of their native promoters. The cap ORF may also comprise one or more modifications to produce a modified capsid protein as described herein. HEK293 cells (available from ATCC®) are transfected via CaPO4-mediated transfection, lipids or polymeric molecules such as Polyethylenimine (PEI) with the helper plasmid(s) and a plasmid containing a nucleic acid vector described herein. The HEK293 cells are then incubated for at least 60 hours to allow for rAAV particle production. Alternatively, in another example Sf9-based producer stable cell lines are infected with a single recombinant baculovirus containing the nucleic acid vector. As a further alternative, in another example HEK293 or BHK cell lines are infected with a HSV containing the nucleic acid vector and optionally one or more helper HSVs containing rep and cap ORFs as described herein and the adenoviral VA, E2A (DBP), and E4 genes under the transcriptional control of their native promoters. The HEK293, BHK, or Sf9 cells are then incubated for at least 60 hours to allow for rAAV particle production. The rAAV particles can then be purified using any method known the art or described herein, e.g., by iodixanol step gradient, CsCl gradient, chromatography, or polyethylene glycol (PEG) precipitation.

The disclosure also contemplates host cells that comprise at least one of the disclosed rAAV particles or nucleic acid vectors. Such host cells include mammalian host cells, with human host cells being preferred, and may be either isolated, in cell or tissue culture. In the case of genetically modified animal models (e.g., a mouse), the transformed host cells may be comprised within the body of a non-human animal itself. In some embodiments, the host cell is a cell of erythroid lineage, such as a $CD36^+$ burst-forming units-erythroid (BFU-E) cell or a colony-forming unit-erythroid (CFUE-E) progenitor cell.

In some embodiments, compositions described herein (e.g., siRNA, shRNA, and/or replacement genes of interest) are formulated in a nanoparticle. In some embodiments, compositions described herein (e.g., siRNA, shRNA, and/or replacement genes of interest) are formulated in a lipid nanoparticle. In some embodiments, compositions described herein (e.g., siRNA, shRNA, and/or replacement genes of interest) are formulated in a lipid-polycation complex, referred to as a cationic lipid nanoparticle. The formation of the lipid nanoparticle may be accomplished by methods known in the art and/or as described in U.S. Pub. No. 20120178702, herein incorporated by reference in its entirety. As a non-limiting example, the polycation may include a cationic peptide or a polypeptide such as, but not limited to, polylysine, polyornithine and/or polyarginine and the cationic peptides described in International Pub. No. WO2012013326 or US Patent Pub. No. US20130142818; each of which is herein incorporated by reference in its entirety. In some embodiments, compositions described herein (e.g., siRNA, shRNA, and/or replacement genes of interest) are formulated in a lipid nanoparticle that includes a non-cationic lipid such as, but not limited to, cholesterol or dioleoyl phosphatidylethanolamine (DOPE).

EXAMPLES

Example 1: Identification of Short Interfering RNA (siRNA) that Knockdown RHO

Figure 1B:
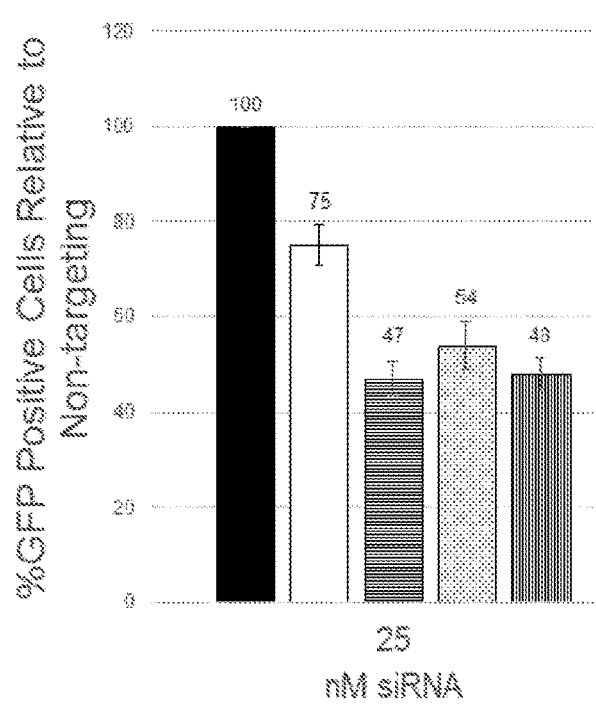
Figure 1C:
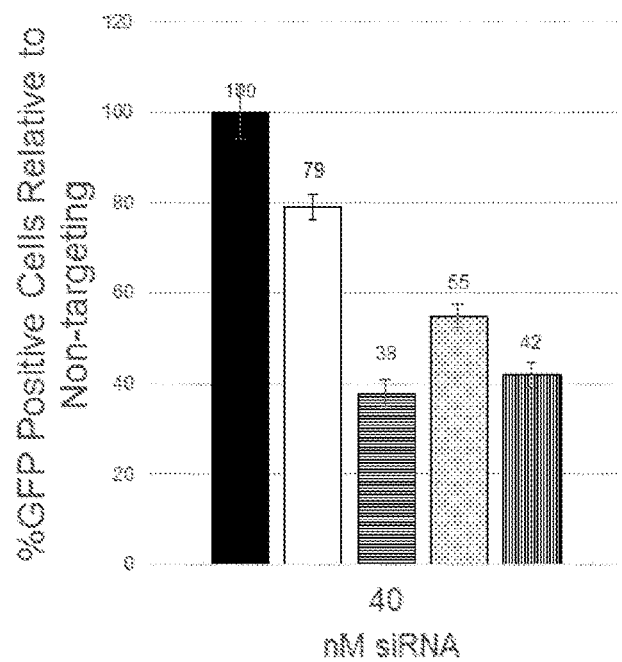
Figure 11:
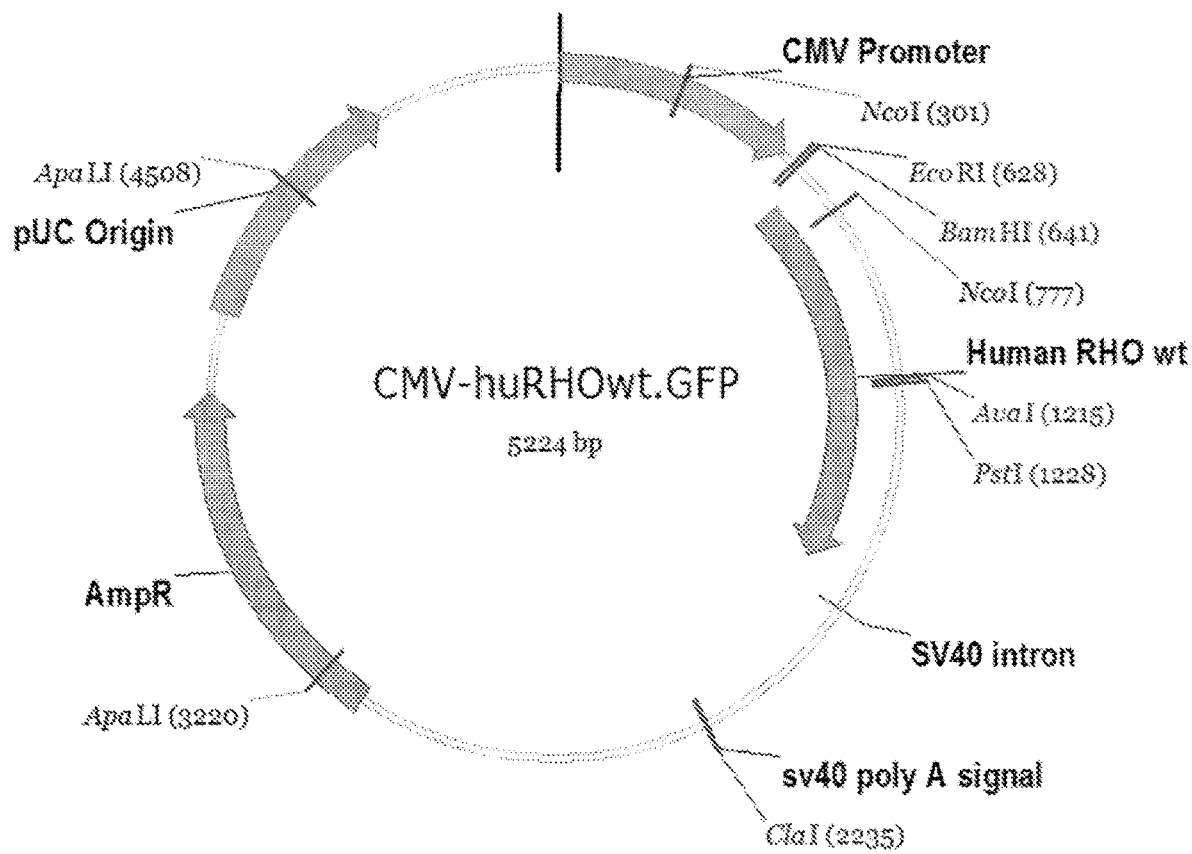
FIG. 11 depicts an exemplary map of a plasmid encoding GFP-tagged human RHO.

Using the short interfering RNA (siRNA) design principles described by Khvorova and colleagues[4, 5], 14 siRNA were designed to cleave dog siRNA specifically, 12 of which also target the human mRNA for rhodopsin. Before proceeding, the NCBI Blast utility (blast.ncbi.nlm.nih.gov/Blast.cgi) was used to screen positions 2 through 19 of the siRNAs against the NCBI human RefSeq database. Two of the potential siRNA were excluded because they had close matches with other genes that might be expressed in the retina. RNA versions of 10 of the siRNAs were ordered from GE Healthcare Dharmacon together with a non-targeting siRNA to use as a control. These were tested in cells expressing human RHO fused to green fluorescent protein (GFP, exemplary plasmid map depicted in FIG. 11), and reduction in green fluorescent cells was measured by fluorescence activated cell sorting (FACS). The rationale was that cleavage of RHO mRNA would reduce the production of GFP. While all of the siRNAs were designed based on current design principles for siRNAs, only 3 of 10 that were tested led to reduction of 30% or more (FIG. 1A-C).

Figure 2:
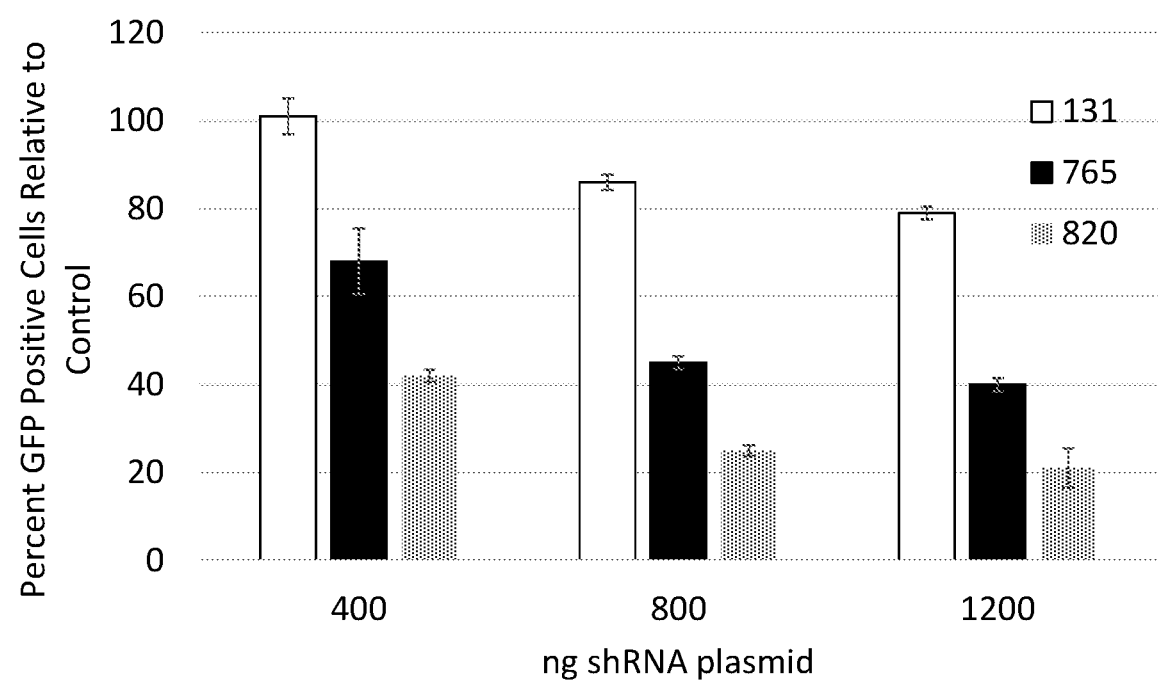
FIG. 2 shows RHO knockdown by shRNA. This experiment was performed in 293T cells with three biologic replicates. 200 ng of GFP-tagged human rhodopsin was co-transfected with pUC57 containing either shRNA 131, 765, or 820 driven by the H1 promoter. Samples were incubated for 72 hours and RHO knockdown measured by flow cytometry as in FIG. 1.

To confirm that these siRNAs would be effective as small hairpin RNAs expressed from an RNA polymerase III promoter and delivered by AAV, the DNA sequences for shRNAs were cloned expressing three of the siRNAs (FIG. 2). Interestingly, the relative knockdown of RHO using siRNA did not exactly predict relative suppression of RHO using shRNA, since siRNA 131 (SEQ ID NO: 1) was the most effective siRNA, but the least effective of the shRNAs that were tested. Simple transfection of siRNAs as RNA may not exactly predict the effectiveness of shRNA designed to produce the same siRNAs by transcription and processing.

Figure 3:
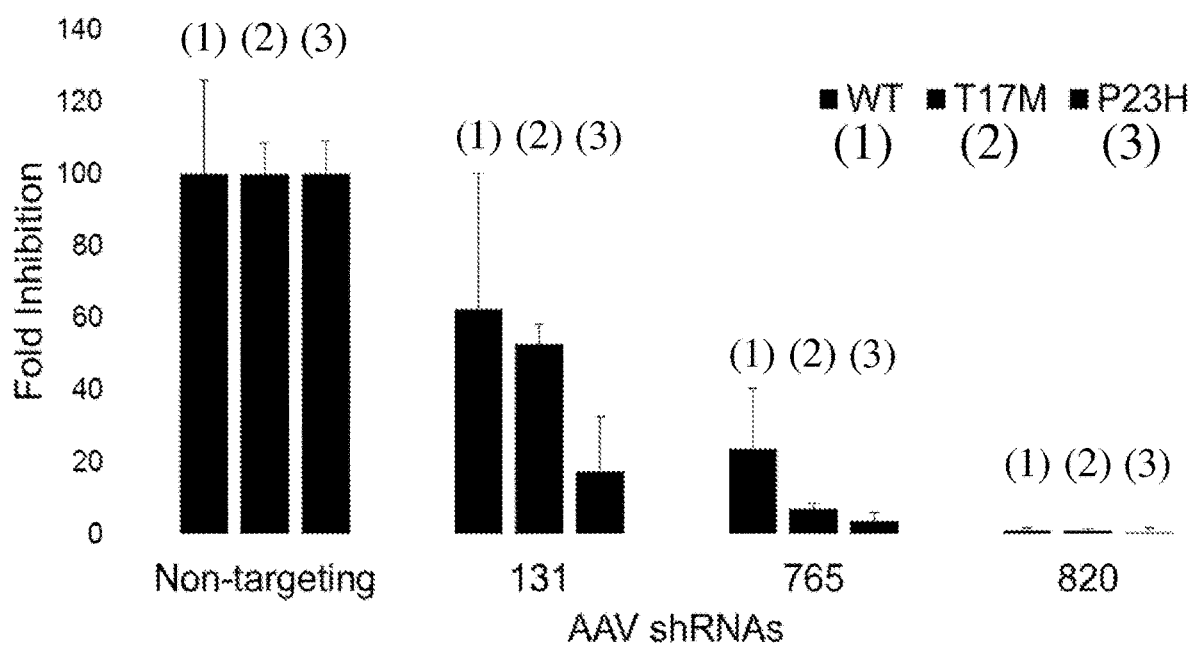
FIG. 3 shows that shRNAs cleave both mutant and wild type RHO RNA. This experiment was performed in 293T cells with two biologic replicates and three qRT-PCR replicates. 200 ng of GFP-tagged human rhodopsin (WT, T17M or P23H) was co-transfected with rAAV-H1-shRNA plasmids (131 (SEQ ID NO: 11), 765 (SEQ ID NO: 15), or 820 (SEQ ID NO: 17)) utilizing LIPOFECTAMINE® 2000. The Non-Targeting shRNA was designed to degrade an unrelated phototransduction protein, a subunit of the rod cyclic GMP gated ion channel. Samples were incubated for 48 hours then processed for qRT-PCR analysis.

To confirm that the shRNAs would be effective in cleaving both wild type (normal) and mutant RHO, the same three shRNA cloned in an AAV vector were tested for their ability to digest wild type and two different mutant RHO mRNAs using quantitative reverse transcription PCR (qRT-PCR) as an assay (FIG. 3).

Table 5 lists RNA sequences corresponding to shRNA sequences identified as capable of cleaving RHO, including the sense strand, loop, antisense strand, and overhang. Each sequence is depicted with two alternative loop sequences that are bolded and underlined for emphasis, with overhangs italicized and underlined for emphasis.

The non-limiting examples of AAV2/5-sc-H1-shRNA constructs described herein can also be referred to as AAV2/5-sc-MOP500 rGFP-shRNA constructs. The AAV2/5 indicates that the nucleic acid encoding the shRNA is flanked by AAV2 ITRs and provided in an rAAV particle comprising AAV5 capsid proteins. In some embodiments, any interfering RNA described herein and any recombinant RHO gene described herein can be provided on the same AAV nucleic acid (e.g., flanked by AAV2 ITRs) in an rAAV particle (e.g., comprising AAV5 capsid proteins). In some embodiments, any interfering RNA described herein and any recombinant RHO gene described herein can be provided on different AAV nucleic acids (e.g., each flanked by AAV2 ITRs, or each flanked by ITRs from different AAV serotypes)

TABLE 5

Small hairpin RNA (shRNA)

Figure 4:
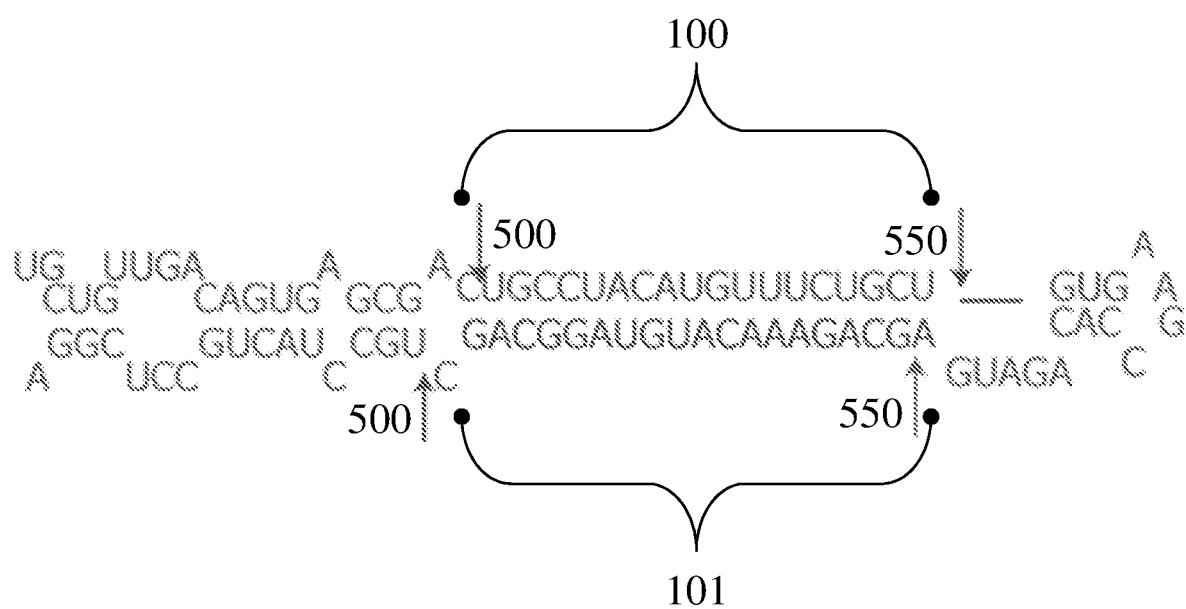
FIG. 4 shows siRNA131 sense (SEQ ID NO: 1) and antisense (SEQ ID NO: 2) strands in the sequence context of miR30 (SEQ ID NO: 28). After expression from an RNA polymerase II promoter, the siRNA will be excised from the precursor by the enzyme Drosha in the nucleus and Dicer in the cytoplasm.

| SEQ ID NO: | Name | RNA sequence (Sense Strand-Loop-Antisense Strand-Overhang) |
|---|---|---|
| 20 | RHO131-9 | CUGCCUACAUGUUUCUGCUUCAAGAGAGCAGAAACAUGUAGGCAG_UU_ |
| 21 | RHO131-10 | CUGCCUACAUGUUUCUGCUUGUGCUUAGCAGAAACAUGUAGGCAG_UU_ |
| 22 | RHO134-9 | CCUACAUGUUUCUGCUGAUUCAAGAGAUCAGCAGAAACAUGUAGG_UU_ |
| 23 | RHO134-10 | CCUACAUGUUUCUGCUGAUUGUGCUUAUCAGCAGAAACAUGUAGG_UU_ |
| 24 | RHO765-9 | GCAUGGUCAUCAUCAUGGUUCAAGAGACCAUGAUGAUGACCAUGC_UU_ |
| 25 | RHO765-10 | GCAUGGUCAUCAUCAUGGUUGUGCUUACCAUGAUGAUGACCAUGC_UU_ |
| 26 | RHO820-9 | GUGGCAUUCUACAUCUUCAUCAAGAGUGAAGAUGUAGAAUGCCAC_UU_ |
| 27 | RHO820-10 | GUGGCAUUCUACAUCUUCAUGUGCUUUGAAGAUGUAGAAUGCCAC_UU_ | siRNAs can also be delivered as artificial microRNAs[7] of a structure like that in FIG. 4. The exemplary microRNA of FIG. 4 comprises sense (100) and antisense (101) strands of RHO131 (SEQ ID NOs: 1 and 2, respectively). The advantage of this mode of expression is that production of the siRNA can be made cell type specific through the use of a specific promoter sequence. In this case the proximal promoter of the human rhodopsin gene or the human rhodopsin kinase promoter would be used to restrict expression to photoreceptor cells.

Example 2: Analysis of RHO KD in RHO+/+ Dogs

Dog 2190 (rcd1 carrier) received subretinal injections of AAV2/5-sc-H1-shRNA-Rho131 at the concentrations listed in Table 6. The dog was terminated 8 weeks post injection. Several 3 mm neuroretinal biopsy punches were collected from each eye from both bleb and non-bleb regions.

encapsidated in different rAAV particles (e.g., each comprising AAV5 capsid proteins, or each having capsid proteins from different AAV serotypes).

Western Blot Analysis:

Two biopsy punches from each eye, representing either bleb or non-bleb regions, were incubated in 50 µl of Lewin buffer solution A (with protease inhibitors) for 15 minutes on ice. The samples were sonicated at 40% amplitude, 15 secON/10 secOFF×8 pulses. Samples were then centrifuged and the pellet discarded. Protein concentration in the supernatant was measured by Bradford method. 1 µg of total protein was immunoblotted to visualize rhodopsin (antibody used: Millipore MAB5356, diluted 1:1000 in ODYSSEY® blocking buffer), and anti-histone antibody (Abcam ab1791, diluted 1:3000) was used as a loading control (FIG. 5A) and to normalize the signals (FIG. 5B). Comparison between RHO protein amounts between bleb and non-bleb regions were not consistent with the experimental design (FIG. 5C).

TABLE 6

Dog 2190

| Dog | Genotype | Sex | DOB | Age at injection | Right Eye (OD) | Left Eye (OS) |
|---|---|---|---|---|---|---|
| 2190 | rcd1 carrier | M | Aug. 11, 2014 | 1 year | AAV2/5-sc-H1-shRNA-Rho131 Ω4063 5E+12 vg/ml 150 µl SR | AAV2/5-sc-H1-shRNA-Rho131 Ω4063 1E+12 vg/ml 150 µl SR |

Figures 6A, 6B:
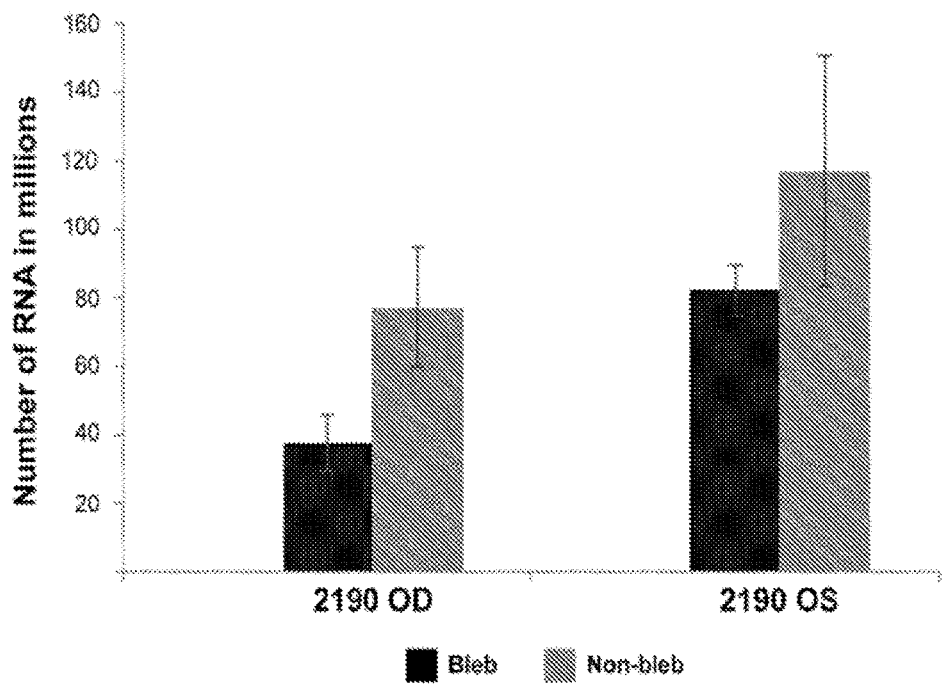
FIGS. 6A-6B show the absolute numbers of canine RHO RNA.

Absolute Quantitation of Canine Rhodopsin RNA in Canine Retina:

In order to determine the absolute amounts of rhodopsin RNA present in the retina after ribozyme-treatment, absolute quantitation was performed using Q-PCR Standard Curve method. Dilution series of known quantities of canine RHO cDNA was used to construct a standard curve. Total amount of canine RHO RNA in each sample was calculated based on this standard curve (FIG. 6A).

Partial knockdown of canine RHO is seen with AAV2/5-sc-H1-shRNA-Rho131. At the highest concentration used, protein levels are decreased by 37%, whereas RNA is decreased by nearly 50% (FIG. 6B).

Example 3: Further Analysis of RHO KD in RHO$^{+/+}$ Dogs

Dog 2194 (rcd1 carrier) received subretinal injections of AAV2/5-sc-H1-shRNA-Rho820 at the concentrations listed in Table 7. The dog was terminated 8 weeks post injection. Several 3 mm neuroretinal biopsy punches were collected from each eye from both bleb and non-bleb regions.

TABLE 7

Dog 2194

| Dog | Genotype | Sex | DOB | Age at injection | Right Eye (OD) | Left Eye (OS) |
|---|---|---|---|---|---|---|
| 2194 | rcd1 carrier | F | Aug. 11, 2014 | 1 year | AAV2/5-sc-H1-shRNA-Rho820 Ω4064 5E+12 vg/ml 150 μl SR 50 μl intravitr | AAV2/5-sc-H1-shRNA-Rho820 Ω4064 1E+12 vg/ml Small bleb 50 μl SR 250 μl intravitr |

Western Blot Analysis:

Two biopsy punches from each eye, representing either bleb or non-bleb regions, were incubated in 50 μl of Lewin buffer solution A (with protease inhibitors) for 15 minutes on ice. The samples were sonicated at 40% amplitude, 15 secON/10 secOFF×8 pulses. Samples were then centrifuged and the pellet discarded. Protein concentration in the supernatant was measured by Bradford method. 1 μg of total protein was immunoblotted to visualize rhodopsin (antibody used: Millipore MAB5356, diluted 1:1000 in ODYSSEY® blocking buffer). Anti-histone antibody (Abcam ab1791, diluted 1:3000) was used as a loading control (FIG. 7A) and to normalize the signals (FIG. 7B). Comparison between RHO protein amounts between bleb and non-bleb regions were not consistent with the experimental design (FIG. 7C).

Absolute Quantitation of Canine Rhodopsin RNA in Canine Retina:

In order to determine the absolute amounts of rhodopsin RNA present in the retina after ribozyme-treatment, absolute quantitation was performed using Q-PCR Standard Curve method. Dilution series of known quantities of canine RHO cDNA was used to construct a standard curve. Total amount of canine RHO RNA in each sample was calculated based on this standard curve (FIG. 8A).

Figures 8A, 8B:
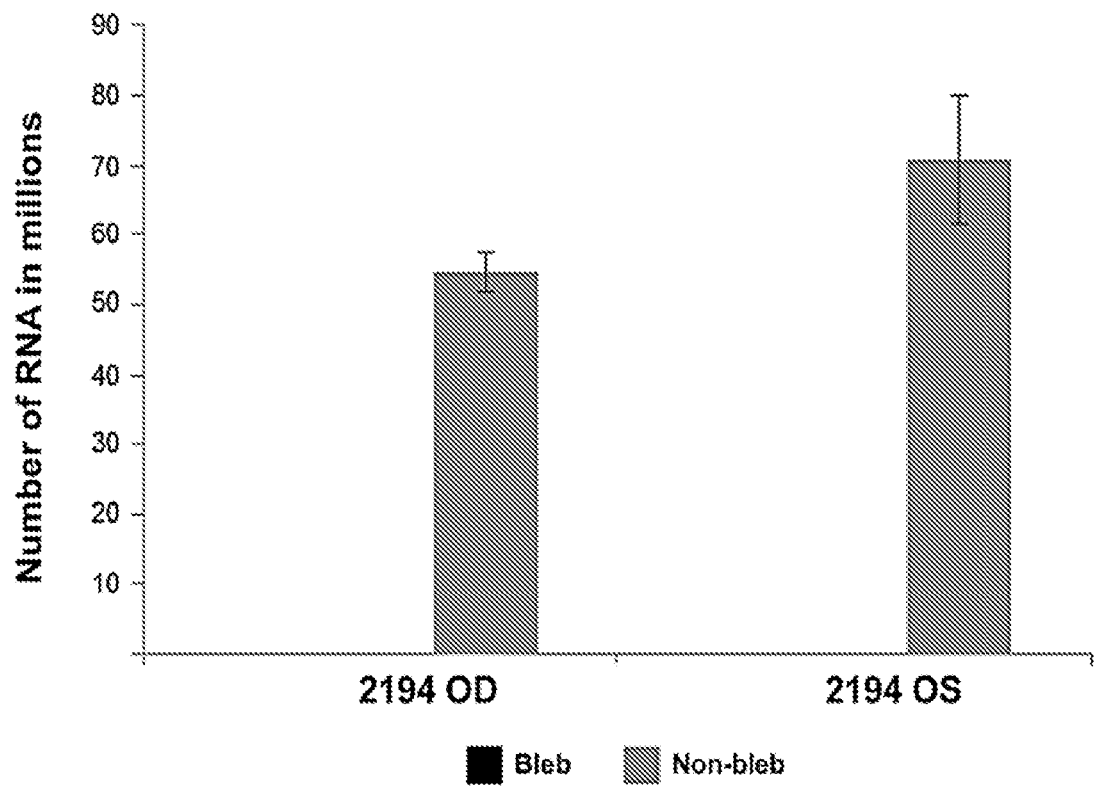
FIGS. 8A-8B show the absolute numbers of canine RHO RNA.

Complete knockdown of canine RHO RNA and protein is seen with AAV2/5-sc-H1-shRNA-Rho820 even at the lower dose of 1×10$^{12}$ vg/ml (FIG. 8B).

Example 4: Hardened mRNA Sequences for Replacement Gene

Figure 10:
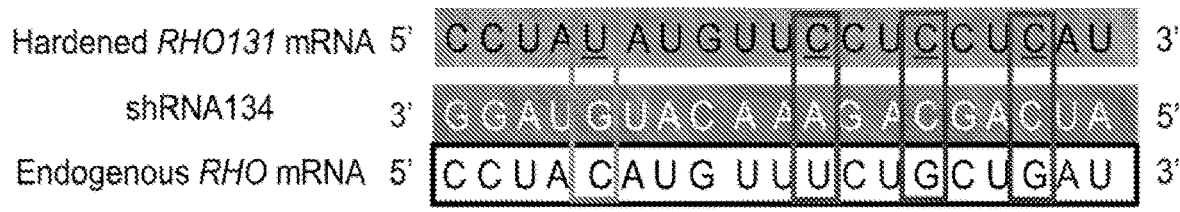
FIG. 10 depicts exemplary base pairing that occurs between shRNA134 and the target sequence of endogenous human or hardened RHO131 mRNA. The proximity of the target sequences of shRNAs 131 and 134 enables the same hardened RHO131 to be employed. Dark gray box: a weak wobble base pairing that occurs in RNA between guanosine and uracil. Light gray box: mismatch between shRNA and hardened RHO mRNA only. Sequences correspond to SEQ ID NOs: 38-40 from top to bottom, respectively.

In some embodiments, an mRNA for a replacement gene (e.g., replacement RHO) can be modified at one or more positions to "harden" it (i.e., to make it resistant to degradation by siRNA). In some embodiments, one or more silent nucleotide substitutions can be included in the replacement gene relative to the siRNA that is provided to knockdown the endogenous gene (e.g., RHO gene). FIGS. 9 and 10 provide non-limiting examples of nucleotide substitutions that can be introduced into the replacement RHO mRNA. It should be appreciated that a replacement RHO gene can include one or more of these substitutions.

FIG. 9 depicts a representation of base pairing that occurs between each shRNA and the target sequence of endogenous human or hardened RHO mRNA. All shRNAs base-pair perfectly with the target sequence of RHO mRNA of dog. White box: mismatch between shRNA and endogenous dog as well as hardened RHO mRNA. Dark gray box: a weak wobble base pairing that occurs in RNA between guanosine and uracil. Light gray box: mismatch between shRNA and hardened RHO mRNA only.

FIG. 10 depicts a representation of base pairing that occurs between shRNA134 and the target sequence of endogenous human or hardened RHO131 mRNA. The proximity of the target sequences of shRNAs 131 and 134 enables the same hardened RHO131 to be employed. Dark gray box: a weak wobble base pairing that occurs in RNA between guanosine and uracil. Light gray box: mismatch between shRNA and hardened RHO mRNA only.

Example 5: Encoding siRNA and Replacement Genes

Figure 12A:
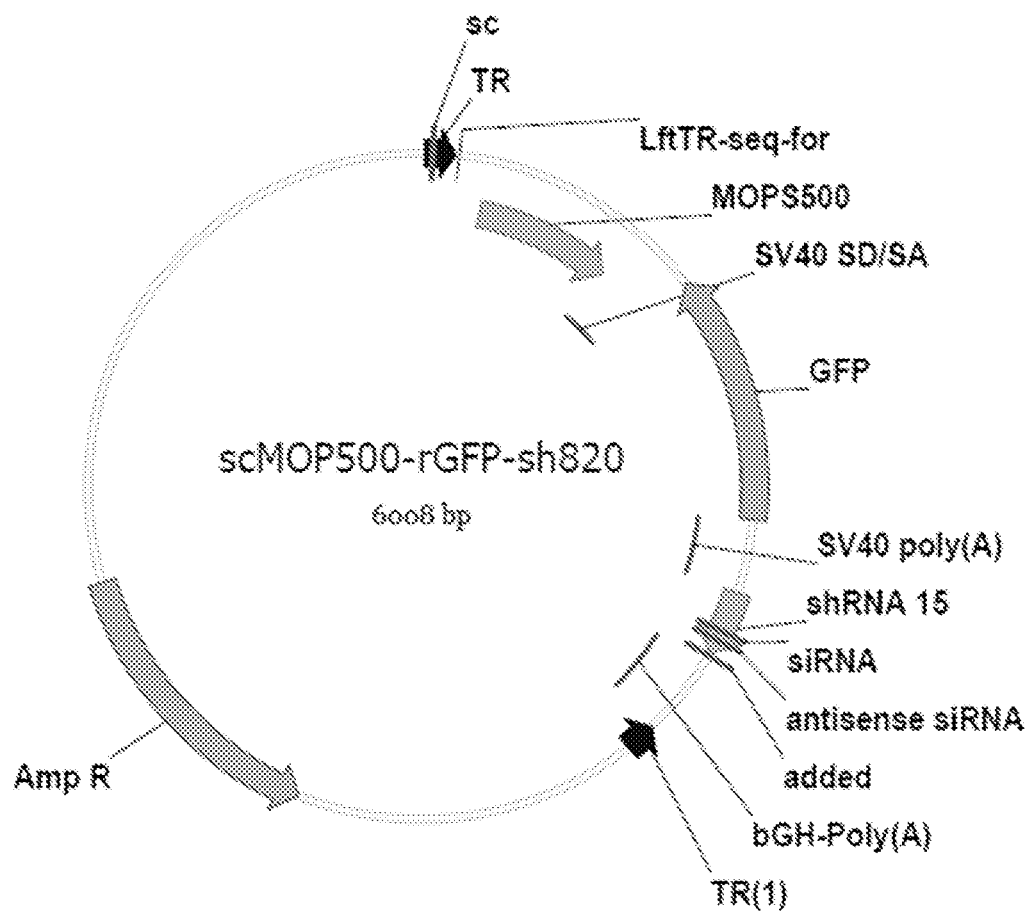
FIGS. 12A-12C shows non-limiting examples of maps of plasmids encoding siRNA (FIGS. 12A and 12B) and human RHO (FIG. 12C).
Figure 12B:
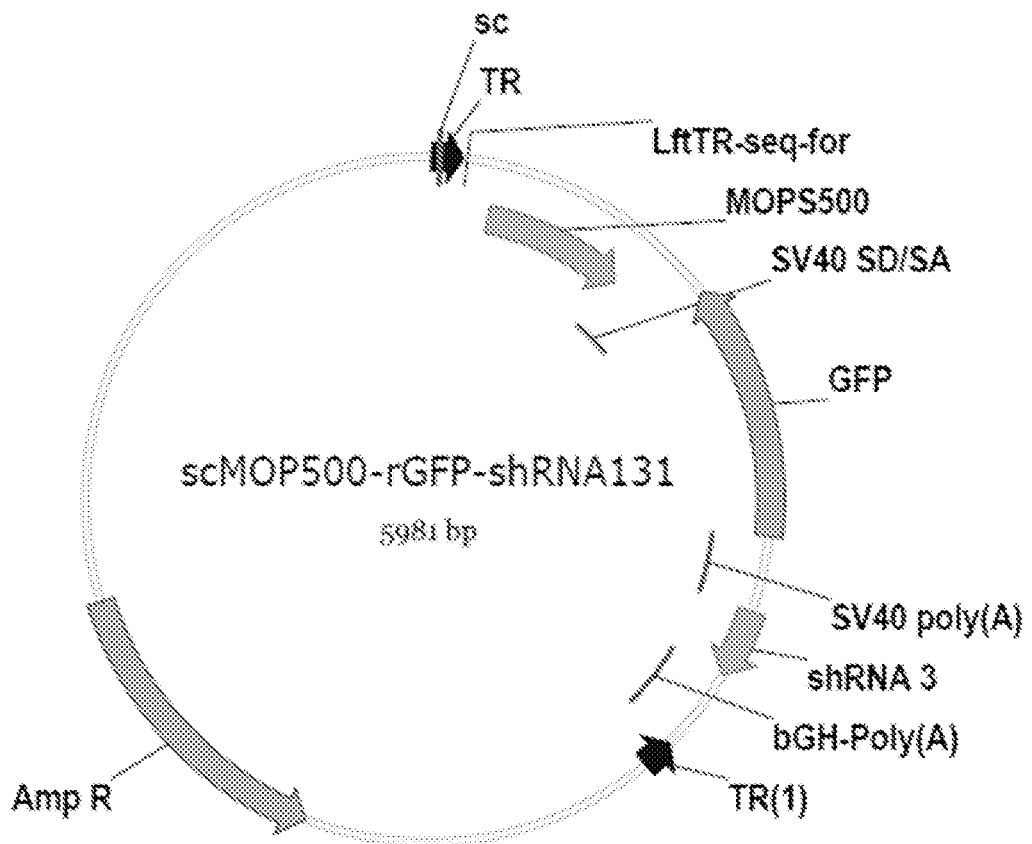

In some embodiments, it may be desirable to provide siRNA encoded in a DNA vector. FIGS. 12A-B depict non-limiting examples of siRNA (e.g., shRNA) encoded in a DNA vector. In some embodiments, as further depicted in the exemplary plasmid maps shown in FIG. 12A-B, the DNA vector can further encode inverted terminal repeat (ITR) sequences flanking the siRNA (e.g., shRNA). In some embodiments, a DNA vector encoding siRNA flanked by ITR sequences can be used in the production of recombinant AAV particles comprising the siRNA.

Figure 12C:
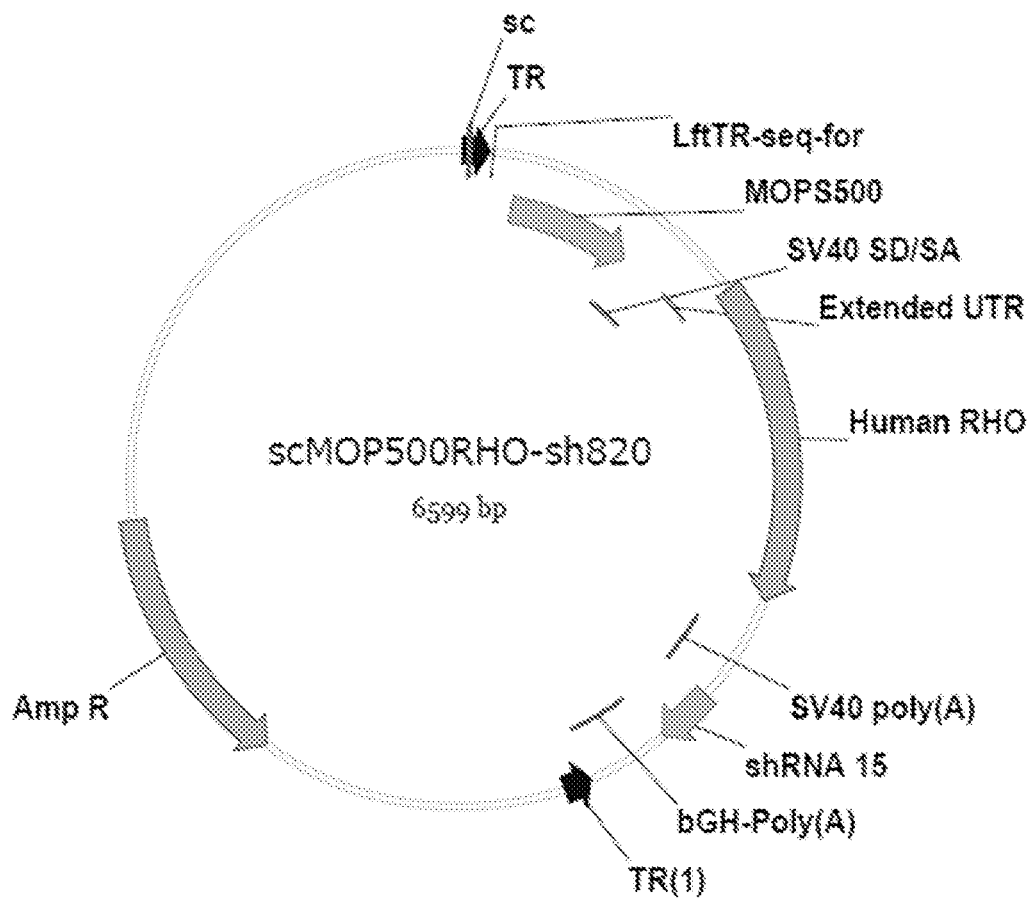

In some embodiments, it may be desirable to provide a replacement RHO mRNA encoded in a DNA vector. FIG. 12C depicts a non-limiting example of a replacement RHO mRNA (e.g., Human RHO) encoded in a DNA vector. In some embodiments, as further depicted in the exemplary plasmid map shown in FIG. 12C, the DNA vector can further encode ITR sequences flanking the replacement RHO mRNA (e.g., Human RHO). In some embodiments, a DNA vector encoding replacement RHO mRNA flanked by ITR sequences can be used in the production of recombinant AAV particles comprising the Human rho. In some embodiments, a similar DNA vector may be provided that includes both the replacement rho gene and one or more sequences encoding one or more interfering RNAs flanked by ITR sequences. In some embodiments, the interfering RNAs and/or replacement rho genes are operatively coupled to a promoter (e.g., an RNA polymerase III promoter, or H1 RNA polymerase III promoter, or other promoter as described in this application). The interfering RNAs and/or replacement rho genes represented in FIGS. 12A-C are under the control of an H1 RNA polymerase III promoter. The constructs of FIGS. 12A-C also include a MOP500-rGFP (a −385/+86 portion of the mouse rod opsin promoter (MOP500) upstream of the reversed sequence of GFP (rGFP) that is therefore not expressed) and can be referred to as H1 constructs or MOP500 constructs. However, the MOP500 (e.g., MOP500-rGFP) portion is not required.

from light-induced retinal degeneration in the mutant $RHO^{T4R/+}$ dogs, evidence that efficient knockdown of rhodopsin expression leads to a loss of outer segments in rods. Since preservation of outer segments is critical to phototransduction (the mechanism by which rods convert light into an electrical signal), an optimal therapy for RHO-ADRP should reduce native RHO but preserve outer segment structure. These results demonstrate that a knockdown approach is not sufficient and argue for the use of a combined knockdown and replacement strategy.

Five WT $RHO^{+/+}$ dogs received subretinal injections of AAV2/5-sc-H1-shRNA-Rho820 in both eyes at viral concentrations ranging from $1\times10^{11}$ to $5\times10^{12}$ vg/ml) as indicated in Table 8 below.

TABLE 8

RHO KD with shRNA820 in WT $RHO^{+/+}$ dogs

| Dog | Genotype | Sex | DOB | Age at injection | Right Eye (OD) | Left Eye (OS) |
|---|---|---|---|---|---|---|
| 2194 | rcd1 carrier | F | Aug. 11, 2014 | 1 year | AAV2/5-sc-H1-shRNA-Rho820 Ω4064 5E+12 vg/ml 150 ul SR | AAV2/5-sc-H1-shRNA-Rho820 Ω4064 1E+12 vg/ml Small bleb 50 ul SR |
| BR442 | RPE65 carrier | F | Dec. 15, 2013 | 1 Y + 11 M | AAV2/5-sc-H1-shRNA820 Ω4064 1E+12 vg/ml 150 ul SR | AAV2/5-sc-H1-shRNA820 Ω4064 1E+12 vg/ml 150 ul SR |
| GSR2 | CNGB3 carrier rcd1 carrier | M | Aug. 19, 2014 | 64 wks | AAV2/5-sc-H1-shRNA820 Ω4064 5E+11 vg/ml 150 ul SR | AAV2/5-sc-H1-shRNA820 Ω4064 5E+11 vg/ml 110 ul SR |
| P1474 | prcd carrier | M | Sep. 30, 2008 | 392 weeks/ 7 y | AAV2/5-sc-H1-shRNA820 Ω4064 2.5E+11 vg/ml 150 ul SR | AAV2/5-sc-H1-shRNA820 Ω4064 2.5E+11 vg/ml 150 ul SR |
| N282 | WT | M | Sep. 6, 2009 | 6 Yrs + 2 M | AAV2/5-sc-H1-shRNA820 Ω4064 1E+11 vg/ml 150 ul SR | AAV2/5-sc-H1-shRNA820 Ω4064 1E+11 vg/ml 160 ul SR |

Accordingly, a plasmid or rAAV nucleic acid can encode an interfering RNA and/or a modified rho gene as described herein, each under the control of the same or a different promoter (e.g., an H1 promoter) without a mouse opsin promoter and/or without any GFP coding sequence (in either orientation).

Example 6: Analysis of RHO KD with shRNA820 in WT $RHO^{+/+}$ Dogs

Example 6 includes the identification of viral titers of AAV2/5 carrying the shRNA820 knockdown reagent that efficiently silence rhodopsin expression after subretinal injection in WT dogs, evidence by in vivo retinal imaging in WT dogs of the preservation of the layer (ONL) that contains the photoreceptors, but reduction of the layers that contain rhodopsin following subretinal injection with AAV2/5-sc-H1-shRNA820, identification of viral titers of AAV2/5 carrying the shRNA820 knockdown reagent that efficiently silence rhodop sin expression after subretinal injection in the mutant $RHO^{T4R/+}$ dog, a naturally-occurring model of RHO-ADRP, identification of viral titers of AAV2/5-sc-H1-shRNA820 that confer protection to photoreceptors At 6-8 weeks post injection in vivo retinal imaging (cSLO/OCT) was performed and dogs were then terminated. Several 3 mm neuroretinal biopsy punches were collected from both eyes (dog 2194) or from the OS eye only (other dogs) in both bleb/treated and non-bleb/untreated regions to measure the level of expression of canine rhodopsin by western blot and RHO RNA by qPCR analysis. The OD eye was fixed, embedded in optimal cutting temperature media and processed for histology and immunohistochemistry staining.

Western Blot Analysis:

Up to three pairs of biopsy punches representing either bleb or non-bleb regions, were incubated in 50 ul of Lewin buffer solution A (containing protease inhibitors) for 15 min on ice. The samples were sonicated at 40% amplitude, 15 secON/10 secOFF×8 pulses. Samples were then centrifuged and the pellet discarded. Protein concentration in the supernatant was measured by Bradford method. Samples were stored at −20° C. 1 ug of total protein was loaded on gel for visualizing rhodopsin (Antibody used: Millipore MAB5356, diluted 1:1000 in Odyssey blocking buffer). Anti-histone H3 antibody (Abcam ab1791, diluted 1:3000) was used as a loading control and to normalize the signals.

Absolute Quantitation of Canine Rhodopsin RNA in Canine Retina:

In order to determine the absolute amounts of Rhodopsin RNA present in the retina after shRNA820-treatment, absolute quantitation was performed using Q-PCR Standard Curve method. Dilution series of known quantities of canine RHO cDNA was used to construct a standard curve. 0.1 nanogram of total cDNA was used for quantitation. Total amount of canine RHO RNA in each sample was calculated based on this standard curve.

Evaluation by in vivo retinal imaging of retinal integrity in eyes of WT $RHO^{+/+}$ dogs injected with different viral titers of AAV2/5-sc-H1-shRNA820.

Figure 13A:
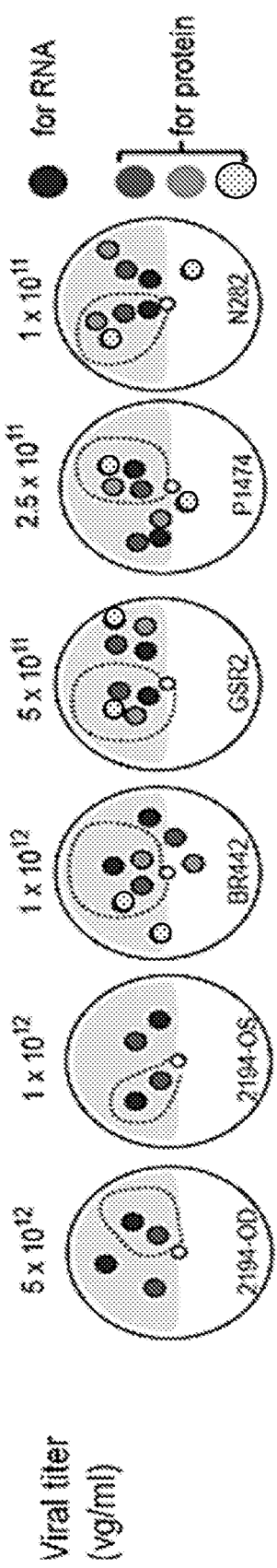
Figure 13B:
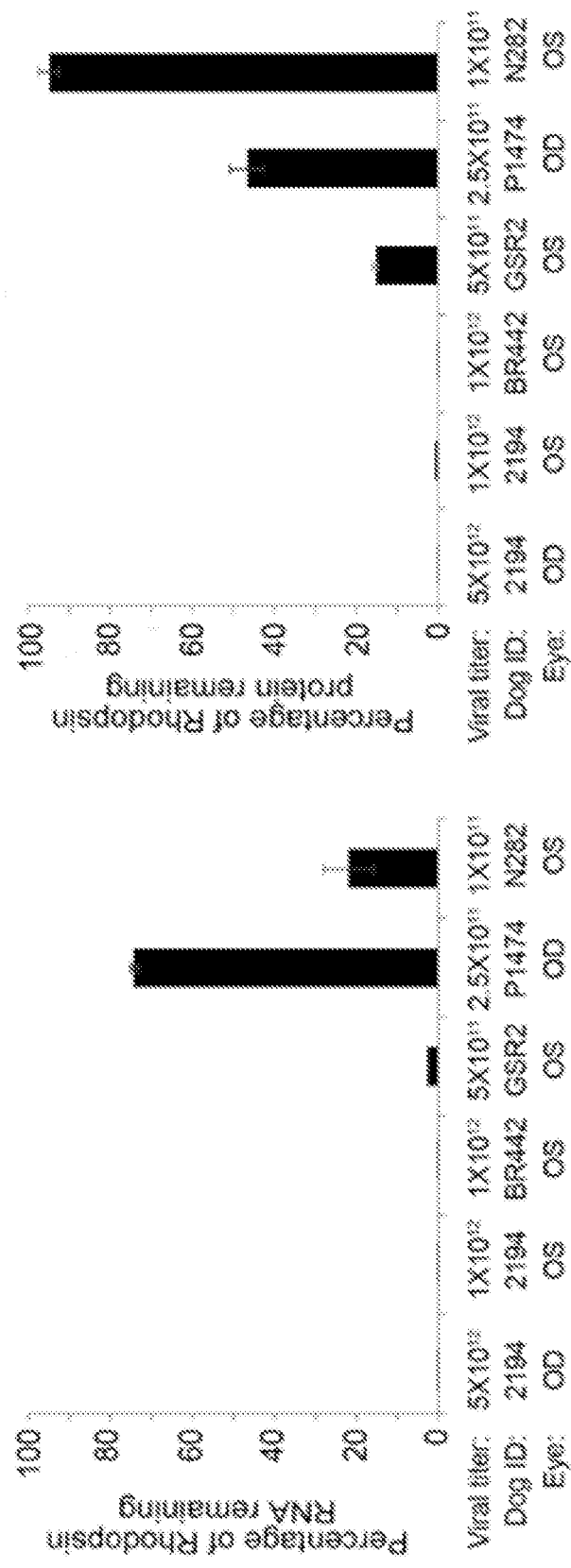
Figures 13C, 13D:
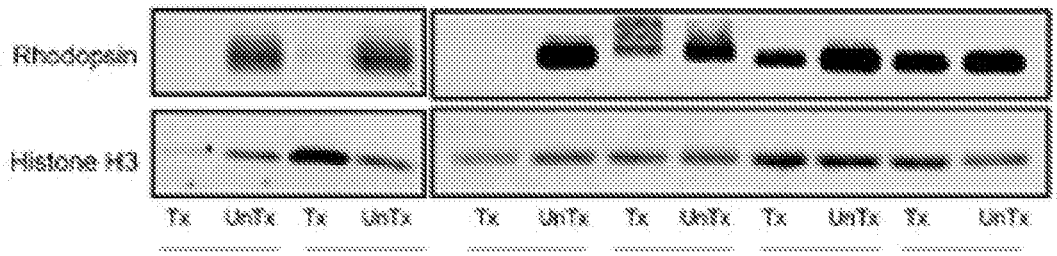

In vivo retinal imaging by cSLO/OCT was used to assess the retinal integrity of the ONL 6 to 8 weeks post subretinal injection of different titers of AAV2/5-sc-H1-shRNA820. Topographical maps of ONL thickness showed a preservation of this layer at all titers. Segmentation of the external limiting membrane (ELM), inner segments (IS), and outer segments (OS) revealed a reduction in signal intensity in the region corresponding to the bleb area in eyes injected with $1 \times 10^{12}$ and $5 \times 10^{12}$ vg/ml titers. These results suggest a shortening of the photoreceptor OS and IS as a results of RHO silencing and may be used to assess the efficacy of RHO KD in vivo. FIGS. 13A-13E show RNA and protein analysis of rhodopsin knockdown with different viral titers of AAV2/5-sc-H1-shRNA820 injected subretinally in WT $RHO^{+/+}$ dogs. FIG. 13A shows retinal maps showing position of biopsy punches used for western blot analysis and RNA quantitation. Paired dark gray, gray and dotted circles indicate the position of biopsy punches in the bleb/treated and non-bleb/untreated regions for each replication of western blot, whereas the black circles indicate the positions of biopsy punches for RNA quantitation. FIG. 13B shows a bar graph showing remaining canine Rhodopsin RNA in the treated area as a percentage of levels measured in the untreated area of the same retina. FIG. 13C shows immunoblot showing the amount of Rhodopsin in biopsy punches taken from treated (Tx) and untreated (UnTx) areas of canine retina. Histone H3 was used for normalization. Bar graphs show remaining canine Rhodopsin protein as a percentage of levels measured in the untreated area of the same retina. FIGS. 13D-13E show tables showing numerical values from each experiment (reported as a percentage of RNA or protein remaining, and alternatively as a percent knockdown of RNA or protein, respectively).

Figure 14A:
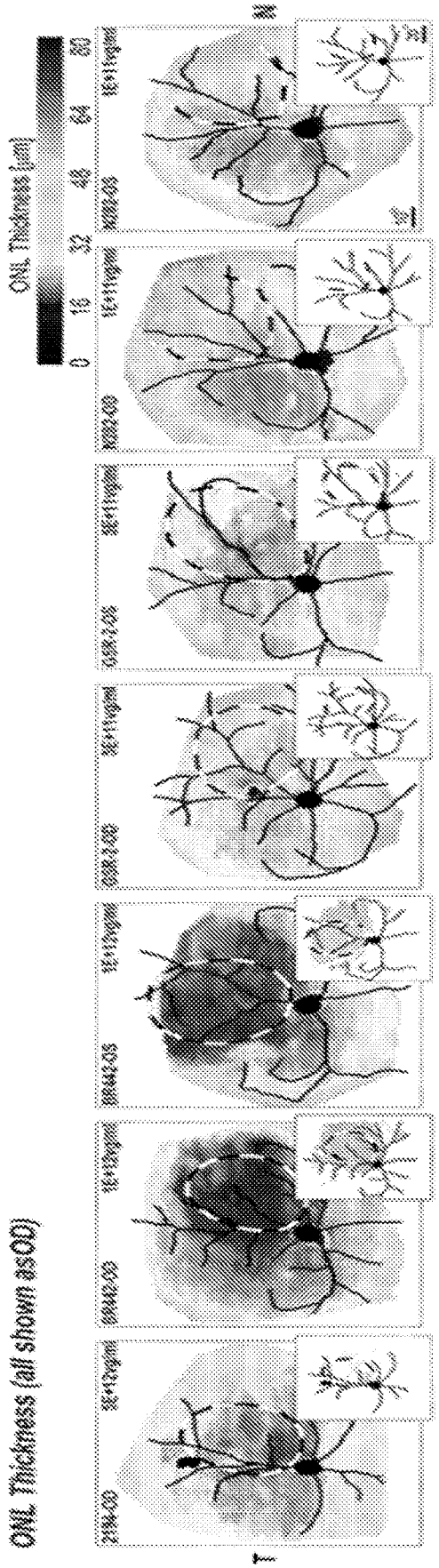
FIGS. 14A-14D show the assessment of ONL and ELM/IS/OS integrity following subretinal injection of different titers of AAV2/5-sc-H1-shRNA820 in WT dogs.
Figure 14B:
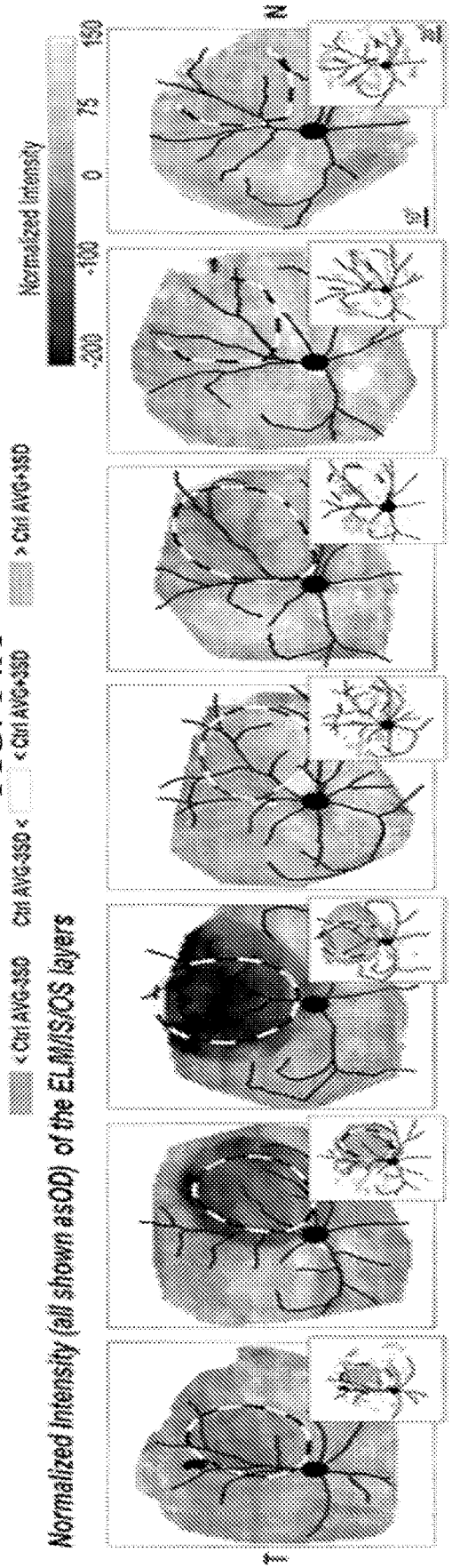
Figure 14C:
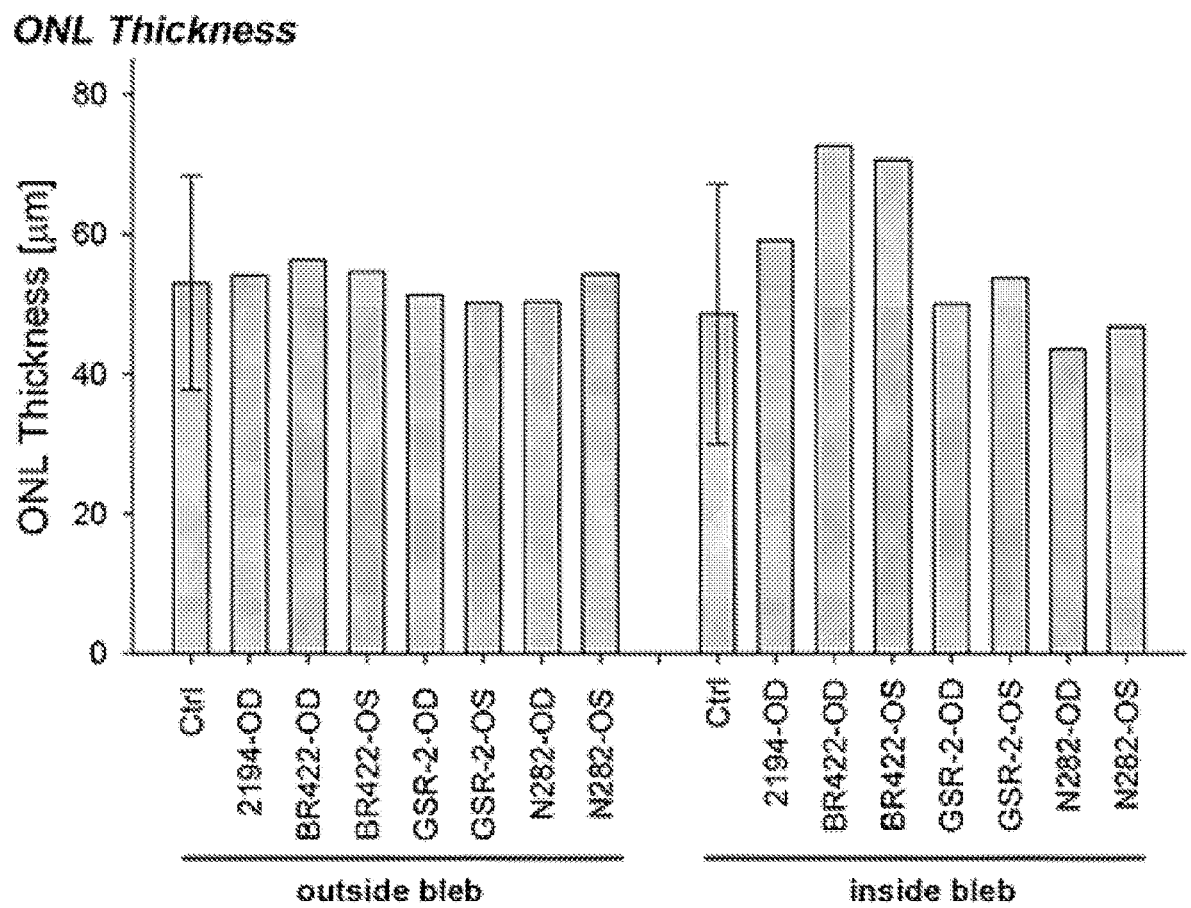
Figure 14D:
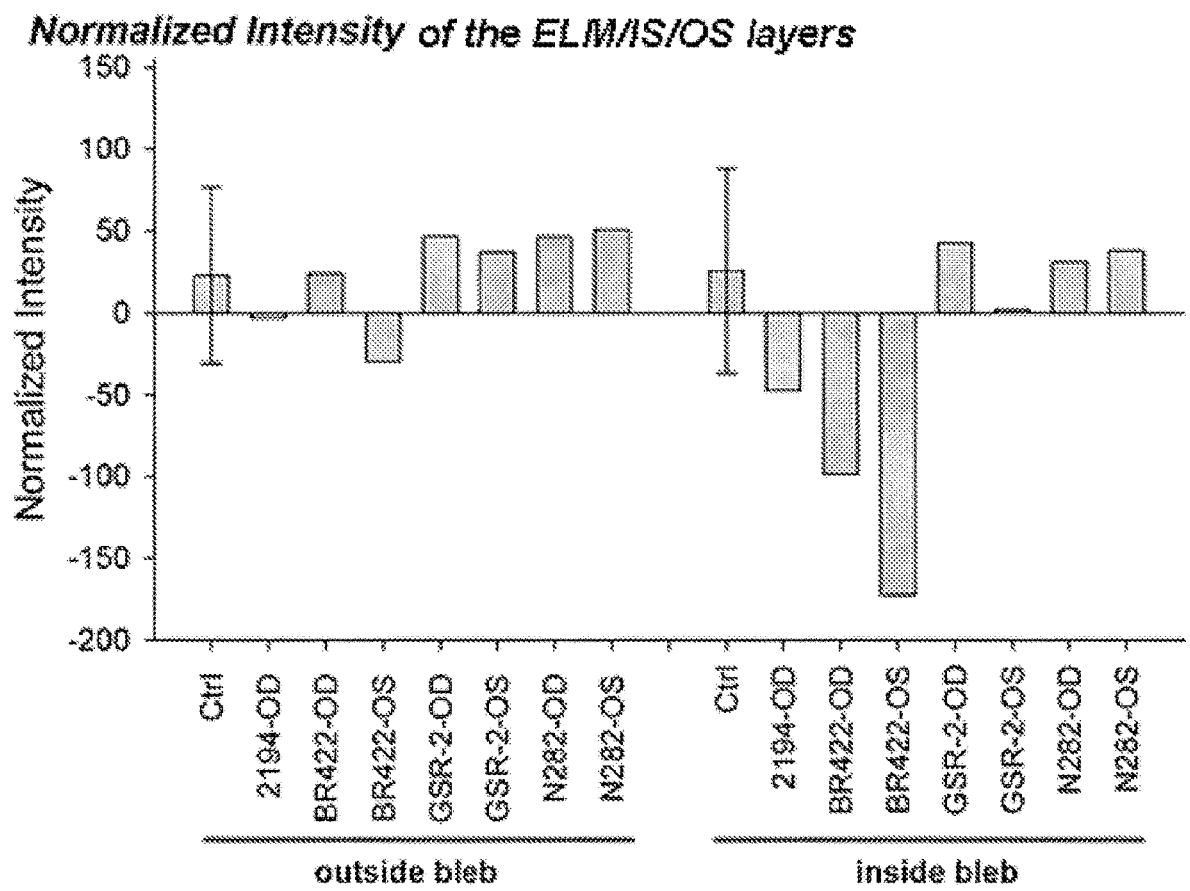

FIGS. 14A-D show the assessment of ONL and ELM/IS/OS integrity following subretinal injection of different titers of AAV2/5-sc-H1-shRNA820 in WT dogs. FIG. 14A shows ONL thickness maps; FIG. 14B shows ELM/IS/OS maps of normalized intensity; FIG. 14C shows ONL thickness values; and FIG. 14D shows values of normalized intensity of the ELM/IS/OS layers. These results suggest a shortening of the photoreceptor OS and IS as a results of RHO silencing and may be used to assess the efficacy of RHO KD in vivo.

Complete knockdown of canine RHO RNA and protein was seen in WT dogs with AAV2/5-sc-H1-shRNA820 injected subretinally at viral titers as low as $1 \times 10^{12}$ vg/ml. No reduction in ONL thickness was seen even with the highest viral concentration suggesting that knockdown of rhodopsin does not induce photoreceptor cell death. A decrease in OCT reflectivity of the ELM/IS/OS layers is seen in the treated/bleb region of eyes injected with high viral titers that induce 100% KD of rhodopsin. This observation is compatible with a thinning of these layers and may be used as an in vivo outcome measure of KD efficiency.

Example 7: Analysis of RHO KD with shRNA820 in $RHO^{T4R/+}$ Mutant Dogs

Four $RHO^{T4R/+}$ dogs received subretinal injections of AAV2/5-sc-H1-shRNA-Rho820 in both eyes at viral concentrations indicated in Table 9 below.

TABLE 9

RHO KD with shRNA820 in $RHO^{T4R/+}$ mutant dogs

| Dog | Genotype | Sex | DOB | Age at injection | Right Eye (OD) | Left Eye (OS) |
| --- | --- | --- | --- | --- | --- | --- |
| EM409 | T4R/+ | F | Feb. 10, 2015 | 40 wks | AAV2/5-sc-H1-shRNA820 Ω4064 1E+12 vg/ml 150 ul SR | AAV2/5-sc-H1-shRNA820 Ω4064 1E+12 vg/ml 150 ul SR |
| EM411 | T4R/+ | F | Feb. 10, 2015 | 40 wks | AAV2/5-sc-H1-shRNA-820 Ω4064 5E+11 vg/ml 160 ul SR | AAV2/5-sc-H1-shRNA820 Ω4064 5E+11 vg/ml 150 ul SR |
| EM413 | T4R/+ | F | Feb. 10, 2015 | 57 weeks | AAV2/5-sc-H1-shRNA820 Ω4064 2.5E+11 vg/ml 150 ul SR | AAV2/5-sc-H1-shRNA820 Ω4064 2.5E+11 vg/ml 150 ul SR |
| EM412 | T4R/+ | F | Feb. 10, 2015 | 40 wks | AAV2/5-sc-H1-shRNA820 Ω4064 1E+11 vg/ml 150 ul SR | AAV2/5-sc-H1-shRNA820 Ω4064 1E+11 vg/ml 150 ul SR | cSLO/OCT was performed at 8 weeks post injection and light exposure (1 min at 1 mW/cm$^2$) was performed on OS eye in all dogs to trigger light-induced retinal degeneration. cSLO/OCT was performed again on all dogs 2 weeks post light exposure to assess any rescue effect conferred by the treatment. Dogs were terminated and several 3 mm neuroretinal biopsy punches were collected from OD eye from both bleb/treated and non-bleb/untreated regions to measure the level of expression of canine Rhodopsin by western blot and RHO RNA by qPCR analysis. The OS eye was fixed, embedded in optimal cutting temperature media and processed for histology and immunohistochemistry staining.

Western Blot Analysis:

Three pairs of biopsy punches from each OS eye, representing either bleb/treated or non-bleb/untreated retinal regions, were incubated in 50 ul of Lewin buffer solution A (containing protease inhibitors) for 15 min on ice. The samples were sonicated at 40% amplitude, 15 secON/10 secOFF×8 pulses. Samples were then centrifuged and the pellet discarded. Protein concentration in the supernatant was measured by Bradford method. Samples were stored at −20° C. 1 ug of total protein was loaded on gel for visualizing Rhodopsin (Antibody used: Millipore MAB5356, diluted 1:1000 in Odyssey blocking buffer). Anti-histone H3 antibody (Abcam ab1791, diluted 1:3000) was used as a loading control and to normalize the signals.

Absolute Quantitation of Canine Rhodopsin RNA in Canine Retina:

In order to determine the absolute amounts of Rhodopsin RNA present in the retina after shRNA820-treatment, absolute quantitation was performed using Q-PCR Standard Curve method. Dilution series of known quantities of canine RHO cDNA was used to construct a standard curve. 0.1 nanogram of total cDNA was used for quantitation. Total amount of canine RHO RNA in each sample was calculated based on this standard curve.

Evaluation by In Vivo Retinal Imaging of Photoreceptor Rescue from Light-Induced Damage in Eyes of Mutant $RHO^{T4/R/+}$ Dogs Injected with Different Viral Titers of AAV2/5-shRNA820.

Eyes from mutant $RHO^{T4R/+}$ dogs that were subretinally injected with viral titers ranging from $1\times10^{12}$ down to $1\times10^{11}$ vg/ml were examined by cSLO/OCT imaging 8 weeks post injection (before light exposure). ONL thickness in the bleb/treated area was preserved suggesting that shRNA820 did not cause any loss of photoreceptors during that period. A 1 min exposure to white light at an intensity (corneal irradiance of 1 mW/cm$^2$) previously shown to cause acute retinal degeneration in RHO T4R mutant but not in WT dogs was used to assess the level of protection conferred by the AAV2/5-sc-H1-shRNA820 in the treated/bleb area. The surrounding non bleb/untreated regions were used as an internal control for each eye. Two weeks post light-exposure retinas were re-imaged, and showed good preservation of ONL thickness in the bleb/treated area of eyes injected with $1\times10^{12}$ and $5\times10^{11}$ vg/ml titers. Very mild rescue was seen at $2.5\times10^{11}$ vg/ml and none with $1\times10^{11}$ vg/ml titers.

Figure 15A:
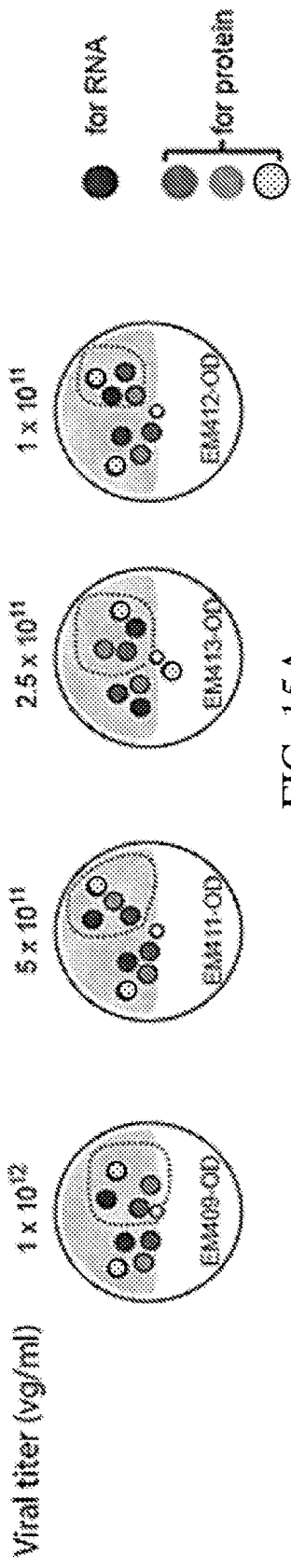
Figure 15B:
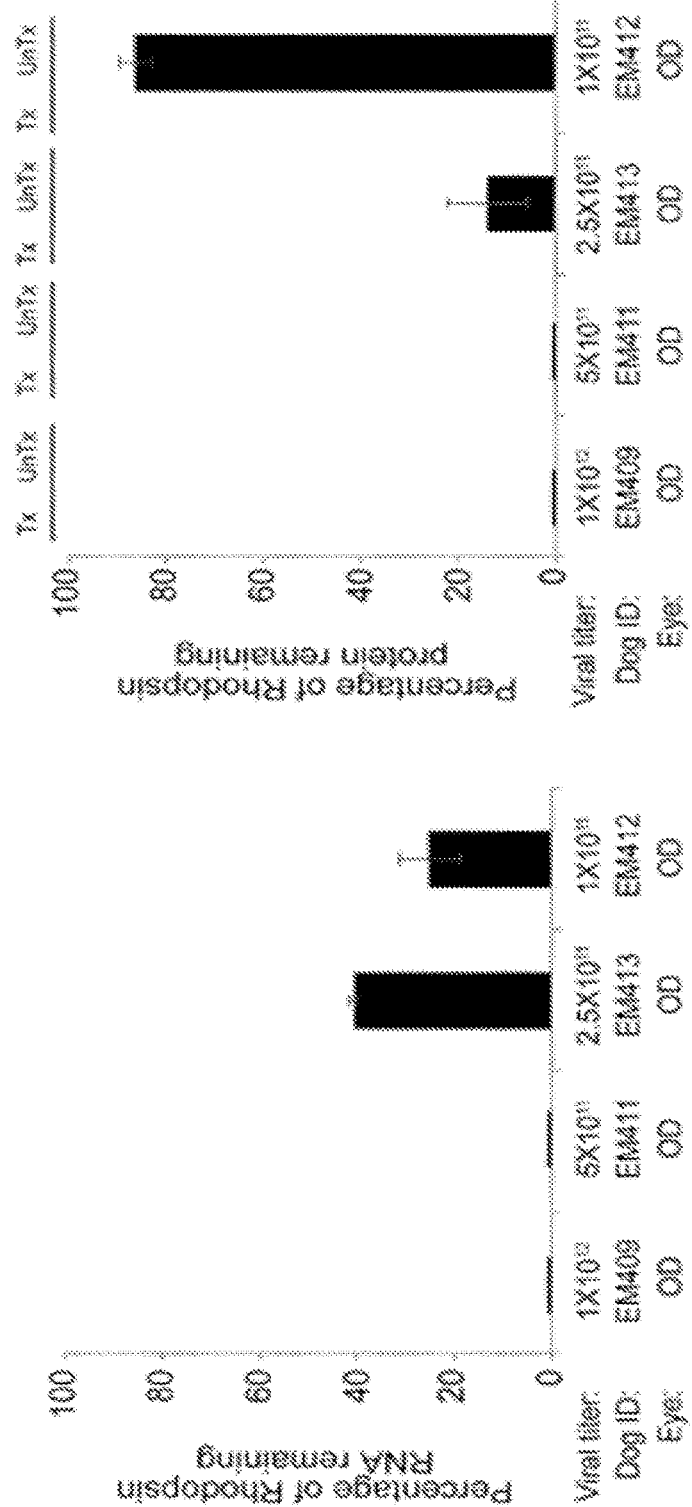
Figures 15C, 15D:
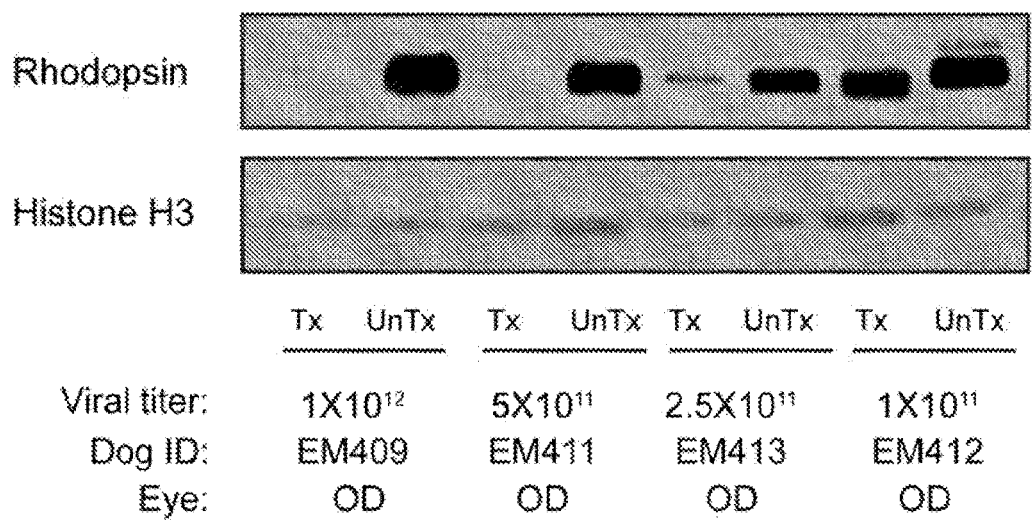

FIGS. 15A-15E show RNA and protein analysis of rhodopsin knockdown with different viral titers of AAV2/5-sc-H1-shRNA820 injected subretinally in mutant $RHO^{T4R/+}$ dogs. FIG. 15A shows retinal maps showing position of biopsy punches used for western blot analysis and RNA quantitation. Paired dark gray, gray and dotted circles indicate the position of biopsy punches in the bleb and non-bleb region for each replication of western blot, whereas the black circles indicate the position of biopsy punches for RNA quantitation. FIG. 15B is a bar graph showing the amount of remaining canine Rhodopsin RNA as a percentage of levels measured in the untreated area of the same retina. FIG. 15C is an immunoblot showing the amount of canine Rhodopsin in biopsy punches taken from treated (Tx) and untreated (UnTx) areas of canine retina. Histone H3 was used for normalization. Bar graphs show the amount of remaining canine Rhodopsin protein as a percentage of levels measured in the untreated area of the same retina. FIGS. 15D-15E are tables showing numerical values from each experiment (reported as a percentage of RNA or protein remaining, and alternatively as a percent knockdown of RNA or protein, respectively).

Figure 17A:
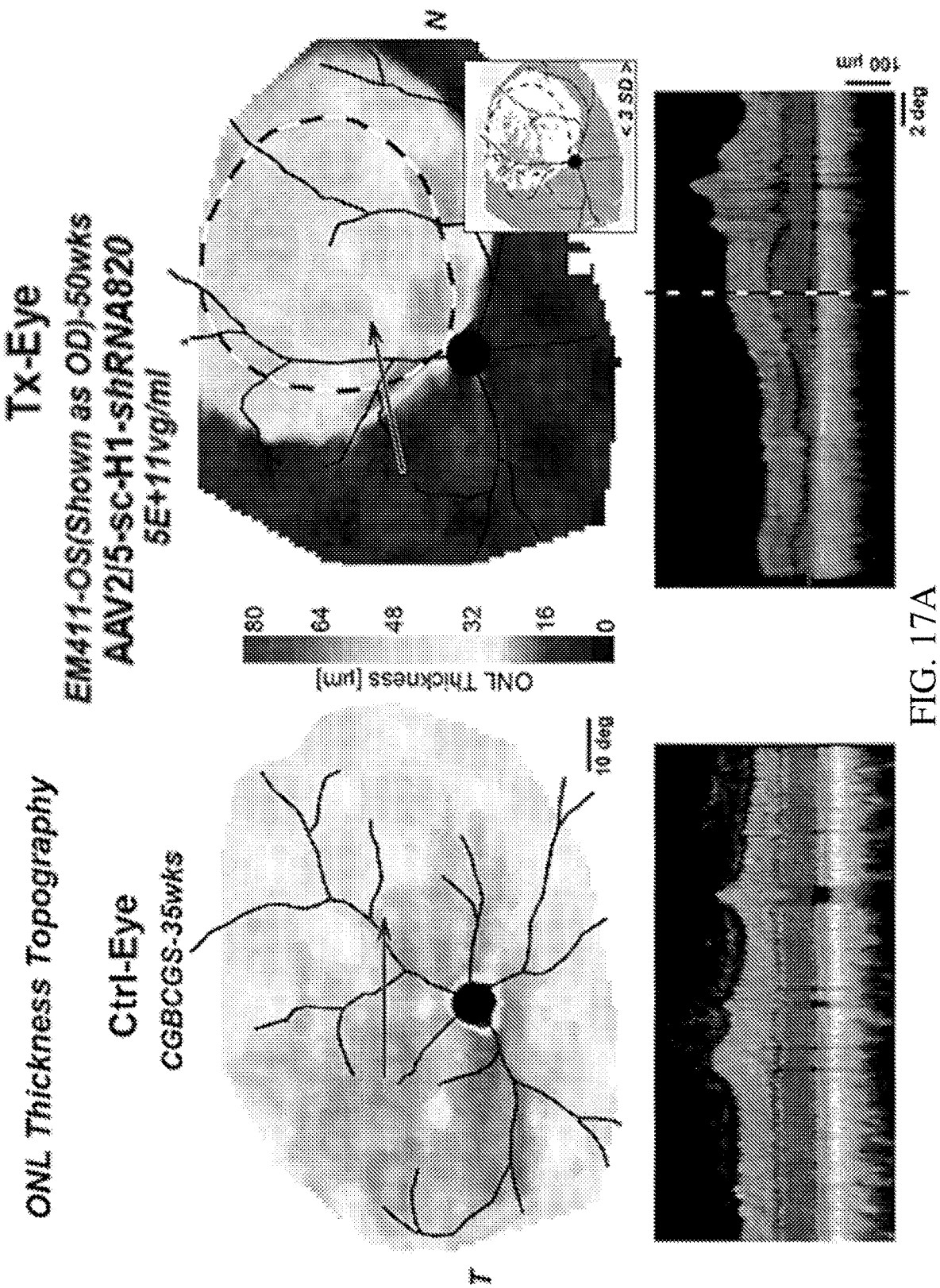
FIGS. 17A-17B show topographic map ONL thickness from a $RHO^{T4R/+}$ treated with AAV2/5-sc-H1-shRNA820 showing protection from light-induced retinal degeneration.
Figure 17B:
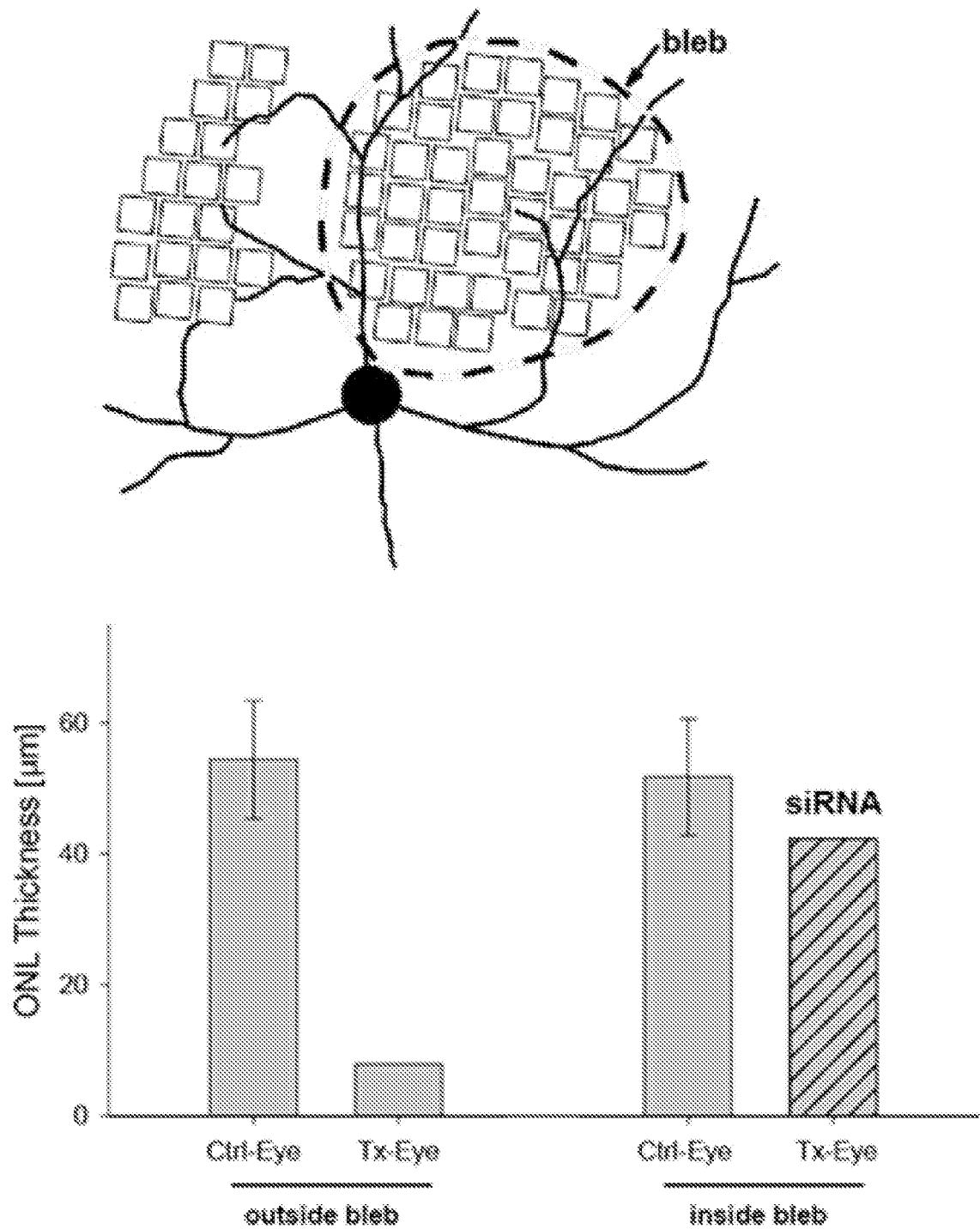

FIGS. 16A-16D show OCT B scans encompassing the treated (with different viral titers of AAV2/5-sc-H1-shRNA820) and untreated retinal areas of $RHO^{T4R/+}$ dogs 2 weeks following exposure to a brief dose of light that causes acute retinal degeneration in mutant $RHO^{T4R/+}$ dogs. (FIG. 16A) OCT scan of a dog treated with $1\times10^{12}$ vg/ml. (FIG. 16B) OCT scan of a dog treated with $5\times10^{11}$ vg/ml. (FIG. 16C) OCT scan of a dog treated with $2.5\times10^{11}$ vg/ml. (FIG. 16D) OCT scan of a dog treated with $1\times10^{11}$ vg/ml. FIGS. 17A-17B show topographic map ONL thickness from a $RHO^{T4R/+}$ treated with AAV2/5-sc-shRNA820 showing protection from light-induced retinal degeneration. (FIG. 17A) ONL thickness map of an untreated WT control dog (left panel), and ONL thickness map of EM411-OS treated with AAV2/5-sc-shRNA820 at 5E+11 vg/ml and showing preserved ONL thickness in the treated/bleb region weeks after light-induced damage. Black and white curve shows the limits of the bleb as seen immediately after the subretinal injection. Panels below show OCT B scans with ONL colored in darker gray (middle band) for visualization purposes. (FIG. 17B) Loci outside and inside the bleb were selected for ONL thickness measurements.

Complete knockdown of canine RHO RNA and protein (by western blot) was seen with AAV2/5-shRNA-Rho820 at a viral titer of $1\times10^{12}$ and $5\times10^{11}$ vg/ml. Complete rescue of the outer nuclear layer (ONL) which contains the cells bodies of the photoreceptors was achieved with AAV2/5-shRNA-Rho820 at a viral titer of $1\times10^{12}$ and $5\times10^{11}$ vg/ml.

Evaluation by Histology and Immunohistochemistry of Photoreceptor Protection from Light-Induced Damage in Eyes of Mutant $RHO^{T4R/+}$ Dogs Injected with Different Viral Titers of AAV2/5-Sc-H1-shRNA820.

Figure 18:
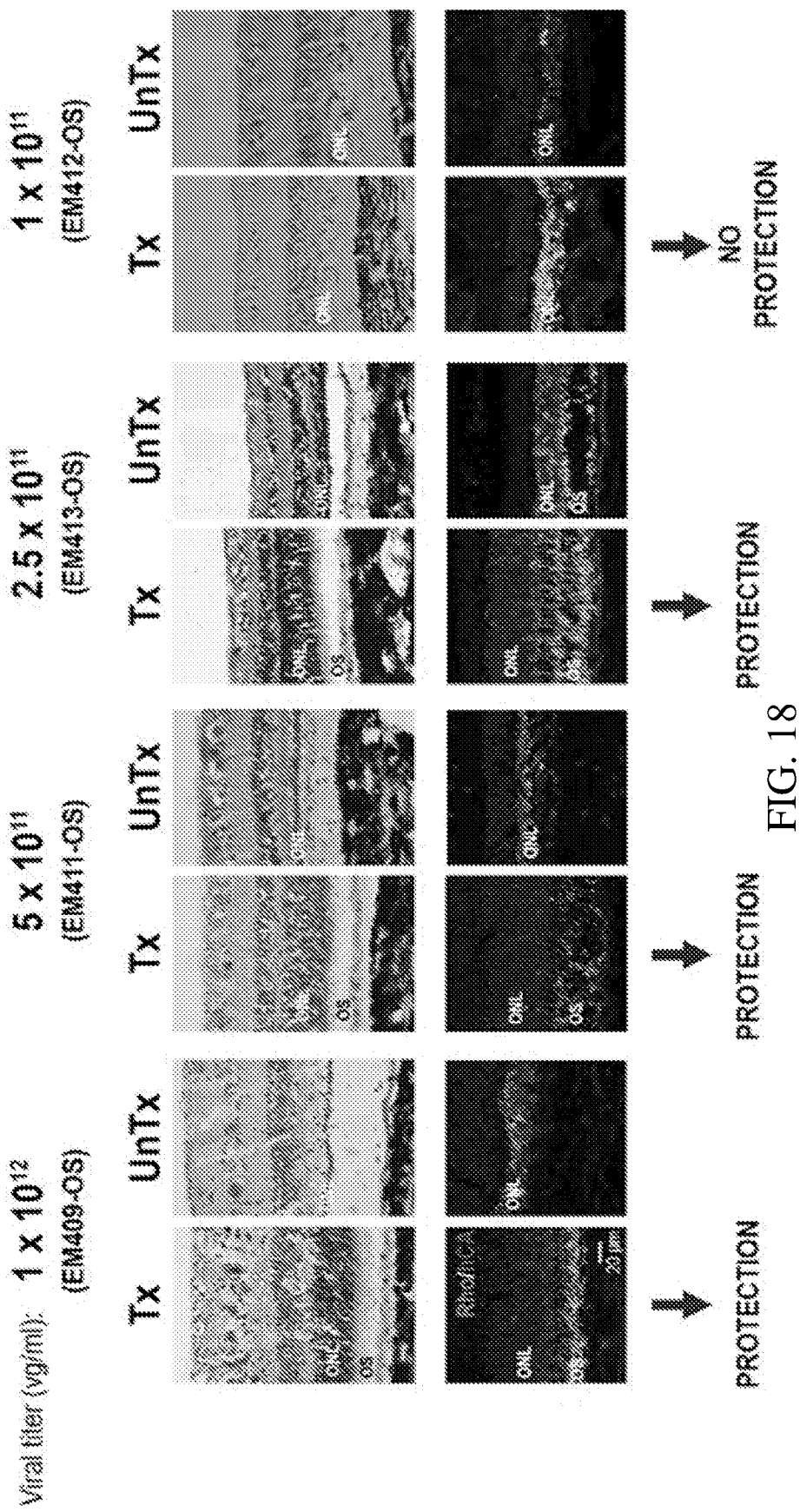
FIG. 18 shows histology (H&E stained) and immunohistochemistry (Rhodopsin was stained in green and appears as light staining in the lower panels of FIG. 18; human cone arrestin was stained in red and appears as gray staining in the lower panels of FIG. 18) in the treated (Tx) and Untreated (UnTx) areas of mutant $RHO^{T4R/+}$ retinas subretinally with different viral titers AAV2/5-sc-H1-shRNA820.

Eyes from the same mutant $RHO^{T4R/+}$ dogs listed in the above Table that were subretinally-injected with viral titers ranging from $1\times10^{12}$ down to $1\times10^{11}$ vg/ml and subsequently light exposed (at 8 weeks post injection) to 1 min duration of white light at an intensity (corneal irradiance of 1 mW/cm$^2$) were examined. This dose of light was previously shown to cause acute retinal degeneration in RHO T4R mutant but not in WT dogs. Histology and immunohistochemistry were used to assess the level of protection conferred by the AAV2/5-sc-H1-shRNA820 in the treated/bleb area. The surrounding non bleb/untreated regions were used as an internal control for each eye. Antibodies directed against rhodopsin (RHO), and human cone arrestin (hCA) were used to assess the integrity of rod outer segments and cone morphology. FIG. 18 shows histology (H&E stained) and immunohistochemistry (Rhodopsin was stained in green and appears as the lighter staining in the lower panels of FIG. 18; human cone arrestin was stained in red and appears as the gray staining in the lower panels of FIG. 18) in the treated (Tx) and Untreated (UnTx) areas of mutant $RHO^{T4R/+}$ retinas injected subretinally with different viral titers AAV2/5-sc-H1-shRNA820. Two weeks post light-exposure good preservation of ONL thickness in the bleb/treated area of eyes injected with $1\times10^{12}$ and $5\times10^{11}$ vg/ml titers was seen, while ONL thickness was slightly reduced at $2.5\times10^{11}$ vg/ml, and no protection was observed with $1\times10^{11}$ vg/ml titers. Consistent with the very efficient knockdown of rhodopsin expression at $1\times10^{12}$ and $5\times10^{11}$ vg/ml titers, and reduction in the length of rod OS was seen on H&E sections, combined with a reduction in rhodopsin expression.

Complete knockdown of canine RHO RNA and protein (by western blot) is seen with AAV2/5-sc-H1-shRNA820 at a viral titer of $1\times10^{12}$ and $5\times10^{11}$ vg/ml. Complete protection of the outer nuclear layer (ONL) which contains the cells bodies of the photoreceptors is achieved with AAV2/5-sc-H1-shRNA820 at a viral titer of $1\times10^{12}$ and $5\times10^{11}$ vg/ml. Loss of outer segment structure in rods as a result of efficient RHO knockdown argues for the need of a combined KD and replacement strategy to allow treated rods to retain outer segments and remain functional.

Example 8

This Example provides data supporting gene therapy using RHO-ADRP. It includes testing in mutant $RHO^{T4R/+}$ dog an AAV2/5 vector construct (AAV2/5-sc-HOP-RHO820-H1-shRNA820) that combines both the shRNA820 knockdown reagent and the replacement reagent RHO820 (=hardened human RHO mRNA), identification of viral titers of AAV2/5-sc-HOP-RHO820-H1-shRNA820 that result in efficient knockdown of endogenous canine RHO, and efficient expression of the replacement hardened human RHO (RHO820), evidence that AAV2/5-sc-HOP-RHO820-H1-shRNA820 confers protection to photoreceptors from light-induced retinal degeneration in the mutant $RHO^{T4R/+}$ dogs, and evidence that preservation of rod outer segments is achieved in retinal areas treated with AAV2/5-sc-HOP-RHO820-H1-shRNA820.

Analysis of RHO KD & Replacement with shRNA820 and RHO820 in $RHO^{T4R/+}$ Mutant Dogs:

Two $RHO^{T4R/+}$ dogs received subretinal injections of AAV2/5-sc-HOP-RHO820-H1-shRNA820 in both eyes at viral concentrations indicated in the table below (Table 10).

(containing protease inhibitors) for 15 min on ice. The samples were sonicated at 40% amplitude, 15 sec ON/10 sec OFF×8 pulses. Samples were then centrifuged and the pellet discarded. Protein concentration in the supernatant was measured by Bradford method. Samples were stored at −20° C. 1 ug of total protein was loaded on gel for visualizing Rhodopsin (Antibody used: Millipore MAB5356, diluted 1:1000 in Odyssey blocking buffer). Note that this antibody detects both canine and human RHO. Due to loss of glycosylation at Asn2, mutant T4R rhodopsin can be differentiated from WT (canine or human) RHO protein as it has a lower MW that can be detected on immunoblots. RHO immunoblots from heterozygous mutant $RHO^{T4R/+}$ thus show two bands corresponding to WT (high MW), and mutant T4R (low MW) RHO proteins. Anti-histone H3 antibody (Abcam ab1791, diluted 1:3000) was used as a loading control and to normalize the signals.

Absolute Quantitation of Canine and Human Rhodopsin RNA in Canine Retina:

In order to determine the absolute amounts of both endogenous canine Rhodopsin RNA and human RHO820 RNA present in the retina after treatment with AAV2/5-sc-HOP-RHO820-H1-shRNA820, absolute quantitation was performed using Q-PCR Standard Curve method. Dilution series of known quantities of canine and human RHO cDNA were used to construct a standard curve. 0.1 nanogram of total cDNA was used for quantitation. Total amount of canine RHO and human RHO820 RNA in each sample was calculated based on this standard curve.

FIGS. 19A-19F show RNA and protein analysis of rhodopsin knockdown and replacement with AAV2/5-sc-HOP-RHO820-H1-shRNA820 injected subretinally in mutant

TABLE 10

| Dog | Genotype | Sex | DOB | Age at injection | Right Eye (OD) | Left Eye (OS) |
| --- | --- | --- | --- | --- | --- | --- |
| EM424 | T4R/+ | M | Apr. 29, 2016 | 27 weeks | AAV2/5-sc-HOP-RHO820-H1-shRNA820 P4337 5E+11 vg/ml 150 ul SR | AAV2/5-sc-HOP-RHO820-H1-shRNA820 P4337 5E+11 vg/ml 150 ul SR |
| EM425 | T4R/+ | M | Apr. 29, 2016 | 27 weeks | AAV2/5-sc-HOP-RHO820-H1-shRNA820 P4337 5E+11 vg/ml 150 ul SR | AAV2/5-sc-HOP-RHO820-H1-shRNA820 P4337 5E+11 vg/ml 150 ul SR |

HOP: human opsinpromoter;
H1: H1 RNA polymerase III promoter

In vivo retinal imaging (cSLO/OCT) was performed at 11 weeks post injection and light exposure (1 min at 1 mW/cm$^2$) was performed on OS eye in both dogs to trigger light-induced retinal degeneration. cSLO/OCT was performed again on all dogs 2 weeks post light exposure to assess any rescue effect conferred by the treatment. Dogs were terminated and several 3 mm neuroretinal biopsy punches were collected from OD eye from both bleb/treated and non-bleb/untreated regions to measure the level of expression of Rhodopsin by western blot and canine and human RHO RNA by qPCR analysis. The OS eye was fixed, embedded in optimal cutting temperature media and processed for histology and immunohistochemistry staining.

Western Blot Analysis:

Three pairs of biopsy punches from each OD eye, representing either bleb/treated or non-bleb/Untreated retinal regions, were incubated in 50 ul of Lewin buffer solution A $RHO^{T4R/+}$ dogs at $5\times10^{11}$ vg/ml titer. FIG. 19A shows retinal maps showing position of biopsy punches used for western blot analysis and RNA quantitation. Paired dark gray, gray and dotted circles indicate the position of biopsy punches in the treated (Tx) and untreated (UnTx) regions for each replication of western blot, whereas the black circles indicate the position of biopsy punches for RNA quantitation. FIG. 19B shows immunoblot showing the amount of total rhodopsin (canine+human RHO820) in biopsy punches taken from treated (Tx) and untreated (UnTx) areas of canine retina. Histone H3 was used for normalization. Bar graphs show the percentage of remaining rhodopsin protein in the Treated and untreated areas. Note the loss of the lower MW band (corresponding to mutant T4R RHO protein) in the treated areas of EM424-OD and EM425-OD. FIG. 19C is a table showing numerical values for each pair of punches used for protein quantification. FIG. 19D is a bar graph showing remaining canine Rhodopsin RNA in the treated areas as a percentage of canine RHO RNA levels measured in untreated areas. FIG. 19E is a bar graph showing levels of human RHO820 in the treated areas as a percentage of canine RHO RNA levels measured in untreated areas. FIG. 19F is a table showing numerical values for each pair of punches used for RNA quantification.

Evaluation by In Vivo Retinal Imaging of Photoreceptor Protection from Light-Induced Damage in Eyes of Mutant RHO$^{T4R/+}$ Dogs Injected Subretinally AAV2/5-Sc-HOP-RHO820-H1-shRNA820 at $5\times10^{11}$ vg/ml:

Eyes from 2 mutant RHO T4R/+ dogs that were subretinally injected with viral titer of $5\times10^{11}$ vg/ml were examined by cSLO/OCT imaging before injection, 11 weeks post injection (before light exposure), and 2 weeks post light-damage. A 1 min exposure to white light at an intensity (corneal irradiance of 1 mW/cm2) previously shown to cause acute retinal degeneration in RHO T4R mutant but not in WT dogs was used to assess the level of protection conferred by the AAV2/5-sc-HOP-RHO820-H1-shRNA820 vector in the treated/bleb area. ONL thickness in the bleb/treated area was preserved at all post-injection time points suggesting that this vector construct was not toxic and that there was no loss of photoreceptors during that period. The surrounding non bleb/untreated regions were used as an internal control for each eye. Two weeks post light-exposure there was complete preservation of ONL thickness in the bleb/treated area in both injected eyes.

Figure 21:
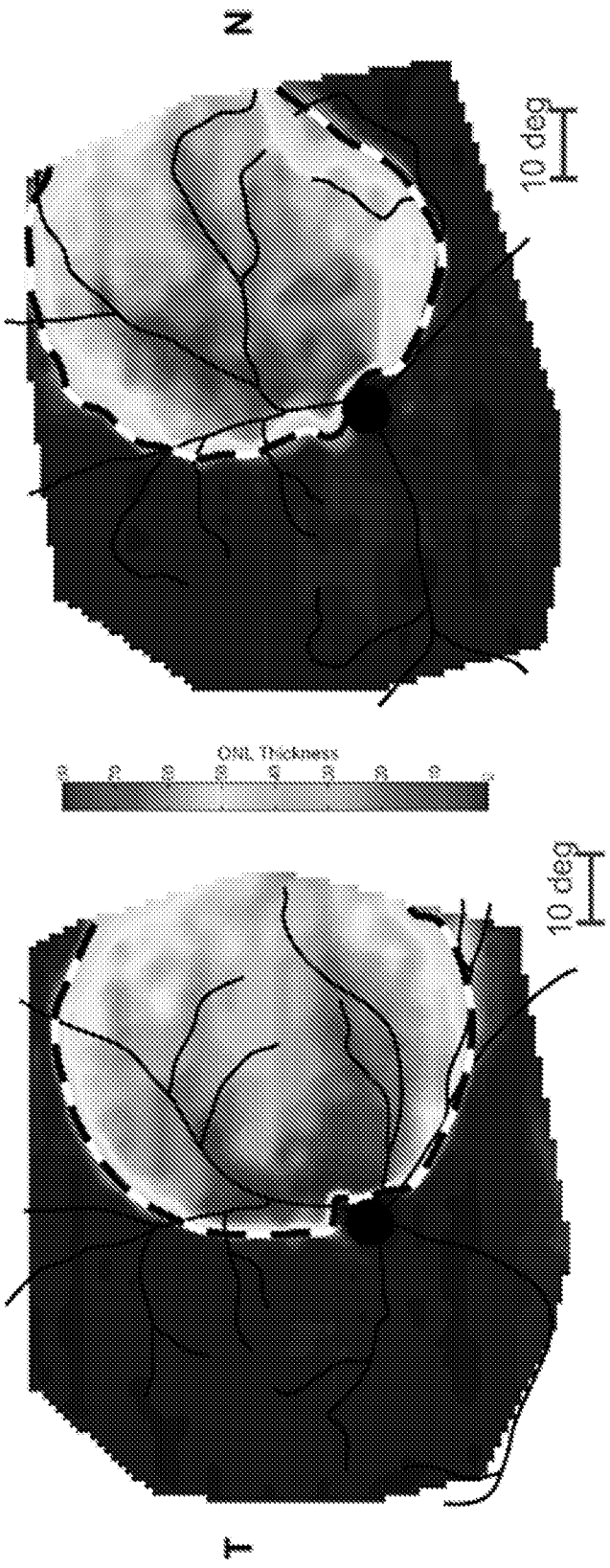
FIG. 21 shows topographic maps of ONL thickness from a two $RHO^{T4R/+}$ treated with AAV2/5-sc-HOP-RHO820-H1-shRNA820 at $5 \times 10^{11}$/vg/ml titer showing protection from light-induced retinal degeneration.

FIGS. 20A-20C show in vivo retinal imaging showing protection from light-induced retinal degeneration in the region of a mutant RHO$^{T4R/+}$ retina treated with AAV2/5-sc-HOP-RHO820-H1-shRNA820 at $5\times10^{11}$/vg/ml titer. FIG. 20A shows en face cSLO composite showing 2 weeks post light exposure the retinal region (border demarcated by white arrows) that was protected from degeneration. Light gray arrow indicates the location within the treated area of the OCT B scans shown in FIG. 20B, dark gray arrow indicates the location within the untreated area of the OCT B scans shown in FIG. 20C. FIG. 20B shows OCT B scans within the treated area before injection, 11 weeks post injection, and 13 weeks post injection/2 weeks post light exposure. ONL thickness is preserved throughout the treated area at both time-points following the injection of the viral vector. FIG. 20C shows OCT B scans within the untreated area before injection, 11 weeks post injection, and 13 weeks post injection/2 weeks post light exposure. ONL is preserved up to 11 weeks post injection but is completely lost 2 weeks after light exposure. FIG. 21 shows topographic maps of ONL thickness from a two RHO$^{T4R/+}$ treated with AAV2/5-sc-HOP-RHO820-H1-shRNA820 at $5\times10^{11}$/vg/ml titer showing protection from light-induced retinal degeneration.

Evaluation by Histology and Immunohistochemistry of Photoreceptor Protection from Light-Induced Damage in Eyes of Mutant RHO$^{T4R/+}$ Dogs Injected with AAV2/5-Sc-HOP-RHO820-H1-shRNA820 at $5\times10^{11}$/vg/ml Titer:

Eyes from the same mutant RHOT4R/+ dogs listed in above that were subretinally injected with AAV2/5-sc-HOP-RHO820-H1-shRNA820 at $5\times10^{11}$/vg/ml titer and subsequently light exposed (at 11 weeks post injection) to 1 min duration of white light at an intensity (corneal irradiance of 1 mW/cm2) were examined. This dose of light was previously shown to cause acute retinal degeneration in RHO T4R mutant but not in WT dogs.

Immunohistochemistry was used to assess the level of protection conferred by AAV2/5-sc-HOP-RHO820-H1-shRNA820 in the treated/bleb area. The surrounding non bleb/untreated regions were used as an internal control for each eye. Antibodies directed against rhodopsin (RHO), and human cone arrestin (hCA) were used to assess the integrity of rod outer segments and cone morphology. Two weeks post light-exposure excellent preservation of ONL thickness was achieved in the bleb/treated area of eyes injected with the $5\times10^{11}$ vg/ml titers. In addition and contrary to what was seen when treating retina with the knockdown reagent shRNA820, preservation of rod outer segments was achieved with the AAV2/5-sc-HOP-RHO820-H1-shRNA820 construct.

Figure 22:
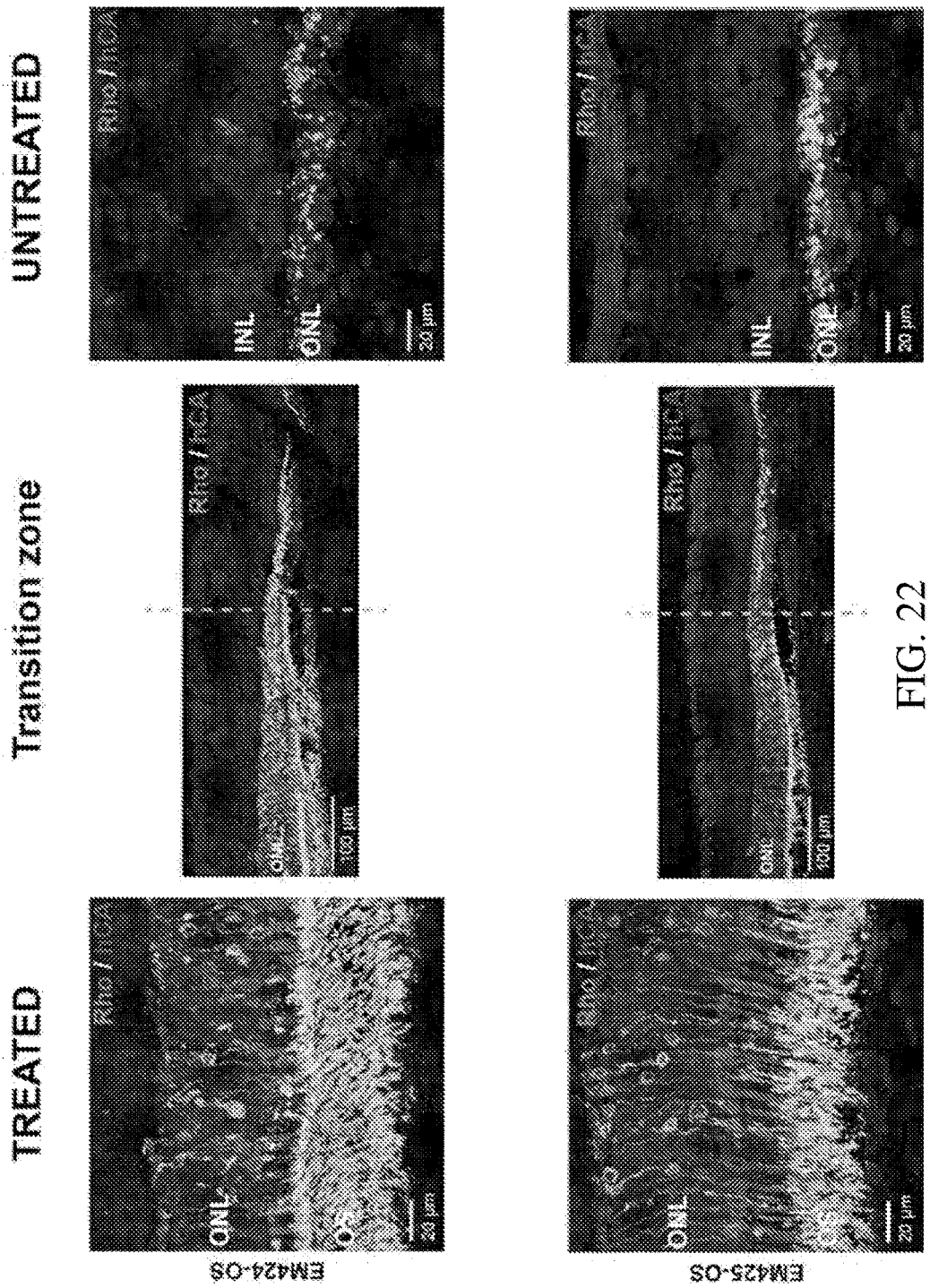
FIG. 22 shows immunohistochemistry (Rhodopsin was stained in green and appears as light staining in the panels of FIG. 22; human cone arrestin was stained in red and appears as gray staining in the panels of FIG. 22) in the treated, transition zone and untreated areas of mutant $RHO^{T4R/+}$ retinas subretinally injected with AAV2/5-sc-HOP-RHO820-H1-shRNA820 at $5 \times 10^{11}$/vg/ml titer.

FIG. 22 shows immunohistochemistry (Rhodopsin was stained in green and appears as the lighter staining in the panels of FIG. 22; human cone arrestin was stained in red appears as the gray staining in the panels of FIG. 22) in the treated, transition zone and untreated areas of mutant RHO$^{T4R/+}$ retinas subretinally injected with AAV2/5-sc-HOP-RHO820-H1-shRNA820 at $5\times10^{11}$/vg/ml titer. In the treated area there is complete preservation of the outer nuclear layer (ONL) thickness, and of rod outer segments (OS), while in the untreated area all rods have been lost and the ONL is reduced to a single row of cone cell bodies. A clear boundary between treated and untreated areas is seen at the transition zone.

Complete knockdown of canine RHO RNA and protein (by western blot) is achieved with AAV2/5-sc-HOP-RHO820-H1-shRNA820 at a viral titer $5\times10^{11}$ vg/ml. Efficient replacement with hardened RHO820 is achieved both at the mRNA (118-130%) and protein (30-33%) levels when compared to normal RHO levels in the canine retina. Complete protection of the outer nuclear layer (ONL) which contains the cells bodies of the photoreceptors is achieved with AAV2/5-sc-HOP-RHO820-H1-shRNA820 at a viral titer $5\times10^{11}$ vg/ml. Complete preservation of rod outer segments as a result of efficient RHO replacement with RHO820 is achieved with AAV2/5-sc-HOP-RHO820-H1-shRNA820 at a viral titer $5\times10^{11}$ vg/ml.

REFERENCES

1. Mao H, Gorbatyuk M S, Rossmiller B, Hauswirth W W, Lewin A S. Long-Term Rescue of Retinal Structure and Function by Rhodopsin RNA Replacement with a Single Adeno-Associated Viral Vector in P23H RHO Transgenic Mice. *Hum Gene Ther.* 2012; 23:356-366.
2. Rossmiller B, Mao H, Lewin AS. Gene therapy in animal models of autosomal dominant retinitis pigmentosa. *Mol Vis.* 2012; 18:2479-2496.
3. Gorbatyuk M, Justilien V, Liu J, Hauswirth W W, Lewin A S. Suppression of mouse rhodopsin expression in vivo by AAV mediated siRNA delivery. *Vision Res.* 2007; 47:1202-1208.
4. Khvorova A, Reynolds A, Jayasena S D. Functional siRNAs and miRNAs exhibit strand bias. *Cell.* 2003; 115:209-216.
5. Reynolds A, Leake D, Boese Q, Scaringe S, Marshall W S, Khvorova A. Rational siRNA design for RNA interference. *Nat Biotechnol.* 2004; 22:326-330.
6. Jensen S M R, Schmitz A, Pedersen F S, Kjems J+, Bramsen J B. Functional Selection of shRNA Loops from Randomized Retroviral Libraries. *PLoS ONE.* 2012; 7:e43095.
7. Zhou H, Xia X G, Xu Z. An RNA polymerase II construct synthesizes short-hairpin RNA with a quantitative indicator and mediates highly efficient RNAi. *Nucleic Acids Res.* 2005; 33:e62-e70.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. A synthetic ribonucleic acid (RNA) molecule comprising:

a) a sense strand of sequence
   CUGCCUACAUGUUUCUGCU (SEQ ID NO: 1)
   and
   an antisense strand of sequence
   AGCAGAAACAUGUAGGCAG; (SEQ ID NO: 2)

b) a sense strand of sequence
   CCUACAUGUUUCUGCUGAU (SEQ ID NO: 3)
   and
   an antisense strand of sequence
   AUCAGCAGAAACAUGUAGG; (SEQ ID NO: 4)

c) a sense strand of sequence
   GCAUGGUCAUCAUCAUGGU (SEQ ID NO: 5)
   and
   an antisense strand of sequence
   ACCAUGAUGAUGACCAUGC; (SEQ ID NO: 6)
   or d) a sense strand of sequence
   GUGGCAUUCUACAUCUUCA (SEQ ID NO: 7)
   and
   an antisense strand of sequence
   UGAAGAUGUAGAAUGCCAC. (SEQ ID NO: 8)

2. The synthetic RNA molecule of claim 1, wherein the RNA is a small interfering RNA (siRNA).

3. The synthetic RNA molecule of claim 1, wherein the RNA is a small hairpin RNA (shRNA).

4. The shRNA of claim 3, having a loop that comprises RNA of sequence UCAAGAG (SEQ ID NO: 9) or RNA of sequence UGUGCUU (SEQ ID NO: 10).

5. The synthetic RNA molecule of claim 1, wherein the RNA is an artificial micro RNA (miRNA).

6. The artificial miRNA of claim 5, wherein the artificial miRNA comprises RNA of sequence UGCU-GUUGACAGUGAGCGA$(X)_n$UAGUGAAGC-CACAGAUGUA$(Y)_n$CUGCCUACUGCCU CGGA (SEQ ID NO: 19), and wherein:
a) $(X)_n$ comprises SEQ ID NO: 1 and $(Y)_n$ comprises SEQ ID NO: 2;
b) $(X)_n$ comprises SEQ ID NO: 3 and $(Y)_n$ comprises SEQ ID NO: 4;
c) $(X)_n$ comprises SEQ ID NO: 5 and $(Y)_n$ comprises SEQ ID NO: 6; or
d) $(X)_n$ comprises SEQ ID NO: 7 and $(Y)_n$ comprises SEQ ID NO: 8.

7. The synthetic RNA of claim 1, further comprising an unpaired overhang sequence at the 5' and/or 3' end.

8. The synthetic RNA of claim 7, wherein the unpaired overhang sequence comprises a sequence of repeating bases.

9. The synthetic RNA of claim 8, wherein the sequence of repeating bases comprises repeating uracil (U) bases.

10. The synthetic RNA of claim 9, wherein the unpaired overhang sequence is UU.

11. A composition comprising the synthetic RNA of claim 1.

12. The composition of claim 11, further comprising one or more physiologically acceptable carriers and/or one or more physiologically acceptable adjuvants.

13. A vector encoding:
a) the shRNA of claim 3; or
b) the artificial miRNA of claim 5.

14. The vector of claim 13, wherein the shRNA is selected from any one of SEQ ID NOs: 11-18.

15. The vector of claim 13, wherein the vector is an expression plasmid.

16. The vector of claim 13, wherein the vector is a viral vector.

17. The viral vector of claim 16, wherein the viral vector comprises an adeno-associated viral vector.

18. A method of decreasing RHO expression in a subject, the method comprising administering to the subject the composition of claim 11.

19. A method of treating retinitis pigmentosa (RP) in a subject, the method comprising administering to the subject both:
a) the composition of claim 11; and
b) a recombinant RHO gene that does not contain a sequence targeted by an interfering RNA of the composition of a).

20. The method of claim 19, wherein the recombinant RHO gene is delivered using an rAAV.

21. The method of claim 20, wherein the interfering RNA and the recombinant RHO gene are delivered using the same rAAV.

22. The method of claim 21, wherein the interfering RNA and the recombinant RHO gene are both under expression control of a single promoter sequence.

23. The method of claim 22, wherein the interfering RNA and the recombinant RHO gene are each under expression control of independent promoter sequences.

24. The method of claim 23, wherein the interfering RNA is shRNA, and wherein the shRNA is under expression control of an RNA polymerase III promoter.

25. The method of claim 23, wherein the interfering RNA is an artificial miRNA, and wherein the artificial miRNA is under expression control of an RNA polymerase II promoter.

26. The method of claim 24, wherein the recombinant RHO gene is under expression control of a constitutive or inducible promoter.

27. The method of claim 19, wherein the subject is a mammal.

28. The method of claim 27, wherein the mammal is a rodent or a dog.

29. The method of claim 27, wherein the mammal is a human.

30. A viral vector encoding the shRNA of claim 3 and a recombinant RHO sequence comprising a nucleotide sequence that comprises SEQ ID NO: 42.

31. The viral vector of claim 17, wherein the viral vector is an AAV2, AAV2/1, AAV2/5, AAV2/8 or AAV2/9 vector.

32. The viral vector of claim 30, wherein the vector comprises AAV2/5-sc-HOP-RHO$_{820}$-H1-shRNA$_{820}$.

33. The viral vector of claim 31, wherein the vector encodes:
a) a sense strand of sequence GUGGCAUUCUACAUC-UUCA (SEQ ID NO: 7) and an antisense strand of sequence UGAAGAUGUAGAAUGCCAC (SEQ ID NO: 8);
b) a recombinant RHO sequence comprising a nucleotide sequence that comprises SEQ ID NO: 42; wherein the vector is an AAV2/5 vector.

34. The method of claim 19, wherein the retinitis pigmentosa is autosomal dominant retinitis pigmentosa (adRP).

\* \* \* \* \*

UNITED STATES PATENT AND TRADEMARK OFFICE
CERTIFICATE OF CORRECTION

| | | |
|---|---|---|
| PATENT NO. | : 11,118,185 B2 | Page 1 of 1 |
| APPLICATION NO. | : 16/081307 | |
| DATED | : September 14, 2021 | |
| INVENTOR(S) | : Lewin et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 480 days.

Signed and Sealed this
Thirty-first Day of January, 2023

*Katherine Kelly Vidal*

Katherine Kelly Vidal
*Director of the United States Patent and Trademark Office*

SEQUENCE LISTING

<160> NUMBER OF SEQ ID NOS: 42

<210> SEQ ID NO 1
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1
cugccuacau guuucugcu                    19

<210> SEQ ID NO 2
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 2
agcagaaaca uguaggcag                    19

<210> SEQ ID NO 3
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 3
ccuacauguu ucugcugau                    19

<210> SEQ ID NO 4
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 4
aucagcagaa acauguagg                    19

<210> SEQ ID NO 5
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 5
gcauggucau caucauggu                    19

<210> SEQ ID NO 6
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 6
accaugauga ugaccaugc                    19

<210> SEQ ID NO 7
<211> LENGTH: 19
<212> TYPE: RNA
<213> ORGANISM: Artificial Sequence

```
<220> FEATURE:
<223> OTHER INFORMATION: Synthetic Polynucleotide

<400> SEQUENCE: 7
guggcauucu acaucuuca                                                    19

<210> SEQ ID NO 8
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 8
ugaagaugua gaaugccac                                                    19

<210> SEQ ID NO 9
<211> LENGTH: 7
<212> TYPE: RNA
<213> ORGANISM: Artificial Sequence
<220> FEATURE:
<223> OTHER INFORMATION: Synthetic Polynucleotide

<400> SEQUENCE: 9 ucaagag                                                                  7

<210> SEQ ID NO 10
<211> LENGTH: 7
<212> TYPE: RNA
<213> ORGANISM: Artificial Sequence
<220> FEATURE:
<223> OTHER INFORMATION: Synthetic Polynucleotide

<400> SEQUENCE: 10 ugugcuu                                                                  7

<210> SEQ ID NO 11
<211> LENGTH: 45
<212> TYPE: RNA
<213> ORGANISM: Artificial Sequence
<220> FEATURE:
<223> OTHER INFORMATION: Synthetic Polynucleotide

<400> SEQUENCE: 11
cugccuacau guuucugcuu caagagagca gaaacaugua ggcag                       45

<210> SEQ ID NO 12
<211> LENGTH: 45
<212> TYPE: RNA
<213> ORGANISM: Artificial Sequence
<220> FEATURE:
<223> OTHER INFORMATION: Synthetic Polynucleotide

<400> SEQUENCE: 12
cugccuacau guuucugcuu gugcuuagca gaaacaugua ggcag                       45

<210> SEQ ID NO 13
<211> LENGTH: 45
<212> TYPE: RNA
<213> ORGANISM: Artificial Sequence
<220> FEATURE:
<223> OTHER INFORMATION: Synthetic Polynucleotide

<400> SEQUENCE: 13
ccuacauguu ucugcugauu caagagauca gcagaaacau guagg                       45
```

<210> SEQ ID NO 14
<211> LENGTH: 45
<212> TYPE: RNA
<213> ORGANISM: Artificial Sequence
<220> FEATURE:
<223> OTHER INFORMATION: Synthetic Polynucleotide

<400> SEQUENCE: 14
ccuacauguu ucugcugauu gugcuuauca gcagaaacau guagg          45

<210> SEQ ID NO 15
<211> LENGTH: 45
<212> TYPE: RNA
<213> ORGANISM: Artificial Sequence
<220> FEATURE:
<223> OTHER INFORMATION: Synthetic Polynucleotide

<400> SEQUENCE: 15
gcauggucau caucaugguu caagagacca ugaugaugac caugc          45

<210> SEQ ID NO 16
<211> LENGTH: 45
<212> TYPE: RNA
<213> ORGANISM: Artificial Sequence
<220> FEATURE:
<223> OTHER INFORMATION: Synthetic Polynucleotide

<400> SEQUENCE: 16
gcauggucau caucaugguu gugcuuacca ugaugaugac caugc          45

<210> SEQ ID NO 17
<211> LENGTH: 45
<212> TYPE: RNA
<213> ORGANISM: Artificial Sequence
<220> FEATURE:
<223> OTHER INFORMATION: Synthetic Polynucleotide

<400> SEQUENCE: 17
guggcauucu acaucuucau caagagugaa gauguagaau gccac          45

<210> SEQ ID NO 18
<211> LENGTH: 45
<212> TYPE: RNA
<213> ORGANISM: Artificial Sequence
<220> FEATURE:
<223> OTHER INFORMATION: Synthetic Polynucleotide

<400> SEQUENCE: 18
guggcauucu acaucuucau gugcuuugaa gauguagaau gccac          45

<210> SEQ ID NO 19
<211> LENGTH: 93
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (20)..(38)
<223> OTHER INFORMATION: n is a, c, g, u, or absent
<220> FEATURE:
<221> NAME/KEY: misc_feature
<222> LOCATION: (58)..(76)
<223> OTHER INFORMATION: n is a, c, g, u, or absent

<400> SEQUENCE: 19
ugcuguugac agugagcgan nnnnnnnnnn nnnnnnnnua gugaagccac agauguannn          60
nnnnnnnnnn nnnnnncugc cuacugccuc gga    93

```
<210> SEQ ID NO 20
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 20
```
cugccuacau guuucugcuu caagagagca gaaacaugua ggcaguu    47

```
<210> SEQ ID NO 21
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 21
```
cugccuacau guuucugcuu gugcuuagca gaaacaugua ggcaguu    47

```
<210> SEQ ID NO 22
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 22
```
ccuacauguu ucugcugauu caagagauca gcagaaacau guagguu    47

```
<210> SEQ ID NO 23
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 23
```
ccuacauguu ucugcugauu gugcuuauca gcagaaacau guagguu    47

```
<210> SEQ ID NO 24
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 24
```
gcauggucau caucaugguu caagagacca ugaugaugac caugcuu    47

```
<210> SEQ ID NO 25
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 25
```
gcauggucau caucaugguu gugcuuacca ugaugaugac caugcuu    47

```
<210> SEQ ID NO 26
<211> LENGTH: 47
<212> TYPE: RNA
```

```
<213> ORGANISM: Artificial Sequence
<220> FEATURE:
<223> OTHER INFORMATION: Synthetic Polynucleotide

<400> SEQUENCE: 26
guggcauucu acaucuucau caagagugaa gauguagaau gccacuu                    47

<210> SEQ ID NO 27
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 27
guggcauucu acaucuucau gugcuuugaa gauguagaau gccacuu                    47

<210> SEQ ID NO 28
<211> LENGTH: 89
<212> TYPE: RNA
<213> ORGANISM: Artificial Sequence
<220> FEATURE:
<223> OTHER INFORMATION: Synthetic Polynucleotide

<400> SEQUENCE: 28
ugcuguugac agugagcgac ugccuacaug uuucugcugu gaagccacag augagcagaa      60
acauguaggc agcugccuac ugccucgga                                        89

<210> SEQ ID NO 29
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 29
ccgccuauau guuccuccu                                                   19

<210> SEQ ID NO 30
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 30
agcagaaaca uguaggcag                                                   19

<210> SEQ ID NO 31
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 31
ccgccuacau guuucugcu                                                   19

<210> SEQ ID NO 32
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 32
```

-continued

```
gcauggugau aauaauggu                                               19

<210> SEQ ID NO 33
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 33
accaugauga ugaccaugc                                               19

<210> SEQ ID NO 34
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 34
gcauggucau caucauggu                                               19

<210> SEQ ID NO 35
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 35
guggcuuuuu auauauuca                                               19

<210> SEQ ID NO 36
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 36
ugaagaugua gaaugccac                                               19

<210> SEQ ID NO 37
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 37
guggcauucu acaucuuca                                               19

<210> SEQ ID NO 38
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 38
ccuauauguu ccuccucau                                               19

<210> SEQ ID NO 39
<211> LENGTH: 19
<212> TYPE: RNA
```

<213> ORGANISM: Artificial Sequence
<220> FEATURE:
<223> OTHER INFORMATION: Synthetic Polynucleotide

<400> SEQUENCE: 39
aucagcagaa acauguagg                                                    19

<210> SEQ ID NO 40
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 40
ccuacauguu ucugcugau                                                    19

<210> SEQ ID NO 41
<211> LENGTH: 13706
<212> TYPE: DNA
<213> ORGANISM: Homo sapiens

<400> SEQUENCE: 41 gtggggacc aggagaaaga aagccaagga agaggaggag gaggaggaga aggaggagaa        60
ggatgctgac ctagcagctc ctctcacagc agctcctctc ttgcagaggc tgaagagcga     120
tttgtgccct gcaagctaag cccctaatcc accgaggcaa aggcaaagcc cctagccggg     180
ctcccgaggg ctgggactcg ggtgccccaa gatggctgca tccagccatc ttggcttaga     240
aagcccccca catgccagct tggccaacac ccacaccatg ggtttctctg gactgcccga     300
cacaaggtgt gggtgctggc caggcctgtg ttcaaatccc agctctgcag aggaactttg     360
accctgcata ccccagattc ctcagtggtc agtggggagt tagaccctct tcataggggg     420
caggaggagt tgttcattca ttcaacaaat gtttattgaa cacctcctat gggttgtgag     480
ctcagaggca gcgatgaaca ggccaggctg gtcctgcatt ctagaaatag atgggaagtc     540
agtcaataag tagacaaatg aggccaggtg tggtggcatg cctgtagacc cagttactcg     600
ggatgctgag gtaggaggat cacttgagcc taggacagga attcaaggct gcagtaagct     660
atgattgcgc cactgcactc cagcctgggc aacagagcaa gactcatctc taaaaaacat     720
ttaaaaattg ttttaagaag acaaatgaga tagtcgctga tggtaatgac tgtgtaaaaa     780
ctgaacatgg ctgggtgtgg ttgctcacac ctataatctc agcactttgg gaggctgaga     840
ttacagcctc ccaagtggct cccaaggcag gaggatcact tgagcctggg agttagagaa     900
cagcttggac aatataggga gagcccaact ctacaaaaat gaaaataaat tagccaggca     960
tggtggcaca caccaatggt cccagctact caggggttga ggtggtggac cgcttgagcc    1020
caggaggttg aggctgcagt gagccatgat catgccgctg cactccaacc tgagtcacag    1080
agtgataccc tgtctcaaaa aacaataggc caggtgtggt ggctcacgcc tgtaaccccca   1140 gcactttggg aggccgaggc ggatggatca cttgagatca ggagttagag accagcctgg    1200
ctaacatggc aaaatcctgt ctgtactaaa aatataaaaa ttagccaggc atggcagtac    1260
atgcctgtag tcctggttac ttgggaggct aaggcaggag aatcgcttga acccaggaag    1320
aggaggttgc agtgagccaa gatcacacca ctgcactcca gcttgggtga cagagtgaga    1380
ccctgtctca aaacagctaa acctggtggg ggtgcctggt gtgtaggatg gtcagggtg     1440 gtctctccaa ggacatgagt gtgagcggag acctgaagga gactcaggaa gagattaata    1500
ctgtcagcaa caaatatatt gatcacttac aagcactccc aataatccta ttaggtaggc    1560

```
actattatca ttcccatttt acagagtgga gaaccgaagc acactctcgg gagggcgggg    1620
tagctggctg cacccaggct gtgtagcctc agtccagatg taagggtggg tggaaaagag    1680
ccttgcccaa tgagggagaa cagtgaaacc aaggccatag ggtctaaaga ttcacgaacc    1740
aggctctcat ggagaaagca ggtgaggttt actgtataga tgggtgtgcc cctaccccac    1800
actgaggctt cctcgtctga gcaaactgag gcccagagag gggaaggaag caggactacc    1860
atggtgactc aaagaccagc tagaatccag cctcctctcc tcgaggcttc cactgcccca    1920
cgccaggcct gtgtgactca gtctagggcc tttccattac cccagctaaa cctttcttta    1980
gtcatttata ccatggtgtg aatggctggc tggtctttcc tgagagctat ctttgatgag    2040
gggagggagg catagccagg tttgggaagc tgatacccca ggaagcccag ttgactgtgt    2100
gggttatagc ccaggctgtc actgatttgt aacgggacct gagcaactct gcagagctag    2160
gcctcagtct tttcatctgc aaaatggata tagcagagat ggtcagagta ggtgacttcg    2220
aatgaccctt ccagctcact atgagtctgt tttcctgaac aaagagcatt ttttgtttaa    2280
aaaaaatttt cttgggccgg acacggtggt tcactcctat aatcctggca ctttgggagg    2340
ccgaggaggg tggatcgctt gagccaggag ttcaggacca gcctgggcaa catagcgaga    2400
ctccacccct acaaaaaata caaaaactag tggtgtgcac ttgtggtccc agctactcag    2460
gaggctgagg tgagaggatc gcttgagccc aggaggcaga ggctacagtg agctatgatt    2520
gtggcactgc actccagcct gggcgacaga gaccttgtct caaaactttt tttttcttcg    2580
tcaagcttta cagaataaag agcactgtca cctcagtgat ggctgttagt tccccatcac    2640
cagggctcca tgaggttgca attgtgaaac tcacaaagga ggaacctgag acagagaggg    2700
gaagtactga gatcatctag gtccattccc ccactcactc gttcattcaa caaatattca    2760
ggagcacctt ctaggtgcca ggccctggag acacatcagt gaacaaaaca gacatcatcc    2820
cacctctttc cactacaggc caagcaccat gctggtctct gggaaccctg ttgtgagcaa    2880
gacagaccca ggcttaccct tgtggactca tgttacaggc agggagacgg gcacaaaaca    2940
caaataaaaa gcttccatgc tgtcagaagc actatgcaaa aagcaagatg ctgaggtact    3000
gctaagctgt gtgggatggg ggctcagccc ggccagggag gggccagttg tgggtcagtc    3060
ttgacccaag gcatccagga caccctcctt ctggccatga gggtccacgt cagaatcaaa    3120
ccctcacctt aacctcatta gcgttgggca taatcaccag gccaagcgcc ttaaactacg    3180
agaggcccca tcccacccgc cctgccttag ccctgccacg tgtgccaaac gctgttagac    3240
ccaacaccac ccaggccagg tagggggctg gagcccaggt gggctgcagg gaaggggggca    3300 ctcttctgag cagacagatc tgggaatcct gggtgggaag agagacagtg agagagagat    3360
taagggatat ttcccaggca tcagggcttt gcactctcag gggtccttcc gcctggatgt    3420
ccttcccctg aagcttcctc ctgttgttcc gttctcagct caagctccag cttctcagag    3480
aagcctcctg tgttgggagt ggctgcgact gaactgtccc tactgttatt cgctcttcta    3540
tttgtttgtg gtccctgtgc cccctcaccc cacaaaaaca ctggcttctt gtgagcagga    3600
gcttgctctt tcgtgtaccc tgtgtgtccc caaggaccaa gcaccttgtc tgggccacag    3660
taggtgctca atacacatgt tggctggaca gtggtcactg agcggccgca cgtcgggcac    3720
tctcagcact tgcacaggcc gccccagaca ccccacttca ttcctgggag gtgtcatcat    3780
gttgcttgga cgacggggag agggggacct gccagtgttg gcctccattt тccccагтс    3840 atctgccccc aaggctctga ctactttctt tctcacggta catcctgcta ttctggaatc    3900
```

-continued

```
ggccctcgtg gggccacctg gtacatggca tttgaggccc tcgtggctga ttaggcctcc    3960
cccaacagtg ccctgtctgc tgcctccagg gccagcctcc ccttcagact ggagtccccct    4020
gaagggttct gccctccc tgctctggta gccccctcca tcctccctcc ctccactcca    4080
tctttggggg catttgagtc acctttctac accagtgatc tgcccaagcc actgctcact    4140
ttcctctgga taaagccagg ttccccggcc tagcgttcaa gacccattac aactgccccc    4200
agcccagatc ttccccacct agccacctgg caaactgctc cttctctcaa aggcccaaac    4260
atggcctccc agactgcaac ccccaggcag tcaggccctg tctccacaac ctcacagcca    4320
ccctggacgg aatctgcttc ttcccacatt tgagtcctcc tcagccctg agctcctctg    4380
ggcagggctg tttctttcca tctttgtatt cccaggggcc tgcaaataaa tgtttaatga    4440
acgaacaaga gagtgaattc caattccatg caacaaggat tgggctcctg ggccctaggc    4500
tatgtgtctg gcaccagaaa cggaagctgc aggttgcagc ccctgccctc atggagctcc    4560
tcctgtcaga ggagtgtggg gactggatga ctccagaggt aacttgtggg ggaacgaaca    4620
ggtaaggggc tgtgtgacga gatgagagac tgggagaata aaccagaaag tctctagctg    4680
tccagaggac atagcacaga ggcccatggt ccctatttca aacccaggcc accagactga    4740
gctgggacct tgggacagac aagtcatgca gaagttaggg gaccttctcc tccctttcc    4800
tggatcctga gtacctctcc tccctgacct caggcttcct cctagtgtca ccttggcccc    4860
tcttagaagc caattaggcc ctcagtttct gcagcgggga ttaatatgat tatgaacacc    4920
cccaatctcc cagatgctga ttcagccagg agcttaggag ggggaggtca ctttataagg    4980
gtctggggg gtcagaaccc agagtcatcc agctggagcc ctgagtggct gagctcaggc    5040
cttcgcagca ttcttgggtg ggagcagcca cgggtcagcc acaagggcca cagccatgaa    5100
tggcacagaa ggccctaact tctacgtgcc cttctccaat gcgacgggtg tggtacgcag    5160
ccccttcgag tacccacagt actacctggc tgagccatgg cagttctcca tgctggccgc    5220
ctacatgttt ctgctgatcg tgctgggctt cccatcaac ttcctcacgc tctacgtcac    5280
cgtccagcac aagaagctgc gcacgcctct caactacatc ctgctcaacc tagccgtggc    5340
tgacctcttc atggtcctag gtggcttcac cagcaccctc tacacctctc tgcatggata    5400
cttcgtcttc gggcccacag gatgcaattt ggagggcttc tttgccaccc tgggcggtat    5460
gagccgggtg tgggtggggt gtgcaggagc ccgggagcat ggaggggtct gggagagtcc    5520
cgggcttggc ggtggtggct gagaggcctt ctcccttctc ctgtcctgtc aatgttatcc    5580
aaagccctca tatattcagt caacaaacac cattcatggt gatagccggg ctgctgtttg    5640
tgcagggctg gcactgaaca ctgccttgat cttatttgga gcaatatgcg cttgtctaat    5700
ttcacagcaa gaaaactgag ctgaggctca aagaagtcaa gcgccctgct ggggcgtcac    5760
acagggacgg gtgcagagtt gagttggaag cccgcatcta tctcgggcca tgtttgcagc    5820
accaagcctc tgtttccctt ggagcagctg tgctgagtca gacccaggct gggcactgag    5880
ggagagctgg gcaagccaga cccctcctct ctggggcc aagctcaggg tgggaagtgg    5940
attttccatt ctccagtcat tgggtcttcc ctgtgctggg caatgggctc ggtcccctct    6000
ggcatcctct gcctccctc tcagcccctg tcctcaggtg ccctccagc ctccctgccg    6060
cgttccaagt ctcctggtgt tgagaaccgc aagcagccgc tctgaagcag ttccttttg    6120
ctttagaata atgtcttgca tttaacagga aaacagatgg ggtgctgcag gataacaga    6180
tcccacttaa cagagaggaa aactgaggca gggagaggga aagagactca tttagggatg    6240
tggccaggca gcaacaagag cctaggtctc ctggctgtga tccaggaata tctctgctga    6300
```

```
gatgcaggag gagacgctag aagcagccat tgcaaagctg ggtgacgggg agagcttacc    6360
gccagccaca agcgtctctc tgccagcctt gccctgtctc ccccatgtcc aggctgctgc    6420
ctcggtccca ttctcaggga atctctggcc attgttgggt gtttgttgca ttcaataatc    6480
acagatcact cagttctggc cagaaggtgg gtgtgccact tacgggtggt tgttctctgc    6540
agggtcagtc ccagtttaca aatattgtcc ctttcactgt taggaatgtc ccagtttggt    6600
tgattaacta tatggccact ctccctatgg aacttcatgg ggtggtgagc aggacagatg    6660
tctgaattcc atcatttcct tcttcttcct ctgggcaaaa cattgcacat tgcttcatgg    6720
ctcctaggag aggcccccac atgtccgggt tatttcattt cccgagaagg gagagggagg    6780
aaggactgcc aattctgggt ttccaccacc tctgcattcc ttcccaacaa ggaactctgc    6840
cccacattag gatgcattct tctgctaaac acacacacac acacacacac acacaacaca    6900
cacacacaca cacacacaca cacacacaca aaactcccta ccgggttccc agttcaatcc    6960 tgacccctg atctgattcg tgtcccttat gggcccagag cgctaagcaa ataacttccc    7020
ccattccctg gaatttcttt gcccagctct cctcagcgtg tggtccctct gccccttccc    7080
cctcctccca gcaccaagct ctctccttcc ccaaggcctc ctcaaatccc tctcccactc    7140
ctggttgcct tcctagctac cctctccctg tctaggggga agtgcaccct ccttaggcag    7200
tggggtctgt gctgaccgcc tgctgactgc cttgcaggtg aaattgccct gtggtccttg    7260
gtggtcctgg ccatcgagcg gtacgtggtg gtgtgtaagc ccatgagcaa cttccgcttc    7320
ggggagaacc atgccatcat gggcgttgcc ttcacctggg tcatggcgct ggcctgcgcc    7380 gcaccccac tcgccggctg gtccaggtaa tggcactgag cagaagggaa gaagctccgg    7440
gggctctttg tagggtcctc cagtcaggac tcaaacccag tagtgtctgg ttccaggcac    7500
tgaccttgta tgtctcctgg cccaaatgcc cactcagggt aggggtgtag ggcagaagaa    7560
gaaacagact ctaatgttgc tacaagggct ggtcccatct cctgagcccc atgtcaaaca    7620
gaatccaaga catcccaacc cttcaccttg gctgtgcccc taatcctcaa ctaagctagg    7680
cgcaaattcc aatcctcttt ggtctagtac cccgggggca gcccctcta accttgggcc    7740 tcagcagcag gggaggccac accttcctag tgcaggtggc catattgtgg ccccttggaa    7800
ctgggtccca ctcagcctct aggcgattgt ctcctaatgg ggctgagatg agacacagtg    7860
gggacagtgg tttggacaat aggactggtg actctggtcc ccagaggcct catgtccctc    7920
tgtctccaga aaattcccac tctcacttcc cttcctcct cagtcttgct agggtccatt    7980
tcttacccct tgctgaattt gagcccaccc cctggacttt ttccccatct tctccaatct    8040
ggcctagttc tatcctctgg aagcagagcc gctggacgct ctgggtttcc tgaggcccgt    8100
ccactgtcac caatatcagg aaccattgcc acgtcctaat gacgtgcgct ggaagcctct    8160
agtttccaga agctgcacaa agatccctta gatactctgt gtgtccatct ttggcctgga    8220
aaatactctc accctggggc taggaagacc tcggtttgta caaacttcct caaatgcaga    8280
gcctgagggc tctccccacc tcctcaccaa ccctctgcgt ggcatagccc tagcctcagc    8340
gggcagtgga tgctggggct gggcatgcag ggagaggctg ggtggtgtca tctggtaacg    8400
cagccaccaa acaatgaagc gacactgatt ccacaaggtg catctgcatc cccatctgat    8460
ccattccatc ctgtcaccca gccatgcaga cgtttatgat ccccttttcc agggagggaa    8520
tgtgaagccc cagaaagggc cagcgctcgg cagccacctt ggctgttccc aagtccctca    8580
caggcagggt ctccctacct gcctgtcctc aggtacatcc ccgagggcct gcagtgctcg    8640
```

-continued

```
tgtggaatcg actactacac gctcaagccg gaggtcaaca acgagtctttt tgtcatctac    8700
atgttcgtgg tccacttcac catccccatg attatcatct ttttctgcta tgggcagctc    8760
gtcttcaccg tcaaggaggt acgggccggg gggtgggcgg cctcacggct ctgagggtcc    8820
agcccccagc atgcatctgc ggctcctgct ccctggagga gccatggtct ggacccgggt    8880
cccgtgtcct gcaggccgct gcccagcagc aggagtcagc caccacacag aaggcagaga    8940
aggaggtcac ccgcatggtc atcatcatgg tcatcgcttt cctgatctgc tgggtgccct    9000
acgccagcgt ggcattctac atcttcaccc accagggctc caacttcggt cccatcttca    9060
tgaccatccc agcgttcttt gccaagagcg ccgccatcta caaccctgtc atctatatca    9120
tgatgaacaa gcaggtgcct actgcgggtg ggagggcccc agtgcccag gccacaggcg    9180
ctgcctgcca aggacaagct acttcccagg gcaggggagg gggctccatc agggttactg    9240
gcagcagtct tgggtcagca gtcccaatgg ggagtgtgtg agaaatgcag attcctggcc    9300
ccactcagaa ctgctgaatc tcagggtggg cccaggaacc tgcatttcca gcaagccctc    9360
cacaggtggc tcagatgctc actcaggtgg agaagctcc agtcagctag ttctggaagc    9420
ccaatgtcaa agtcagaagg acccaagtcg ggaatgggat gggccagtct ccataaagct    9480
gaataaggag ctaaaaagtc ttattctgag gggtaaaggg gtaaagggtt cctcggagag    9540
gtacctccga ggggtaaaca gttgggtaaa cagtctctga agtcagctct gccattttct    9600
agctgtatgg ccctgggcaa gtcaatttcc ttctctgtgc tttggtttcc tcatccatag    9660
aaaggtagaa agggcaaaac accaaactct tggattacaa gagataattt acagaacacc    9720
cttggcacac agagggcacc atgaaatgtc acgggtgaca cagcccccctt gtgctcagtc    9780
cctggcatct ctaggggtga ggagcgtctg cctagcaggt tccctccagg aagctggatt    9840
tgagtggatg gggcgctgga atcgtgaggg gcagaagcag gcaaagggtc ggggcgaacc    9900
tcactaacgt gccagttcca agcacactgt gggcagccct ggccctgact caagcctctt    9960
gccttccagt tccggaactg catgctcacc accatctgct gcggcaagaa cccactgggt   10020
gacgatgagg cctctgctac cgtgtccaag acggagacga gccaggtggc cccggcctaa   10080
gacctgccta ggactctgtg gccgactata ggcgtctccc atcccctaca ccttccccca   10140
gccacagcca tcccaccagg agcagcgcct gtgcagaatg aacgaagtca cataggctcc   10200
ttaattttttt tttttttttt aagaaataat taatgaggct cctcactcac ctgggacagc   10260
ctgagaaggg acatccacca agacctactg atctggagtc ccacgttccc caaggccagc   10320
gggatgtgtg cccctcctcc tcccaactca tctttcagga acacgaggat tcttgctttc   10380
tggaaaagtg tccagctta gggataagtg tctagcacag aatggggcac acagtaggtg   10440
cttaataaat gctggatgga tgcaggaagg aatggaggaa tgaatgggaa gggagaacat   10500
atctatcctc tcagaccctc gcagcagcag caactcatac ttggctaatg atatggagca   10560
gttgtttttc cctccctggg cctcactttc ttctcctata aaatggaaat cccagatccc   10620
tggtcctgcc gacacgcagc tactgagaag accaaaagag gtgtgtgtgt gtctatgtgt   10680
gtgtttcagc actttgtaaa tagcaagaag ctgtacagat tctagttaat gttgtgaata   10740
acatcaatta atgtaactag ttaattacta tgattatcac ctcctgatag tgaacatttt   10800
gagattgggc attcagatga tggggtttca cccaaccttg ggcaggtttt ttaaaaatta   10860
gctaggcatc aaggccagac cagggctggg ggttgggctg taggcaggga cagtcacagg   10920
aatgcagaat gcagtcatca gacctgaaaa acaacactg ggggagggggg acggtgaagg   10980
ccaagttccc aatgagggtg agattgggcc tggggtctca cccctagtgt ggggccccag   11040
```

```
gtcccgtgcc tcccttccc aatgtggcct atggagagac aggcctttct ctcagcctct    11100
ggaagccacc tgctcttttg ctctagcacc tgggtcccag catctagagc atggagcctc    11160
tagaagccat gctcacccgc ccacatttaa ttaacagctg agtccctgat gtcatcctta    11220
tctcgaagag cttagaaaca aagagtggga aattccactg ggcctacctt ccttggggat    11280
gttcatgggc cccagtttcc agtttccctt gccagacaag cccatcttca gcagttgcta    11340
gtccattctc cattctggag aatctgctcc aaaaagctgg ccacatctct gaggtgtcag    11400
aattaagctg cctcagtaac tgctccccct tctccatata agcaaagcca gaagctctag    11460 cttacccag ctctgcctgg agactaaggc aaattgggcc attaaaagct cagctcctat    11520
gttggtatta acgtggtgg gttttgttgc tttcacactc tatccacagg atagattgaa    11580
actgccagct tccacctgat ccctgaccct gggatggctg gattgagcaa tgagcagagc    11640
caagcagcac agagtcccct ggggctagag gtggaggagg cagtcctggg aatgggaaaa    11700
accccaactt tggggtcata gaggcacagg taacccataa aactgcaaac aagctttgtc    11760
acctctcaga gcttccttat ctgcaaaaaa gaatcttaaa actgaccttg gctgggcaca    11820
gtggctcaca cctctaatcc cagcactttg ggaggccaag gtgggcagat cacgaggtca    11880
ggagtttgag accagcctga ccaacacggt gaaaccctgt ctctactaaa aatacaaaaa    11940
tcagctgggc atggtggcgc gtgcctgtaa tcccagctat tcagtgggct gaggcaggag    12000
aatcgcttga acctgggagg tggaggttgc agtgagccga gattgcgcca ctgcactcca    12060
gcctgagcaa cagagggaca gtctgtctcc aaacaaaaca aaacaaacaa acaaacaaac    12120
aaacaaacaa aaacaacaa caaaaaaacc acttgatcct aaggggatta gatgcgactg    12180
tggactttaa gtggccagcc tactgcctgg catgcagcag atgagactat ggcaatactg    12240
ggcttcagct cagagctggc cttactagag accctgtccc aaaggggaaa aggatggagc    12300
taaagctccc gagagtcacc ccctcctccg aggtgagaaa ggagggcagg agcatgagat    12360
agccgatcct cggtgccttg gtgaggctgg ggcaaatcat gctgggatct ctatcattgt    12420
ccctctttac tgtgactcac tagataatat cagtcaggat acttttggtc acaagtgata    12480
ggaaatccaa ctcatttggg ctgaagcaaa agggacacat tgttggctca catgaacaaa    12540
aagcccgggg cttcaggcac agggtatcac catgactgag atggggatta attctgtgat    12600
tggccaagtc taggtcacct gatcatacgt aactcattta tgcctgaggt tgcaattttt    12660
tggatttttg caatcagacc ttggcgatga ccttgagcag taggatataa ataactccca    12720
catgcttagc gttccaataa tggaatacta ggcatacgca ggtctaactg catcaccatg    12780
gctggaatgg ggattcatcc tctgattggt cagacctagg tcacatgctc accctgcagc    12840
ccaagcaggc tgaatgggga gaggtaggtt tcacaaagga aagcccaggt gctgttacct    12900
gaagtaggag ggcaggaggc agggtgagca gagccaacat caacccagag ggaatggaat    12960
ctaagttggt gttttctggg cacgtggctg accaggcct ccctccctca tcatctcagg    13020
gacatgaggg agaagattcc tatgggtggt cccgaaggtc tcacccttg ttttggatgc    13080 tgtgttgggc cagggtggca gtgggtggga cagtggcatc ttagctgccc tgacttgcag    13140
gcagcccatt ccagctcccc gccccaaccc caacccagcc cacttttttct gagaaatggt    13200 acatttgccc cagcctcatg tccagaggaa aattttactc taacaccaga acattctctg    13260
gtttgtcctg atagacaaga aagcctccac ctccttaatt tacaaatgac ttgacagctg    13320
cttcgtgggc acttgcatac ataaagagaa ggagctgctg ccttaagttg cagcaagttt    13380
```

| | | |
|---|---|---|
| ggccccacct catctccagg cagccagcag atgtacagag tgcctcttgg gtacaatggc | 13440 | |
| agctccattc aaccaaacct gagcaagctg accccatgcc agaatgcact ggggactcgg | 13500 | |
| agatgaattg gagcctagag accaagtctc taggctatga cctgggctgc tcacggcca | 13560 | |
| cagagctctg tcacgccaag ggagagatgc acccctgaaa gcctgaggtg ccccataagg | 13620 | |
| agagagtggg tgcccttccc aactatgtag cttcagggca agttctcttt ctttcttttt | 13680 | |
| ctttctttct ctttctttct ttcttt | 13706 | |

<210> SEQ ID NO 42
<211> LENGTH: 1134
<212> TYPE: DNA
<213> ORGANISM: Artificial Sequence
<220> FEATURE:
<223> OTHER INFORMATION: Synthetic Polynucleotide

<400> SEQUENCE: 42

| | |
|---|---|
| ccagctggag ccctgagtgg ctgagctcag gccttcgcag cattcttggg tgggagcagc | 60 |
| cacgggtcag ccacaagggc cacagccatg aatggcacag aaggccctaa cttctacgtg | 120 |
| cccttctcca atgcgacggg tgtggtacgc agccccttcg agtacccaca gtactacctg | 180 |
| gctgagccat ggcagttctc catgctggcc gcctacatgt ttctgctgat cgtgctgggc | 240 |
| ttccccatca acttcctcac gctctacgtc accgtccagc acaagaagct gcgcacgcct | 300 |
| ctcaactaca tcctgctcaa cctagccgtg gctgacctct tcatggtcct aggtggcttc | 360 |
| accagcaccc tctacacctc tctgcatgga tacttcgtct tcgggcccac aggatgcaat | 420 |
| ttggagggct tctttgccac cctgggcggt gaaattgccc tgtggtcctt ggtggtcctg | 480 |
| gccatcgagc ggtacgtggt ggtgtgtaag cccatgagca acttccgctt cggggagaac | 540 |
| catgccatca tgggcgttgc cttcacctgg gtcatggcgc tggcctgcgc cgcaccccca | 600 |
| ctcgccggct ggtccaggta catccccgag ggcctgcagt gctcgtgtgg aatcgactac | 660 |
| tacacgctca gccggaggt caacaacgag tcttttgtca tctacatgtt cgtggtccac | 720 |
| ttcaccatcc ccatgattat catctttttc tgctatgggc agctcgtctt caccgtcaag | 780 |
| gaggccgctg cccagcagca ggagtcagcc accacacaga aggcagagaa ggaggtcacc | 840 |
| cgcatggtca tcatcatggt catcgctttc ctgatctgct ggtgccccta cgccagcgtg | 900 |
| gctttttata tattcaccca ccagggctcc aacttcggtc ccatcttcat gaccatccca | 960 |
| gcgttctttg ccaagagcgc cgccatctac aaccctgtca tctatatcat gatgaacaag | 1020 |
| cagttccgga actgcatgct caccaccatc tgctgcggca agaacccact gggtgacgat | 1080 |
| gaggcctctg ctaccgtgtc caagacggag acgagccagg tggccccggc ctaa | 1134 |